(12) United States Patent
Wei et al.

(10) Patent No.: US 6,638,745 B1
(45) Date of Patent: Oct. 28, 2003

(54) ISOLATED HUMAN KINASE PROTEINS, NUCLEIC ACID MOLECULES ENCODING HUMAN KINASE PROTEINS, AND USES THEREOF

(75) Inventors: Ming-Hui Wei, Germantown, MD (US); Kabir Chaturvedi, Gaithersburg, MD (US); Valentina DiFrancesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 122 days.

(21) Appl. No.: 09/916,204

(22) Filed: Jul. 27, 2001

Related U.S. Application Data

(63) Continuation-in-part of application No. 09/804,471, filed on Mar. 13, 2001.

(51) Int. Cl.[7] .............................. C12N 9/12; C12N 1/20; C12N 5/00; C12N 15/00; C07H 21/04

(52) U.S. Cl. .................... 435/194; 435/320.1; 435/325; 435/252.3; 435/6; 536/23.2

(58) Field of Search .............................. 435/194, 252.3, 435/325, 320.1, 6; 536/23.2

(56) References Cited

PUBLICATIONS

Maduale et al., Nature, 394, 491–494, 1998.*

* cited by examiner

*Primary Examiner*—M. Monshipouri
(74) *Attorney, Agent, or Firm*—Celera Genomics; Justin Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

9 Claims, 34 Drawing Sheets

```
  1 GCGGGGGCGGA ACAGATCGCA GACCTGGGGG TTCGCAGAGC CGCCAGTGGG
 51 GAGATGTTGA AGTTCAAATA TGGAGCGCGG AATCCTTTGG ATGCTGGTGC
101 TGCTGAACCC ATTGCCAGCC GGGCCTCCAG GCTGAATCTG TTCTTCCAGG
151 GGAAACCACC CTTTATGACT CAACAGCAGA TGTCTCCTCT TTCCCGAGAA
201 GGGATATTAG ATGCCCTCTT TGTTCTCTTT GAAGAATGCA GTCAGCCTGC
251 TCTGATGAAG ATTAAGCACG TGAGCAACTT TGTCCGGAAG TATTCCGACA
301 CCATAGCTGA GTTACAGGAG CTCCAGCCTT CGGCAAAGGA CTTCGAAGTC
351 AGAAGTCTTG TAGGTTGTGG TCACTTTGCT GAAGTGCAGG TGGTAAGAGA
401 GAAAGCAACC GGGGACATCT ATGCTATGAA AGTGATGAAG AAGAAGGCTT
451 TATTGCCCCA GGAGCAGGTT TCATTTTTTG AGGAAGAGCG GAACATATTA
501 TCTCGAAGCA CAAGCCCGTG GATCCCCCAA TTACAGTATG CCTTTCAGGA
551 CAAAAATCAC CTTTATCTGG TCATGGAATA TCAGCCTGGA GGGGACTTGC
601 TGTCACTTTT GAATAGATAT GAGGACCAGT TAGATGAAAA CCTGATACAG
651 TTTTACCTAG CTGAGCTGAT TTTGGCTGTT CACAGCGTTC ATCTGATGGG
701 ATACGTGCAT CGAGACATCA AGCCTGAGAA CATTCTCGTT GACCGCACAG
751 GACACATCAA GCTGGTGGAT TTTGGATCTG CCCGCAAAAT GAATTCAAAC
801 AAGATGGTAA AAAATGGAAT AAGATAGCTT AATAGAGTTT ATACTAAAAA
851 GTGTTCTTGG TCCTCCTAAG TTTGGGAAGT GTTGGGATAA AATGGTGAAC
901 AATGTTTTGG AGCCTTTTGC AGTGTATGGG GGTGGGGACA GGGACACAGA
951 ACCATTTCCC AGACCGTGGC ACCTTTTTAT TTATGTGCC TGTTAATACC
1001 CTCCAAGACA TTTTTAGGAG CATTGTTATA GTTTGGTTAG AAATAAAGGA
1051 AAATGCTTAA AAAAAAAAAA AAAAAAAAAA AAAAAAAAAA AAAAAAAAAA
1101 AAAAAAAAAA AAAAAAAAAA AAA       (SEQ ID NO:1)
```

FEATURES:

5'UTR:         1-53
Start Codon:   54
Stop Codon:    825
3'UTR:         828

FIG. 1A

Homologous proteins:
Top 10 BLAST Hits

```
                                                                      Score    E
CRA|1800000005161385 /altid=gi|3360512  /def=gb|AAC27932.1| (AF070...  465   e-130
CRA|1800000005168811 /altid=gi|3599509  /def=gb|AAC72823.1| (AF086...  464   e-129
CRA|1800000005168810 /altid=gi|3599507  /def=gb|AAC72822.1| (AF086...  464   e-129
CRA|8900000000196974 /altid=gi|7294566  /def=gb|AAF49906.1| (AE003...  213   4e-54
CRA|8400000015363786 /altid=gi|13648270 /def=ref|XP_008814.3| Rho...   209   5e-53
CRA|6700000040980049 /altid=gi|13592049 /def=ref|NP_112360.1| Rho...   209   5e-53
CRA|1800000005044861 /altid=gi|6677759  /def=ref|NP_033097.1| Rho-...  209   5e-53
CRA|1800000005028208 /altid=gi|4885583  /def=ref|NP_005397.1| Rho-...  209   5e-53
CRA|1800000005169610 /altid=gi|3628755  /def=gb|AAC36189.1| (U4242...  209   5e-53
CRA|1800000005236627 /altid=gi|5174413  /def=ref|NP_006026.1| CDC4...  206   3e-52
```

BLAST hits to dbEST:

```
                                            Score    E
gi|14343911 /dataset=dbest /taxon=960....    831    0.0
gi|11292270 /dataset=dbest /taxon=96.....    743    0.0
gi|12111020 /dataset=dbest /taxon=96.....    517   e-144
gi|12362084 /dataset=dbest /taxon=96.....    492   e-136
```

EXPRESSION INFORMATION FOR MODULATORY USE:
library source of BLAST dbEST hits:
gi|14343911 blood, Proliferating Human Erythroid Cells
gi|11292270 brain, glioblastoma with EGFR amplification Tissue source of cDNA clone:
whole liver

FIG. 1B

```
  1 MLKFKYGARN PLDAGAAEPI ASRASRLNLF FQGKPPFMTQ QQMSPLSREG
 51 ILDALFVLFE ECSQPALMKI KHVSNFVRKY SDTIAELQEL QPSAKDFEVR
101 SLVGCGHFAE VQVVREKATG DIYAMKVMKK KALLAQEQVS FFEEERNILS
151 RSTSPWIPQL QYAFQDKNHL YLVMEYQPGG DLLSLLNRYE DQLDENLIQF
201 YLAELILAVH SVHLMGYVHR DIKPENILVD RTGHIKLVDF GSAAKMNSNK
251 MVKNGIR   (SEQ ID NO:2)
```

FEATURES:

Functional domains and key regions:

Prosite results:
PDOC00004 PS00004 CAMP_PHOSPHO_SITE
cAMP- and cGMP-dependent protein kinase phosphorylation site
    78-81    RKYS PDOC00005 PS00005 PKC_PHOSPHO_SITE
Protein kinase C phosphorylation site
Number of matches: 2
  1    93-95    SAK
  2  248-250  SNK PDOC00006 PS00006 CK2_PHOSPHO_SITE
Casein kinase II phosphorylation site
Number of matches: 3
  1    83-86    TIAE
  2    93-96    SAKD
  3  140-143  SFFE

FIG. 2A

PDOC00008 PS00008 MYRISTYL
N-myristoylation site
50-55    GILDAL

PDOC00100 PS00107 PROTEIN_KINASE_ATP
Protein kinases ATP-binding region signature
103-126    VGCGHFAEVQVVREKATGDIYAMK PDOC00100 PS00108 PROTEIN_KINASE_ST
Serine/Threonine protein kinases active-site signature
217-229    YVHRDIKPENILV

Membrane spanning structure and domains:

| Helix | Begin | End | Score | Certainty |
|-------|-------|-----|-------|-----------|
| 1     | 197   | 217 | 0.789 | Putative  |

FIG. 2B

BLAST Alignment to Top Hit:

>CRA|180000005161385 /altid=gi|3360512 /def=gb|AAC27932.1| (AF070065)
Citron-K kinase [Rattus norvegicus] /org=Rattus
norvegicus /taxon=10116 /dataset=nraa /length=448
Length = 448

Score = 465 bits (1183), Expect = e-130
Identities = 228/251 (90%), Positives = 240/251 (94%)
Frame = +3

```
Query:   54 MLKFKYGARNPLDAGAAEPIASRASRLNLFFQGKPPFMTQQQMSPLSREGILDALFVLFE 233
            MLKFKYG RNP +A A EPIASRASRLNLFFQGKPP MTQQQMS LSREG+LDALFVL E
Sbjct:    1 MLKFKYGVRNPSEASAEPIASRASRLNLFFQGKPPLMTQQQMSALSREGVLDALFVLLE  60

Query:  234 ECSQPALMKIKHVSNFVRKYSDTIAELQELQPSAKDFEVRSLVGCGHFAEVQVVREKATG 413
            ECSQPALMKIKHVS+FVRKYSDTIAEL+ELQPS +DFEVRSLVGCGHFAEVQVVREKATG
Sbjct:   61 ECSQPALMKIKHVSSFVRKYSDTIAELRELQPSVRDFEVRSLVGCGHFAEVQVVREKATG 120

Query:  414 DIYAMKVMKKKALLAQEQVSFFEEERNILSRSTSPWIPQLQYAFQDKNHLYLVMEYQPGG 593
            D+YAMK+MKK  AL AQEQVSFFEEERNILS+STSPWIPQLQYAFQDKN+LYLVMEYQPGG
Sbjct:  121 DVYAMKIMKKAALRAQEQVSFFEEERNILSQSTSPWIPQLQYAFQDKNNLYLVMEYQPGG 180

Query:  594 DLLSLLNRYEDQLDENLIQFYLAELILAVHSVHLMGYVHRDIKPENILVDRTGHIKLVDF 773
            DLLSLLNRYEDQLDEN+IQFYLAELILAVHSVH MGYVHRDIKPENIL+DRTGHIKLVDF
Sbjct:  181 DLLSLLNRYEDQLDENMIQFYLAELILAVHSVHQMGYVHRDIKPENILIDRTGHIKLVDF 240

Query:  774 GSAAKMNSNKM 806
            GSAAKMNSNK+
Sbjct:  241 GSAAKMNSNKV 251   (SEQ ID NO:4)
```

FIG. 2C

>CRA|180000005168811 /altid=gi|3599509 /def=gb|AAC72823.1| (AF086824)
rho/rac-interacting citron kinase [Mus musculus]
/org=Mus musculus /taxon=10090 /dataset=nraa
/length=2055
Length = 2055

Score = 464 bits (1180), Expect = e-129
Identities = 227/251 (90%), Positives = 242/251 (95%)
Frame = +3

```
Query:  54 MLKFKYGARNPLDAGAAEPIASRASRLNFFQGKPPFMTQQQMSPLSREGILDALFVLFE 233
            MLKFKYG RNP +A A+EPIASRASRLNFFQGKPP MTQQQMS LSREG+LDALF LFE
Sbjct:   1 MLKFKYGVRNPPEASASEPIASRASRLNFFQGKPPLMTQQQMSALSREGMLDALFALFE 60

Query: 234 ECSQPALMKIKHVSNFVRKYSDTIAELQELQPSAKDFEVRSLVGCGHFAEVQVVREKATG 413
            ECSQPALMK+KHVS+ FV+KYSDTIAEL+ELQPSA+DFEVRSLVGCGHFAEVQVVREKATG
Sbjct:  61 ECSQPALMKMKHVSSFVQKYSDTIAELRELQPSARDFEVRSLVGCGHFAEVQVVREKATG 120

Query: 414 DIYAMKVMKKKALLAQEQVSFFEEERNILSRTSTSPWIPQLQYAFQDKNHLYLVMEYQPGG 593
            D+YAMK+MKKKALLAQEQVSFFEEERNILSRTSTSPWIPQLQYAFQDKN+LYLVMEYQPGG
Sbjct: 121 DVYAMKIMKKKALLAQEQVSFFEEERNILSRTSTSPWIPQLQYAFQDKNNLYLVMEYQPGG 180

Query: 594 DLLSLLNRYEDQLDENLIQFYLAELILAVHSVHLMGYVHRDIKPENILVDRTGHIKLVDF 773
            D LSLLNRYEDQLDE++IQFYLAELILAVHSVH MGYVHRDIKPENIL+DRTG IKLVDF
Sbjct: 181 DFLSLLNRYEDQLDESMIQFYLAELILAVHSVHQMGYVHRDIKPENILIDRTGEIKLVDF 240

Query: 774 GSAAKMNSNKM 806
            GSAAKMNSNK+
Sbjct: 241 GSAAKMNSNKV 251   (SEQ ID NO:5)
```

FIG. 2D

```
>CRA|1800000516881O /altid=gi|3599507 /def=gb|AAC72822.1| (AF086823)
     rho/rac-interacting citron kinase short isoform [Mus
     musculus] /org=Mus musculus /taxon=10090 /dataset=nraa
     /length=494
     Length = 494

Score =  464 bits (1180), Expect = e-129
 Identities = 227/251 (90%), Positives = 242/251 (95%)
 Frame = +3

Query: 54   MLKFKYGARNPLDAGAAEPIASRASRLNLFFQGKPPFMTQQQMSPLSREGILDALFVLFE 233
            MLKFKYG RNP +A A+EPIASRASRLNLFFQGKPP MTQQQMS LSREG+LDALF LFE
Sbjct: 1    MLKFKYGVRNPPEASASEPIASRASRLNLFFQGKPPLMTQQQMSALSREGMLDALFALFE 60

Query: 234  ECSQPALMKIKHVSNFVRKYSDTIAELQELQPSAKDFEVRSLVGCGHFAEVQVVREKATG 413
            ECSQPALMK+KHVS+ FV+KYSDTIAEL+ELQPSA+DFEVRSLVGCGHFAEVQVVREKATG
Sbjct: 61   ECSQPALMKMKHVSSFVQKYSDTIAELRELQPSARDFEVRSLVGCGHFAEVQVVREKATG 120

Query: 414  DIYAMKVMKKKALLAQEQVSFFEEERNILSRSTSPWIPQLQYAFQDKNHLYLVMEYQPGG 593
            D+YAMK+MKKKALLAQEQVSFFEEERNILSRSTSPWIPQLQYAFQDKN+LYLVMEYQPGG
Sbjct: 121  DVYAMKIMKKKALLAQEQVSFFEEERNILSRSTSPWIPQLQYAFQDKNNLYLVMEYQPGG 180

Query: 594  DLLSLLNRYEDQLDENLIQFYLAELILAVHSVHLMGYVHRDIKPENILVDRTGHIKLVDF 773
            D LSLLNRYEDQLDE++ IQFYLAELILAVHSVH MGYVHRDIKPENIL+DRTG IKLVDF
Sbjct: 181  DFLSLLNRYEDQLDESMIQFYLAELILAVHSVHQMGYVHRDIKPENILIDRTGEIKLVDF 240

Query: 774  GSAAKMNSNKM 806
            GSAAKMNSNK+
Sbjct: 241  GSAAKMNSNKV 251           (SEQ ID NO:6)
```

FIG. 2E

Hmmer search results (Pfam):
Scores for sequence family classification (score includes all domains):

| Model | Description | Score | E-value | N |
|---|---|---|---|---|
| PF00069 | Eukaryotic protein kinase domain | 131.2 | 1.9e-35 | 1 |
| CE00359 | E00359 bone_morphogenetic_protein_receptor | 5.8 | 0.57 | 1 |

Parsed for domains:

| Model | Domain | seq-f | seq-t | hmm-f | hmm-t | score | E-value |
|---|---|---|---|---|---|---|---|
| CE00359 | 1/1 | 219 | 249 .. | 274 | 304 .. | 5.8 | 0.57 |
| PF00069 | 1/1 | 97 | 256 .. | 1 | 147 [. | 131.2 | 1.9e-35 |

FIG. 2F

```
   1 GGGTGACGGA GTGAGATTCT GTCTAAGAAA AAAGAAAAAA AAAGAGGTGC
  51 TTGATAAATA GTAGCTATCC ATTATTGGCC CCGGGAACAA GAAGTAAGTT
 101 ATGTTTGGGG AAGGAAAAAA GAACAAATGT GTATTAAGCA AGCCTGTAGC
 151 TCTAATTATG TGCTGGTGTG CGTGTGTGTG TGTGTGTGTG TGAGAGAGAG
 201 AACACATCTC CAGTTCTGTC TACTGTAGAA TTAGGAGAGT ACAAAAGGA
 251 CTTTACATAT ATAAATAGAA CATACACACA CACACATGCG TGCACACATA
 301 TACACACAAT TTAATCATTA TGAAACCACA TCCATATTGT TGCTACCTAG
 351 GTTAAGAAAT AGATCACAGC AGCACCCCAA CACCCTGAAA GGCCTCCATC
 401 CCAACCCCAG GTAACTACTA TTCTGGCTGT TGCTTTCTTT ATGGTTTTGT
 451 CATTACTTTA AACAATGACA AAAACTGCAA TGATTTGCAT CAACCTAATA
 501 CATCCCTCCT TAAACAATGT TGCTTTGTTT TGTCCTGTTT TGGAACTTAT
 551 AAGAATGGAA TCATAATGGA ATCATATGTT ATTTTCTTGC TTCCTTCATT
 601 AGGCCTTGTT TTGAGACTCA TTATGTCATT GTGGTTAGTT GCAGTTTATT
 651 CTTTTTCATT GCTTGTGAAA ACACTGCAAT ATACAATTTT GTCTTTTCTA
 701 CTGCTGATGG ACATTTATAT CACTTCCAGT TTTTTGCGAA CACTATTTTG
 751 TATTCTTATA CACATCTCTT GGTGTACATA AGTAGGAGTT CTCGCCGGC
 801 GTGGTGGCTC AGGGCCTGTA ATCTCAGCAC TTTGGGAGGC CGAGGTGGGC
 851 AGATCACTCG AGGTCAGGAG TTCAAGACCA GCCTGGCCAA CACGGTGAAA
 901 CCCCATCTCT ACTAAAAATA CAAACAATTG GGCATGGTGG CATGCACCTG
 951 TAATCCCAGT TACTTGGGAG GATGAGACAA GAGAATAGCT TGAACCTGGG
1001 AGGTGGAGGT TGCAGTGAGG CGAGATCGTG CCATTGCACT CCAGCCTGGG
1051 AGACAGAGCA AGACTCCATC TCAAAATAAA TAAATAAATA GGAGTTTTTC
1101 TTAGGTAGAG AAACTACACC TAGCAATAGT CATAGAATGC ACAAATCTTC
1151 AATGTTAGCA ATAATGCCA ACTTTTTTT TCAAATTTCA AAGAGATTGT
1201 ATCCATTTAC ACGCCTACGG GTACTGTATA AGTGTGTGTA CTTCCACATC
1251 TTCGCAAACA CTGTCACATC CTTTTGTTGT TGTTGTTCTC GAATTTGAGT
1301 GTTATTCTTT CTCACTGTGA CTTTATTTTT CATATTTTCT GATTATGAAC
1351 GAGGTTGACA ACTTTCACAC ATTTGTTGGT CATCTGGATT TCCTTTTTGG
1401 TGAAGTGCCT GTTTAAGTAT CTCGTCTATA ATTTATTTTA AAGTGTCCTT
1451 TCAGACAGTC TCAATGACTG TCACCAACTC CTTGCAGGGC AGTCAGCCCG
1501 GAGATAGAGT AATCAAGGTA GGTTGAAGTC AAGCTCAAAA CATTCGCTGC
1551 CTCAGCTGTA GCAGAGGACC ACTGGGCTTC CCCAGGTAAC AAGTACTTCT
1601 ACCTTAGCCA CATGAGAGAG AAAGAAGACC AGGCAGAGCA GCCTGGCTGC
1651 CTTCCTCCTT GCAGGTGGCC GAGAGCAGGG GACAGCGCCC TGGCGACCTC
1701 CTCAGGGATC CTAGATTAAC AGTCGCGTCC TCAAACGCAG CATCCTGCGT
1751 AACCGCCAAT TCAAACTTC CAAGACCTGC CCTGCTGATT TTGCCCTTCC
1801 CTTTTTCCCG TTGGTCGCGA GTCAAAGGAA GATGCAATTT GATTGGCTCT
1851 CCCCTTCACT TTCCTCCATG CCTTTAGGGA CATGGGCGGG GCCTGGCTGA
1901 GACGCCCATG TCTATCATAG GAGCGGAGAC GCTGATTGGT CCAAACACGG
1951 CTGAGACCCG CCCGCGCCGT TCCTCGGGTT CAAACGCGGC GGCGGGAGGC
2001 GCGGGCGGA ACAGATCGCA GACCTGGGGG TTCGCAGAGC GTGAGTCTGA
2051 TCCCCCAGAC CCAATTCTAC CGCACCCGGC TCTGCAAGGC CAGGGGAGGG
2101 CCGCCTCCAC CCATACAAGT CCCGGGTTTC CCTCCCGCCC CGGGGAGGGC
2151 GGCGATTCCA CCCCCAGGGC TGCGGGAGGC CTGGAGGGTC TTCCGGGGCT
2201 AGCTGTGCGC GCGCCCACCT TCCTTGGGAG CCGAGGGGTC AGCCGAGTGG
2251 TGCTGGGGCA GGAGGCTTGC TCCTCCCCTA AACCAGGCGG AGTGCTTTGT
```

FIG. 3A

```
2301 CTCTTCAGCT CTGCCTCCTG TCAGCACTAA CTGCATTATT CTGCCCAGTG
2351 TAGTCGGCCG GTTCCTTATT ATCTGCGTGA ACTTAGCCAT TTACTTAACC
2401 TCTCTGTTTC AGCGTATTCA TACCCGTGC CCACCCCATC ACCTCATGAT
2451 GCCCCCGCCT CTTTCGCTCT GCTCCAGTCC GTCTGGCCTC GCTGTTGCTG
2501 GAGAGGCCAG GTCCTGCCTC AGTGCTTTTG GCTTGGCTGT TTCGTTTGCC
2551 ACGGATGTCT TTCTTTCCCC AGATATCAAC ATGGCTTGCT GGTCATTCGC
2601 TTCAGGTCTT CAAGTCTTGG GTCAAATGGT GGCTTCTCAG TGAAGTCTTA
2651 TTTGACCACA CTAAAAATTG CACCATCTCA CCCCATTGT CCTTTTCTTG
2701 CTCGATTTTG TTTTTACCCC ATAGCACTTA ACACCTTACA ACAAGCTATA
2751 TATTTTGCTT ATTTCAGTCA TTCATTTAAT AACTATTCGC ACCTATTTGT
2801 GTGCCAGGCT ATGTGTGCCC CCACTGCATG GGGGCAAACA TCTCTGCCCT
2851 TGTGGAGCTT CCATTCTAAG GGGGGAGATA ATAAACACAT TTATAAGTAA
2901 GAGAGTATGT CAGATAAGTG TATCATCTCC TGTCACAGTG AGTTAAAATC
2951 TGGTGTTTAA TCTCCATGAT TAGACTGAGC TTCCTAAAAC TGGAGTGGTA
3001 GCTGATTTTC ACCTCCTTGT CCCTGATATC TTGAGGGAGA TCAGGATCTC
3051 TCAGGCCCTT CCTGCTCAAA ACATAGGACA CACTTGACTT TTCTGATATC
3101 CTTTCAGCGC CAGTGGGGAG ATGTTGAAGT TCAAATATGG AGCGCGGAAT
3151 CCTTTGGATG CTGGTGCTGC TGAACCCATT GCCAGCCGGG CCTCCAGGCT
3201 GAATCTGTTC TTCCAGGTAA CAGCCTACCC TGCCAACTTT GCTCACCTGT
3251 GTGTGTCCTT GGAATCTCCT TGTCACTCAC CTTTGCTTTT ATTTATTTGT
3301 TTATTTATTT AGAGTCTCAG TCTCTCAGGC TGGAGTACAG TGGTGCAATC
3351 TCAGCTCACT GCAACCTCCG CCTCCTGGGT TCAAGCGATT CTCCTGCCTC
3401 AGCCTCCAGA GTAGCTGGGA CTACAGCCGC TGCCACCAC ACCCGGCTAA
3451 ATTTTGTATT TTTCTTTTTA GTAGAGACGG GGTTTCACCA TGTTGGCCAG
3501 GCTAGGGTCG AACTCCTGAC CTCAAGTGAT CCACCTGCCT TGGCCTCCTA
3551 AAGTGCTGGG ATTACAGGCA TGAACCGTGC CCAGCTTGCT TTTATTATAG
3601 GACCAGGGAT AATATTTTAG GGGAAATTCT GTTTTGTTTT GTTTGAAACA
3651 AGGTCTTCTG TCGACTCTAG GCCTGTGCCA CCATGCCTGG CTAATTTTTT
3701 AATTTTTTGT AGGGATGGGG TCTCACTGTG TTGCCCAGGC TGATATAGAA
3751 CACCTGACTT CAAGTGAGCC TCTTGCCTTG GCCTCCCAAA GCACTGGGGT
3801 TATAGGTGTG AGCCACTGCA CCTGGCCCTC TATTTAGAGT TTTATATGCA
3851 CTGATTCTTT TGGAAAAAAG ACACTGTGCA GAAGTAGATA GCTGAACTTG
3901 CCTTAGAAGG GAGATCTTTT CATATTTCTC ACACTTTACA CTTCTGTACT
3951 AAAGTTTATT CATTCATTGA TTGATTGGTT GCTTGCAAGA CAGGGTCTTG
4001 CTCTGTGGCT CAGGCTGGAG TGCATTGGCA CAATCACGGC TTACTGCAGC
4051 CTTGACCTCC TGGGCTCAAA CGATCCTCCC ACTTCAGCTT CCTGAGTAGC
4101 TGGGACCACA GGTGTGTGCC ACCATACCTG GCTAATTTTT GTATTTTTTG
4151 TAGAGATGAG GTTTCACCAT GTTGCCCAGG CAGGTCTCGA ATTCCTGGGC
4201 TCAAGTGATC TACTTGTCAC AGCTTCTGCA AGTGTTGGGC TTACAGGCAT
4251 AAGCCCCTGT ACCAGGGCAA GTTTGTCCTT TTATTGAAGA AGAAAAATA
4301 AATGAACAAA GATGCTTTTT AAAACTACAA TTTCTGTGGG TATAATCCTA
4351 TTCATTTTCA TTGCAGGGAT GTTTATTTTT TAAGATTTTT TTTTTTTTT
4401 TTTGAGACAG AGTCTTCGCT GTCGCCCAGG CTGGAGTGCA GTGGCGCGAT
4451 CTCGGCTCAC TGCAGGCTCT GCCCCCGGG GTTCACGCCA TTCTCCTGCC
4501 TCAGCCTCCC ACGTAGCTGG GACTACAGGC GCCCGTCACC TCGCCCGGCT
4551 AATTTTTTGT ATTTTTAGTA GAGACGGGGT TTCACTGTGT TAGCCAGGAT
```

FIG. 3B

```
4601 GGTATTTTTT AAGATTTTAA AAAAAGTTTT GATGAATACC ACACCTGTTT
4651 AACCCTCATT CCTCTCAAGA TACACATTTC TGTCACCCCA GATGCGTTAA
4701 AACTTAATAT CATAAGATTA CTTCCAAATA GATTTTAAT TCTTTTGTTT
4751 CTGATGTATG TGGAACACTG GTGAAGTAGA AATCCTTGTT TGATTTATGT
4801 ATTCGTAAGT CAGGGGGACA ATAGAGACCA TGAAGATTTA GAATTGAATC
4851 CCAGTCCCAG CACTAGTTAG CTGCATTACT TTGGGTGAGT CAGTTACCTT
4901 TTCTGAGTCC ATTTGCTATT CTTTAAAATA GGTTGTAGCC TGTAATGCCA
4951 GTATTTTCGG AGGCTGAGGC GGGCGGATTA CTTGAGGTCA CGGGTTCGAG
5001 ACCAGCCTGG ACAACGTGGT GAAACCCTGT CTCTACTAAA AATATAGAAA
5051 ATTAGCTGGG CATGGTGGTC GCATGTACCT GTAATCCCAG CTACTTGAAA
5101 AGCTGAAGCA GGAGAATCAT TTGAACCCGG GAGGCGGAGG TTGTCGTGAG
5151 CCGAGATGGT GCACTGCACT CCAGCCTGGG CGACAGAGTG GGTAAGACTC
5201 CATCTCAAAA CAAAACAAAA CAAAAGAAAA CAAAAAAAAT AACATAGAGG
5251 TTGTAGTACC TAATCCACAG GGTTGTTGTG AGGATTAGAT GAGATATTCG
5301 ATTTAAAGCA CTTAGCACCT TGCCTGGCTC TTAGTAAACT CCTTATAAAA
5351 AATGGTAATT ATTGTTAATA CTCAGCATAG AATAGTATTA GTTATAATAT
5401 TAATACTAAA TTTGTTTCCT TAATAGTAAT TATATTTGGG AAGGTAGTTA
5451 TGTAGGATAC CTGTAAGATG ATGAATGATG AAGTATTCTT GATAACTTTT
5501 TTTTTTTTC CAAAATATTG GTATTGGGTG TTTAAACAGA TGAGAGTGGA
5551 AACAAATTGA AGCTTAGGT TTTTCTGTGG GACCATCCCC ATCAGCATTT
5601 TAAGTCTTGA CATATCTTTC ACAAATGAAT AGTCTGTCTT TAACCTTAGA
5651 TGGCTGGAGT GCTGCCACGT TCAGCCCCT TTATCATGCT ACTTTAAAAT
5701 ATCTCCAACT TGCTGGGCGT GGTGGCTCAC GCCTGTAATC CTAGCAATTT
5751 GGGAGGCTGA GGTGGGTGGA TTGCTTGAGG TCAGGAGTTC GAGAGCAGCC
5801 CGGGCAACAT GGTGAGCCCC TCCGTTTCTA CTAAAAACAC AAAAAATAGC
5851 TGACTGTGAT GGTGTGTGCC TGTAGTCCCA GCTACTCGGG AGGCTGAGGC
5901 AGGAGGATCA CTTGAGCCCT AGAGGCAGAG GTTGCAGTGA GCTAAGATTG
5951 TGCCACTGCA CTTCAGCACT TCAGCCTAGG CGACAGAGCA AGACCCTGTA
6001 AATTAAAAAA AAAAAAAAAA AGAAAAGGAA AAAAATTTCC AACTTATTAA
6051 GGGCTTATAG TGTGCTGATT ATGTAATAGT TATGGCTTCC AATGTGTCTG
6101 GCATAGAACT GGCATGTTTC TGAGTATCTC ACTTCAGCCT CATGACAGAG
6151 GTAAGGACTA TTTTTAATTT AAACTTTAAA TAGGAGGCAA CAGGCCAGGT
6201 GTGGTGGCTC ACACCTGTAA TCCCAGTACT TGGGAGGCT GAGGCAGGTG
6251 GATTGCTTGA GTCCAAGAGT TCAAGACTAG CCTGGGCAAA ATGGTGAAAC
6301 CCCATCTCTA CAAAAAATAT AAATAATTAG TCAGGCATGG CGGTGTGTGC
6351 CTGTAGTCCC AGCTACTCAG GAGGCTGAGG TGGGGCATC TCTGGGGCCC
6401 CGGAGGCAGA GGTTGTAGTG AGTTGAGATT GCAACACTGC ACTCCAGCCT
6451 GGGCAACAGA ACGAGACCCT GTTTCTAAAT AAATACATAA ATAGGAGGCA
6501 ACAGATATAG ACAGATATGG AGGTAGGTAA GGCCTTGCCC AAGATCATAC
6551 ACGTTGGGTT TTGCAGATGA GGCCAAGATC AGACTCCATC TTTGGTTGGT
6601 CTGACTCCAA AGGCTGACCA CATAGCCATT GGGCCACAGC ACCTGTGCAC
6651 GTCAGAATTT ATTAAGTATA TCTTGTATTT AGTCATTATA ACAGGAAGAC
6701 TTATGGGTAA ACCCTCAGTT CATCTCTTTT TAATGCTGAG ATCCCCCTGC
6751 CCAGTAAAGC TATTATTGCA AGTATAGTAT ATACCTATCA TTTGCCTTGA
6801 GTTATCAGGT AAGGATGCTG TTTGTTCTTT TCCCATATAG TGCTGTTTGA
6851 ATGAGGTTGA GATACAGTAG CAATTTTGTT TTCCATTCAG GTGAGTACCT
```

FIG. 3C

```
6901 TAGACTGAGT GTCATTTTGT CTTTTTTACT TCTACTCAAC AGGATTTCCT
6951 GACATGTTCG AGGTCAGTGA TTGTCAGACT TTCTGAGCCA GCAAAATTTC
7001 CCAAATTGCT GGGTAGACAC AGGTTTTCCA ACTTTTTATT TTGCCAAGTA
7051 AGGATATATA AAAAAAAAAT AAAAGAAAG ACCTATTATT TTCTGGCCCT
7101 TGTATTTCAT AAAGGGCATT TTAAGAAACA ACAAGACAGG AAGAACATCA
7151 TCTCAGAATA AAGGACCATT TTTAAATTTG AATACATTTA GTTTTATAAA
7201 AAAGATATCA TGTGGTGTTC ATTTTTTCTC ATTTCACTGC AGGCTGTTGA
7251 AAACTTTGTT AAGAACCAGT ACTATATTTG GAACCCCTG CTTTAATTGA
7301 TCTAAACTCT TGAAGAATAG AAGAAACAAA GCATTTATT TTTCTGAGTT
7351 ACTGGCAACT ATTACTAAAG TGACAGATAT GGTGGCCTTG AATGCAGTGC
7401 TTCCCAAACC TGATTGAGGT CTGACTCTCT TGGGGACCAG GGTCTCATTC
7451 TGTTGCCCAG GCTGGAGTGT GGCAGCACAA TCTTGGCTCA CTGCAGCCTT
7501 TACTTCTTGG GCTCAAGTGA TCCTTCTACC TCAGTCTCAC AAGTGGCTAG
7551 GACTACAGGA CCATGGCACT ACCTGGCT AATTTTTTT TGTTTGTTTG
7601 TAGAGATGGG ATCTCGCTGT GTTGCCCTGG CTGGTCTTGA ACTCCTGGGC
7651 TCAAGTGATC CTCCCACCTT GGCCTCCCAA AGTGCTAGTA TTCCAGGTGT
7701 GAGCCACCTC TCCCTGCTGG GAACTTGTT AATAAAACAG ATTCTAGGCT
7751 ACAGTCTGGA AAATTCTAAT TCATTTGGTT GTGGGGGAGG GGGCATAGG
7801 ACCAGAGAAT GTGTTTGTTT GTTTGTTTGT TTTCTTAAA TTCTCCAGTG
7851 CTGTTGTGAT TCAAATGCAG CCGGTCTGTT TCTGTTATCA AGTGCTGTGT
7901 AACAAAGCAC TCACAAAGTT TAAAGCAACA ATGATTTATT TTTTCTTAGG
7951 ATTCTGTGGG TTGGCTGGAC TCAGCTAGGT AGTTCTGCTT CATCCTGTGA
8001 TGTCAGCTGG GGTCACTTGT GGGGCTACAT TCAGCTGGGA TTATGTCTGG
8051 GACTGGAACA TGTGGGTGCT GACTGCTGGC TGGGGCACCT TAGTGTTTCT
8101 CACATGGCCT CTCTTCTCCA TGAGGTCTTT CAGTAGTATA GCCCAGGACT
8151 CGTAACTTTT TTTTTTTTTT TAAGACAGAC TGTCGCCCTG TCGCCCAGGC
8201 TGGAGTGCAG TGGCACGATC TCTGCTCACT GCAACCTCCG CCTCCTGGGT
8251 TCAAGCAATT CTCCTGCCCC AGCCTCCCGA GTAGCTGGGA TTACAGGCAC
8301 GTGCCTCCAC GCCCGGCTAA TGTTTGCATT TTTAGTAGAG ATGGGGTTTC
8351 ACCACGTTGG TCAGGCTGGT CTCGAACTTC TGACCTCGCG ATCCGCCTGC
8401 CTCGGCCTCC CAAAGTGTTG GAATTACAGG TGTGAGCCAC TGCACCTGGC
8451 CGACTCGTAA CTTTTTTTGT AAGTAATAAA TATTTTAGGC TTTGTGGGTC
8501 CTGTAGTCTC TGTTGCAACC ACTCAACTTG GCCATGGTAG CACAAAAGCA
8551 GCTAAAGACA ATATGTAAAT GATGGGTGTA GCTGTGTTCC AGTAAAACTT
8601 ATAAAAGTC CGTGGGCTGG ATTTGGTCCA AGGGCTACAG ATTGCACACC
8651 CCTGGTCTAG CCCAAGCATC TGTGCATGGT GGCTGGCTTC CCAAAAGTGG
8701 AAGCTGCTAA GCTGCCTTTT TTTTTTTTTT TTTTTTTTTT GAGAGGGAGT
8751 CTCACTGTGT TGCCTAGGCT GGAGTGCGGT GGTGTGATCT CGGCTCACTG
8801 CAACCTCCAT CTCCCGGGTG CAGGCAATTC TCATGCCTCA ACCTCCCAGG
8851 TAGCTGGGAT TACGGGTGCC TACCACCACG CCTGGCTAAT TTTTGTATTT
8901 TGGTAGAGAC AGGGTTTCAC CATGTTGGCC AGGCTGGTCT CAAACTCCTG
8951 ACCTCAAGTG ATCCACCCGT CTTGGCCTCC CAAAGTGCTG GGATTACAGA
9001 TGTGAGCCAC CGTGTCTGGC CGCTTGACAA GCTTCTTAAA GGCACTGCCC
9051 TGAACTGGCA CAGTGTCACT TGTGTCACAT TCTTTTGGTT GAAGAGAGTC
9101 TCAGAGATGG CACAGATTCA AAGGCAGGAG AAATAGACTC CAGCGCTTAA
9151 AGTAAGGAGT AGCATGTGCC TACAGAATTG GAGGAACTGT TGGAGGCCAT
```

FIG. 3D

```
 9201 CTTTGAAGAG AGACCACCAC TATCCATGGC TTGGCACGTG GGAATCACTG
 9251 CTCTATACCA GGGTTGCAGA CTCATGTCTT TGGGGGCCAG GCAGTGAGTA
 9301 TAAATGAGTC AAGTGGGCCA GTTGGAAGAT GGAGTCAGAC CTGCAGTGAA
 9351 CTCCCAAACA CATCTGCTAC CGGGAGGGGC AGCATTACTC AGCTCCAGCT
 9401 CAGCGTCATC AGGCAGGAAG GCGAGGCAGT GTTGCCGGAT GTGCCAGTGT
 9451 TTCAAAAGAA GCCAGAGACT CCATTTTTAT TTTTTTGTAT GGAATCTCCT
 9501 GATTTTGAAA TATTGGCAGA TAATTCAAAT TATCTTAAAC ACTACAGGCC
 9551 AAACAAAACA TATCTGTGGG CTAGAGACAG TCTGCCAGTT TGTAACTATT
 9601 TCTCCAGATC ATGAGTAAAT TTGGCTTTAC GATGGTCACT CAGTTCTTAT
 9651 TACTCTAGGT TGTTCAAATG AATTAAAAAA GCTGAAATTA TATGAATAAA
 9701 CCCCTGGGCA CACATGAAAG AAGTGAAAAA CCCATTGTTT CCTATTGTAG
 9751 AAACATGGAA GCATGTCAGA GCCAGAGGAT CCAGAGGAAA TATTCTCACT
 9801 AGCCTCAGAC CCTCAGGAGT GAGGGAGCTT TCTTGTTAA TGGCCACGCT
 9851 TGTGCAGTTT TCCTTCCCAG GTGCTGGTGA AGAAACCCA CAGTCTTGGA
 9901 ATCATGGAAG TGATACCATA ATGACTGTCA GTTGACGTTG CTTTAAAGAA
 9951 TGAAGCCACA GAATTGTGCT GTTAGCATGT CGTGAGCAGT TAGTTGAGTT
10001 GGTGGCTTGT AATTTACTCT GTGTGGATGT TATTGATCAA AGCTTTTCAT
10051 TATTGACAGT GTCTCCATCT GCTGTTTGCT GTTTTAGGG GAAACCACCC
10101 TTTATGACTC AACAGCAGAT GTCTCCTCTT TCCCGAGAAG GGATATTAGA
10151 TGCCCTCTTT GTTCTCTTTG AAGAATGCAG TCAGCCTGCT CTGATGAAGA
10201 TTAAGCACGT GAGCAACTTT GTCCGGAAGT GTAAGTTTGG GGAACTTTTT
10251 CTTGAAAACT GTCCTGAGAG AGAAAAACTA GAAAGATGCT TGAGGCAGAA
10301 TGAGTTACTG GTTGATAGTA GTCGGTAAGA ACTCTGGTTC TATATAAGAC
10351 AGATCCAGGT TCAAATTCAG GCTGCACCTC TTATAGCTGG GAGACCAGGT
10401 AAGTTGGGCT TCTTGGTTGC AAGCGACAAA CTTAATTCAA AGACTGAATT
10451 TAGGCCAGGT GCAATGGCTC ATACCTATAA TCTCAGCCCT TTGGGAAGCT
10501 GAGGTGGGTG AATCGCTTGA GCCCAGGAGT TCAAGACCAG CTTGGGCAAC
10551 ATGGTGAAAC CCCATCTCTA CAAAAAATAC AAAAATTAGC TGGGTATGGT
10601 GGCTTGCACC CGTGGTCCCA GCTGCTGAGG AGGCTGAGGT GGGAGGATCA
10651 CTGGAGCCCG GGAGGTTGAG GCTCAATGAG CTGTGATTGT GCCATTGCAC
10701 TCCAGTCTGG GTGACAGAGT GAGACCCTGT GTGAATAAAA GAGTGAATTT
10751 ATTGGCTCAT GAAACTGAGA AATCCAGGAA TGAGTTAAGT TTTAGCTTTA
10801 GGCATAGCTA GTTCCAGAGA CCTCAATAAT ATCCCGTGGC CCTGTCCTTA
10851 TACTCACTCA GGGCTGACTT TCTATTAGGC AGAGTAGGCA CGGTGCTTAG
10901 GATCTGTGAT ATTTAATTTT AATGAATTTA ATTACTTTTA ATTAACTGAA
10951 TTAAATTTTA ATTTGTTTTA AAATTATAGG AAAAATGAAT ATAATAATGT
11001 ATAATGATTC TGGATTACAT TCATCTTTAT ACTAATGTAG TCATAAAATA
11051 TAATTTTTGT TTTTTTTGGA GACAGAGTCT TGCCCTATTA CCCAGGCTGG
11101 ATTGCAGTGG TATATCATGG CTCACTGCAG TTTCAACCTT CTAGGCTCAA
11151 GCAATCCTTC CACCCCAGTG GCTGGGACTA CAGGCTCACA CTACCACGCC
11201 CAGCTAATTT TTGCTTTTTT CTCTGTAGAG ATAGGGTCTT ACTATGTTAC
11251 CCAGGCTGGT TTCAAACTCC AGGCTTGAAG CAGTCTTCCT GCCTCAGCCT
11301 CCCAAAGCTT TGGGATTACA GGTGTGAGCC ACCATGCCTG GCCCCATAAA
11351 ATATAATTTT TGAATTCTTT TTTGTTTTTA ATGGAGGAAG GGGCTGAGGA
11401 AGGCAAAAGT ACCTAGGGCC TATGAAGTCA TATATTGGCC TTGCCTTCAC
11451 CCTGTTTCTG ACTTTGCTTG ACTTCCATGT GATGAGGCAG TTGGCTGTTA
```

FIG. 3E

```
11501 GTGTCCCAGT TTCATACTCT TACATTAGTG TTTTTCAACC AGTGGGTGAT
11551 TTGACGTTTT CGGTTGTCAG AGCTAGTTGG GGGTGGTGGT GTGTGAGTTT
11601 GGGGGGAAGG GTCCTACTGT CAGTTAATGG GTGAGGCCAG AGATGCCACC
11651 AAACACCTTA CAGTGCACAA AGCAGCCCCC ATAACACAGA ATTATGTAGC
11701 CCACAATGCC AACAGTGCTG AATTTGAGAA ACCCCACCTT GTACAACATT
11751 GCTGTGCAAC CAACCACCCT AAATATTACT GACTTAAAAC AATAGTCACT
11801 GTGGCTGGGC GCGGTGGCTC ATGCGTGTAA GCCCAGCGCT TGGGAGGCT
11851 GAGGCGGCGG ATCACTTGAG GTCAGGAGTT CCAGACCAGC CTGGCCAACA
11901 TGGTGAAACC TTGTCTCTAC TAAAAATACA AGAATTAGCT GAATGTGGCA
11951 GCGGGCGCCT GTAATCCCAG CCATTTGGGA GGCAGAGGCA GGAGAATCGC
12001 TTGAACCTGG GAGGTGGAGG TTGCAGTGAG CCAAGATCTC ACCATTGCAC
12051 TCCAGCTTGG GCAATGAGTG AGACTCTGTC TTAAAAAAAA AAAAAAGTTA
12101 TTGTATTACC TCTTGTGTGT GTAGGTTAAT TGGACTCAGC TGGGGATTCC
12151 TCTGCTCTGT ATTACATTGG CCAGGATTGC AGTCACCTGG GGCTCTCCTG
12201 GGCTGGAATG TGTGAGAGGG CTTACTCAGT GTTTGGTGCC CTGGCTTGGA
12251 GGCTGGGCCC AGCTGGGCCT CTCTCTTC ATGAAGTTTC AGGGCCTTTT
12301 GCTGTCCACA TGGCACCTCT ATGTGGTCTC CAAATCAGAA GTCAAGGAAC
12351 TACAGCCTGT GATGCCTATT TTGTAAAGAA GGTTTTACTG GAACACAGCC
12401 CTACCCATGT GTTTGTACAG TGCCTATGGC TGCTTTCACA TCATAACAGC
12451 ATTTTATTTC ATTTTATTTA TTTTTTTTTG AGACAAAGTC TCACTCTGGC
12501 TGGAGTGCAG CAGCACAATC ATAGCTCACT GCAGCCTCCA ACTCTTGGGC
12551 TCAAGCAATC CTCCTGTCTC AGCCTCCTCA GTAGCTAGTA CTACAGGCCC
12601 ATGCCACCAC TAATGGCTAA TTTTTTAATT TTGTGTAGAG ATGGGACCTT
12651 GTGAGATTGC CTAGGCTGGT CTTGAACTCC TGGCCTCAAG AAATCCTCCC
12701 ACCTTGGCCT CCCAAAATGC TTGGATTACA GGCATGAGCC ACTGTGCCCA
12751 GCCCACAACA GCATTTGAGT AGTTGTGATA GAGACCAAAT GGCCTACAAA
12801 GCCCAAAATA GTTCCTGTTT GGCCCATTTC GAAAAGGCTT GCTGACCTCT
12851 GAGCTACATG GTCTCTCTAG CAGGACAGCC TCGACGGTAG CTCAGGTTTC
12901 CAAAACACAA AAGTGGAAGC TGCCAGGCTT TCTTAGGGGT TATCCTAGGA
12951 GGGACATAGG ATCTCTTTGA CTGCATTTTA TTGTTTGATG CATGCTCTGG
13001 GGCTGCTCAA ATTCCACCTG AGAGGAAACT ACACAAGGTC ATGAATCCCA
13051 AGAGGACTGG GGCATTGGGT GCTATTTTTG GAGACTGGCT ACCACACCCT
13101 GCCCAATGGT AATCTTCCCT TATCTAGATT AATACAACCC CAGGGAAGAT
13151 TCTAACTTGG CTCTGCTTTG GGTCATTTGC CTCCCTGGAG GTGAGGTGTT
13201 GTGATCGGTT TTGTTGGAAT GCCCAAAGGG GTCAGGGCAG TGTGATTACC
13251 AGGACCTCAT GGAATGGGGG ATGCGTGGTT ATGCAAAGGA GCCGGGGATG
13301 CTGGGTAGAA AAAAAATCAG CATATGTTCA CTATAGTGCT CTTCAGTATT
13351 TTACATGTAC TTTGTTCTCA GTTTTCTCAT CTGTAAAATA GGAATAATGT
13401 ATATCCTTTT TTTTTTTTT TTTTGGAGT CTTGCTCTGT TGTCCAGGCT
13451 GGAGTACAGT GGCACAATCT CAGCTCACTG CAACCTCCGC ATCCCGGGTT
13501 CAAGTGATTC TCCTGCCTCA GCCTCCTCAG TAGCTGGGAC TACAGGCGTG
13551 CACCACCACA CTCAGCTAGT TTTTGTATTT TTAGTAGAGA TGGGGTTTCG
13601 CCATGTTGGC CAGGCTGGTC TCAAACTCCT GACCTCAAGT GATCTGCCTG
13651 CCTCGGCCTC CGAAAGTGCT GGAATTACAG GCATGAGCCA CCACGCCCAT
13701 TGGGAATAAT GTATATCTAA TGAGGCTGTG TTGGAATTGA ATGAGTTAAT
13751 GCACAGACCA GATTTGTCAT GTTGCCTGGC CCATAGGAGA CAATAAATGG
```

FIG. 3F

```
13801 TACCCAGTAT TAATAACTGT GAATGTCAAC AACATTTAAT ATATTGTATA
13851 TCTTCAAAAT GTACTTGAGG TATTTGTTCA TCATTCTGTT TTTGTTTGAA
13901 TAAGCTCGTG CCTTCTTTTT GTGAATATTT AAATTTATAA GTAGCGAGTG
13951 GGAGGGGAAG GAAGTTATGT GATGAGGCTA GCTTACTGAG CCATCTGCAG
14001 GCACCTTCAT TAGTCTTGAG ACTGTCCTCT GGTTACTTAA CAGCAGTGAA
14051 TTATCTAGAA TCATTTAGTG ATCAGAAGAC TTGGTTTAGT GGAATGTAGA
14101 TTTTTTTCTA ATAGACCCCT CTTCCAGGGA AATGTTTCAT ATTTTTGAAG
14151 AGGTTTCCTG GGAGTGTTT AAGAGGCCAT GATTGAAAAT GGGTGATTAC
14201 ATTAGTGTGT TTTCTATTCC TCCCCTTTTT GAGTTTCTGT TTTGGAATGT
14251 AAGCTTTGTT TTTCTACGTG GAGAAGGGTC CCTCAGCTGC TTCTGCCCAG
14301 GTTTTTTGAA TCTTCCTATA GGGATGGAGA TTTTCTTTGG GGACTGTTAG
14351 AGAAAATGGA ATAGAGTGTA GCTCTGAAGG AGAAGGATGT CTCCAGCAGA
14401 AGTACCTCTA GCCTTGGGCC AAGGGAGGGA AGGGAAGGGA ACGAGCATCT
14451 GGGAACCAGG GAAGGGATTT TTGTCTTTCT TAATTACTCT TACATCCCCA
14501 GTGCCCAAAA TAGTGTCTGG CATATGTTAA GTCCTTAGTA AATACTTGTT
14551 GAATGAGTGT ATGCTCAGTG AACAAAATAA ATGGCAAACA TTAAGCACAG
14601 TATCAGATAA TTTGTGTAAA AATATACAG CAGTGTTATA CTAAAACTTG
14651 CACAGAGGCC AGGTGCAGTG GCTCACGCCT GTAATCCCAG CACTGGGAGG
14701 CCGAGGTGGG CAGATCTTTG AGCTCAGGAG TTTGAGACCA ACCTGGGCAA
14751 CATGCTGAAA CCCTGTCTAT ACAAAAAATA CAAAAGTAG CTGGGGCATG
14801 GGGACGCACA TCTGTGGTCC CAGCTACTTG GGAGGCTGAG GCTGGAGAAT
14851 TGCTTGAAGC TGGGAGGTGG AGGTTGCAGT AAGCCAAGAT TGTGCCACTG
14901 CACCCCAGCC TGGGTGACAG AGTAAGACCC TGTCTCAAAA CACAAAACAA
14951 CACCCCCTTC AAAAAAAATC CAAAACCACC ACCACAACAA AAAAACTTAC
15001 ACAGAAAAGT GTTGATAATT GTCAAAATTG GCTGTTATT GGCAATTTGA
15051 CAGTAGCTGA ATTACTACCA TTTGAGCTAT ATTCACTATA GATAAGATCT
15101 TCAATATATT TACAACTTTA GTACTAATGG GAAAATGATA ACTTTTGAAA
15151 AGTTTTTTTT TTTTCTTATT GCAAACAATA CACAATACAA TGTTAAATAT
15201 AGAAGGTTAA ACGTGCATCT GAGTCTGTTT GGGCTGCGAT AATAGATACC
15251 TTAGACTTGG CAATTTATAA ACAATAGAAA TTCATTGCTG ACAGTTGTGA
15301 AGACTGGGAA GTCCAAGATC AAGGCGCCAG CGAATCTGGT ATCTGGTGAT
15351 GGCTCCTGC TTCAAAAATG GCGCCTTCTT GCTGCATCTT CACCTGGCAG
15401 AAGGGGCAAA CATGAGTCCT TCAGCTTCTT TTTTTTTTTT TTTCTATGTT
15451 TAAAACTTTT GGTCCGGCGT GGTGGCTCAT GCCTGTAATC CTAGCACTTT
15501 GGGAGGCCGA GGCAGGTGCA TCATGAGGTC AAGAGATCGA GACCATCCTG
15551 GCCAACATGG TGAAACCCCC CCGTCTCTAT ACTAAAAATA CAAAAATTAG
15601 CCAGGCATGG TGGCGTGTGC TTGTAGTCCC AGCTACTCAG GAGGCTGAGG
15651 CAGGAGAATT GCTTGAACCT GGGAGGCAGA GGTTGCAGTG AGCCAAGATT
15701 GCGCCACTGC ACTCCAGCCT GGCAACAGAG TAAGACTCCG TCTCAAAACA
15751 AACAAACAAA AAAACAAAA AAAACTTTT ATTTTAGGTT CATGGGTAAA
15801 TGTACAGGTT TGTTATGTAG GTAAACTTGT CTTGGGGTTT GTTATAGATT
15851 ATTTCGTCAC CCAGGTACTA AGCCTAGTAA CCAATAGTTA TTTTTTCAGA
15901 TTGTCTCCCT CCTCCCACCC TCTGTCCTCT AGTAGGCTCC AATGTCTGTT
15951 GTTCCCTTCT TAGTGTCCTT GTGTTCTCAT CCTTTAGCTC CCATTTATAT
16001 GTGAGAACAT GTGGTATTTG GTTTCTGTT CCTGCATTAG TTTGCTAAGG
16051 ATAATGTCAG CCTCTTTTTT TTTTTTTTT TTTTTTTGA TACAGAGTCT
```

FIG. 3G

```
16101 CGCTCTGTTG CCCAGGTTGG AGTGCAGTGG TGCGATCTTG GCTCACTGCA
16151 ACCTCTGCCT CCCGGGTTCA AGTGATTCTC TTGCCTTAGC CTCCTGAGTA
16201 GCTGGGACTA CAGGTGCGCA CCACCATGCC AGGCTAATTT TTGTATTTTA
16251 GTAGAGATAG GGTTTCACCA TGCTGGCCAC GCTGGTCTCC AACTCTTGAC
16301 CTTGTGATCC GCCGGCCTCG TCTTTTTCCC AAAGTGCTGA GATTACAGGT
16351 GTGAGTCACT GCACCCGGCC CAATGTCAGC CTCTTTTTA GGGAAGTGAT
16401 TTAATCACTT CCCTAAAAGT CCTACCTCGT TTTTTTTTT GGTTTTTCT
16451 TTTTTTTTT TTTTTTTTT TTTTTTTTT TAGGTAGAGT CTTGCTCTGT
16501 CACCCAGGCT GGAGTGCAGT GGTGCGATCT TGGCTCACTG CAACCTCCAC
16551 CTCCTGAGTT CAAGCAATTC TCCTGCCTCA GCCTCCTGAG TAGCTGGGAT
16601 TATAGGTGCC TGCCACCACG CCTGGCTAAT TTTTTGTAT TTTAGTAGA
16651 GTTGGGGTTT CACCATGTTG GCCAGGCTGG TCTTGAACTC CTGACCTCAA
16701 GTGATCTGCC CAAAATGCTG GGATTACAGG CGGGAGCCAC TGTGGCCAGC
16751 CCCTGCAAGT CCTACCTCTT AATAGTATTA CACTGGGGAT TACATTTCAA
16801 CATGAATTTT GTAGGGGCGA GGGGCACAAA CGTTTAGAAT ATAGCACATC
16851 ACATACATAG TGAGAGAAAA ATCCCTCAAA ATCTTACCTG AGACAATCAC
16901 TGCCAACAGA TTGCTGTATA GTGTGCCAAT TTTGTTTGTG TGTGTGTGTG
16951 CCTTAAAAAT ATTTATTATG GAAATTTAAA AACGTACCCC AAGGTGGCCA
17001 GGTGTAGTGG CTCACGCCTG TAATCCTGGC ACTTTGGGAG CCCGAGGTGG
17051 GTGTATTACT TGAGGTCAGG AGTTTGAGAC CAGCCTGGCC AAAATGGTGA
17101 TACCAGTCTC CTAAAAATAC AAAAATTAGC CGGGTGTGGT GGGCACCTGT
17151 AGTTCCAGCT ACTCGGGAGA CCAAGTCATG AGAATTGCTT GAACCCTGGA
17201 GGCAGAGGTT GCAGTGAGCC AAGACCATGC CACTGCACTC CAGCCAGGGT
17251 GACAGAGTGA GACTCCATCC TAGAAACAAA CAAACAAACA AACAAACCAA
17301 CTAACCAACC AGAGAAAACT CCCTGTCTGT AAGGAGTATG TGTTCTAATG
17351 GATACTGAGC CATCTTGTTC TGTTTAACAT GTGCCTAATG TTCTTTTATA
17401 TGGGCGGACT TGTAGGTTGT TTCAACTTTT CTGTTGATGA ACCTTTAGGT
17451 GGTTTCTGAT TATTTTGTG TTACAACAGT TTTCATCATT CACATCTTTG
17501 TATGCATCTT TTTTGAGCAC ATGTGCAAGT ATTTCTGTGG ACAATGGATG
17551 ATTCCTAGAA ATTGAAAGTT TGGATTACTG TGTTCCAAAA AAGGAAGCAA
17601 TACACCCAGC TATGTTGGCT TTTGCTCTTG GGTCCAGATG ATTATCTGAC
17651 AAAGTTATTC TCTGATTGCA TTTTCTTTTC TTTTCTTTTC TTTTTTTTT
17701 TTGAGATGGA GTTTCGCTCT TGTTGCCCAG GTTGGAGTGC AATGGCGCGA
17751 TCTCGGCTCA CTGCAACCTC TGCCTCCCAG GTTCAAGCGA TTCTCCTGCC
17801 TCAGCCTCCT AAGTAGCTGG CATTGCAGGC ATGCGCCACG ACACCTGGCT
17851 AATTTTTTGT ATTTTAGTA GAGATGGGAT TTCTCCATAT TGGTCAGGCT
17901 GGTCTTGAAC TCTTGACCTC AGGTGATCCA CCCGCTTCAG CCTCCCAAAG
17951 TGCTGGGATT ACAGGCGTGA GCCACAGTGC CTGGCCCTCT GACTGCATTT
18001 TCACAGTGTT TTGGGTCCTT ATCTCTACCT CAGTACCTCA ATATTCAGTG
18051 CCCACTGGGC CCTTAGATAC TGCAGCTAAA AGTGCACAGG GGTGGAGTGA
18101 TGTGACGGTT TTGGGGTCAC AGAAGCAGCT GGTATAGAGA GAAGTTGTGA
18151 AGTTTTTTT TTTTTTCCTG AGACAGAGTC TCGCTGTATC CCCTAGGCTG
18201 GAGTGCAGTG GCTTGATCTC GGCTCACTGC AACCTCTGTC TCCCTGGTTC
18251 AAGTGATTCT TATGCCTCAG CCTCCCGAGT AGCTGGGATT ATAGGCATGT
18301 GTCACCATAC CCAGCTAATT TTTGTGTTTT TAGTAGAGAT GGGGTTTCAC
18351 CATGTTGGCC AGGCTGGTCT TGAGCTCCTG ACCTCAGGTG ATCCGCCCAC
```

FIG. 3H

```
18401 CTGGGCCTCC CAAAGTGCTG GGATTACAGG CCTGAGCCAT TGCGCCTGGT
18451 CTTTTTTTTT TTTTTTAAG TAATCATAGG CTTGAATGTA GCCTCTCATC
18501 TGTTCACCTT AATAATCCAA AAGCCTTTAG ATAAAGAAAT GGAGATTTGG
18551 AATGGCTTCT CAGAATTCCA AGAGAGTATT GTCATGGTTT TGCCTGCAAA
18601 GCACCGTGGT CTGTCTCCTT GTGCAGTTGA GAAAGCTGGT GGTCGCCACT
18651 GACAGGCCCA GAGTTATTAA GTTGGACACT GCTTTAAGCA ACTTTGTAAA
18701 CAATCCAAGG CATACTAGAG AATTAGGAGA GATTGGCTTT GTGTATGAGC
18751 AATAACAAAA TCAAGTTCAA TCCAGCAAGT TTTTGGGGAA TTATAATTCA
18801 AAACTCAAAT ACTTGATCTG GAAGAAACTT GGAAAGAGGG AAGGAAGACA
18851 GGCTTGTTAC AGCATTGTCA GGGTAAAAGG AAAATACCGT GCAGCTTTTA
18901 ATTTTGCTTC TTCATGGCAT TCCCCATGTA GGTGCCCTAG ATTTGTTTTT
18951 TACAGTGGTC ACGACTTCAT GTGGATCCAC CCACCACTCT TGCCTGGTTC
19001 CCCAAGGGAC CAAGGGAAGG TGTATTCAGG ATGATTGCTG AAGTGAGGGG
19051 TGGGGTCTGT GGCTGAGAAG ACTCTCAATA CCGCGGCACT CATTATAAGC
19101 CTCTGACACA GGAGATTTCA ACTCCACCCG TGCAACAAAG GAACAGGGTG
19151 GGCAAGAGTA GTTACAGTTG CAGGCTGAGT GCGATGGTTC ATGCCTGTAA
19201 TCCCAGTGCT TTGGGAAGCC AAGGTGGGAG GATTGCTTGA GTCTAGGAGT
19251 TTGAGACCAG CCTGGGTGAC ATAATGAGAC CCTACCTGTA CAAAAAATT
19301 TTAAAAATTA GCCAGATTGG TGGTGTGCGC CTATAGTCCC AGCTACTCTG
19351 GAGAATGAGG TGGGTGAGGG TCCCTTGAGT CCAGGAGTTC GAGGCTGCAG
19401 TGAGTTATGA TTCTATGATT TCACCACTGC ATTCCAGCCT GGGCGACAGA
19451 GCAAGATTGT GTTCTTTTTT TTTTTGAGA CGGAGTCTCA CTCTGTCACC
19501 CAGGCTGAAG TGCAGTGGTA CGATCTCTGC TCACTACAAC CTGCACCTCC
19551 CAGGTTCAAG TGATTCTCTC CCTCAGCCTC CCGAGCAGCT GAGATTAAAA
19601 GCGGCCGCTT GTGTGCAGCT AATTTTGTA TTGTTAGTAG AGATGGGGTT
19651 TCATCATGTT GGTCAGGCTT GTCTTGAACT CCTGACCTCA GGTGATCCAC
19701 CCGCCTCGCC CTCCCAAAAT GCTGGGATTA CAGGCGTGAG CTACTGCGCC
19751 CAGCCATTTG TGTCTCTTAA AAAAAAACT AAGAAAATGA AAAAAATGAC
19801 ATTGGCCAAT TCATTAAAAT GCCACTCACT GACTGTGGTA TGAAATGGCT
19851 TTCCCTTTGA TGGACCGAGT CTGTCTCATT GTGTGAGCCA CTTGCAGGGC
19901 TGAGTATGAC TCTGGAATGT AGCTCCTAAC CTTATCTGCT GCCCAGCCAT
19951 TGAAATGGCC ATCCCTTCCA GTTCCCAGAA GATTCCAGTG TGTGTTTGGG
20001 ATTTTAAGAC AGTCTCTTGG TCTTCAGTGT GGCATCTTTC TGCCGGATTT
20051 TCCAGGATAA TTTTGATTAT AAGCATTGCA TTGCCCTTGG TGTGTAATGC
20101 CTGTGTATGA TGCTGTTCCC TTGTAACGTG CAGGATTAAA TTTTTGGGTC
20151 AGCCACTGCT GCTCCCTTC ATTCCTGCAG GTCATTAGAG TCATCGTACA
20201 TTTAGCGATG TCTCAGATCA GTGTATCTAG AGTGTTAATA AACATGTTAG
20251 ATTCCAAATC TACTGTCCAT TAATCCATA CTTCATACGT TGAGGATCTC
20301 TGACTGAAAG ATTAGACTTG GAAAATAAT AAGACTGTAT GGTAAGAAAA
20351 CTATAGTTGC AAATCCATTT GGACATGTAG TATGTCAGCC CTGCAGAGCA
20401 GATGTCAGAA CCCCATTTAG TTCTCTGAGT GCTAAGCCCT TCTGCCCACC
20451 ACGCTGTTTT TTTTTTTGA GATGGAGTCT CGCTCTGTCA CTCAGGCTGG
20501 AGTGCAGTGG TGTGATCTCG GCTCACTGCA AGCTCTGTCT CCCAGGTTCA
20551 CGCCATTCTC CTGCCTCAGC CTCCCAAGTA GCTGGGACTA CAGGTGCTCA
20601 CCACCATGCC CAGCTAATTT TTTGTATGTT TTTGGTAGAG ACGGGGTTTC
20651 ACTGTGTTAG CCAGGATGGT CTGGATCTCC TGACCTTGTG ATCCACCCGC
```

FIG. 3I

```
20701 TTCGGCCTCC CAAAGTGCTG GGATTACAGG CGTGAGCCAC TGCTCCTGGC
20751 CCCCACGCCT TTTTTTTTTT TTGGAGACAG AGTTTCACTC TGTCACCCAG
20801 ATTGGAGTGC TGTGGCACAA TCTCAGCTCA TTGTGTCCTC TGCCTCCCAG
20851 GTTCAAGTGA TTCTTGTGCC TCAGCCTCCT GAGTAGGTGG AATTACAGGC
20901 GTGCACCACA ACACCTGGCT AATTTTTGTA TTTTTAGTAG AGATGGGGTT
20951 TCACCATGTT GGCCAGGCTG GTCTCGATCT CCTGACCTCC AGTGATCCAC
21001 TTGCCTAGGC CTCCCAAAGT GTTGGGATTA CAGGCGTCAG CCACCATGCC
21051 TGGACCCCTC TGCCCCTTTA AGCACTGCCA CATATTAGAT CTACGAAGGC
21101 TTTATGGATA CAATCCAAGG AAGATGAACC TTGGGCTAGT GGGATAAAAC
21151 TAAGCGCATG TAGTTAGAAT GGAATGATCT GGAAACCAGG TCCCAAGTTG
21201 GTCTAAATTA GACTCATGTT GACTATGTCA CACTGTAAAC CAGTCTAAAT
21251 GCTAATAAGC ATGCTTGACC AAACACTGCC CTGCAGCCTT CAGAGAGGAA
21301 GAAGGAAAAC ATAATTTGTA TCCTCTCTCC CTATTTTCTG AGTCTATGGG
21351 ATTCAAATTG TAGCTGCCAT GGAAACTGTA CTTTGGAATT TCTAGAGCCC
21401 TTAATTTTAA CTTAACATAT AAAAACACTT TTGTACTGAT TTTATAATTA
21451 TTCATGATGG ATGAGAAAGT GAATGTCTTT GACAGTGAGG GAAGCTATCC
21501 GAATGCTATT TTCTTTTTTT TTTTTCTTTC ATAAAGATGC ATATATTTGC
21551 ATGCTTTATT TACCTGGGGC TAACTCTTGC ATCTTTTGCA GATTCCGACA
21601 CCATAGCTGA GTTACAGGAG CTCCAGCCTT CGGCAAAGGA CTTCGAAGTC
21651 AGAAGTCTTG TAGGTTGTGG TCACTTTGCT GAAGTGCAGG TGGTAAGAGA
21701 GAAAGCAACC GGGGACATCT ATGCTATGAA AGTGATGAAG AAGAAGGCTT
21751 TATTGGCCCA GGAGCAGGTA GGAGGATTTT AACATCATGC TTTTCCACTT
21801 TCTGTACCGG AGTGTTCATT GCAAAGACGA TAATCTGCTG CACTGGCGTC
21851 TAGGATCAAG CACGTTTTCC TCTGTGACTC TATATTTAAT TATAGTTGGG
21901 GCAAAAAGGT CTCTCATGTT CTTAGCTCAT CTTCTTGAAC TGATGTTGGC
21951 TAATTTTGAA GGCTCACAAA TTCCTCTTGA TGTATCATGT TTCTATCGTT
22001 GTAATTTATT TCAGAACCAA GGTGGCCTTT TAGCTAATGA ATTTAAGATG
22051 ATCTTTTATG ACCATTAGCT GAGGACTCAG GATATACATA TGGTGGGGTG
22101 AATCAGATTG CTTTTGTACA CGCTTTAGGT ATTTGTGTTG TGGGCATATG
22151 GATTTGGTTT TAAAACAGGC CTTTGAAGAA ATCAAATAAC ATTCTTTGTT
22201 ATGTGGCTAG GGAGTTGCTT GTTTGAGAGC AGGTAGAACG TTATCTTTTT
22251 TGTTGTGGTA TTTTTCTTTC TTTTAAACAA GGCTACTGTC TCTAGACATA
22301 TTGATTCATT TGCTGTGTTT TAGAGAGATG GCCGTCAGCC TTGGAATTCA
22351 GAGAGTAATT TATTACTTAC AGACATTTTA GTGCACATGA TATGTCTGAT
22401 AATGTACCCA GCTCTGCAGG AAGCTTGCAA AAGGAATAGA AGTCCCATGG
22451 TTGCTATTTT CAGTGTTTAA AAACAACCTT GGAAAGTGGA GGAAAAATGC
22501 AAATGTATAA AGCAGGTGCT TACCAGCTAA AGTATCACAG AAGTGGGAGA
22551 GCAATTAGCA AATTAATTAA CGATGATGTG AGGGGAGATG TTGTGGGTGA
22601 GCAAGGGACA GTTAGGGACA GTTCTCACCG ATGGGGGGAA ATGTAGGTTC
22651 TCGGCAGAGA GAAGTGATGA AACATGTTG GGTAGAAGTG TGACATTCTG
22701 GAGTACTAGA ATGCTATGCA AGTGTGTGTG TGTGGGTGTG TGTGTGTGTT
22751 CAGTGGTTCA GAACAGACTG GGAAATGGCG AAATGAGGAC ATTTGGGTGG
22801 GGAGGGGAA ATGGGTGGGA AACTCAAGAA CCTTTTTTTA AAAAATTGTG
22851 GTAAAATATA TATAACATAA AGTGTACCAT TTTAACCATT TTTAAATGTG
22901 CAACTGAGTG GTATTCAGTG CATTCATGAT GTTGTACAAC CATGACCGCT
22951 CTCCATTTCT AGAATTTTTC TATCATCCCA AACAGAAACT CTCTATCCAT
```

FIG. 3J

```
23001 TATACAATAC CTCCCCATTC CCCCAAGAAC CAGTTTTTGA ATTGCAGTTT
23051 ACTTTGTGAG GCTGTTGGGG ATTATTTAGG CCTCTGGAAG GAGGAGGTTG
23101 GGATCAGAGT CTGGCCCTGT GGACTTCAAT GACTTTGTGT GGCCTCCAAT
23151 CAGAGAAGCA GCGGAGGGCA GGAAGCTGCT TGTCAGAATC TGAGAGTGAT
23201 GTGGCTTCTT TGTTTAGCAA TAAAATGTGA GCACATAATA GAAAGGAAAA
23251 GTGACAGGAC ATGGCAGATA ATTTGGAAGA GAGGAGTGGA AGATGCTCAC
23301 TCAGCCTCCC AGCTCCTGAG AAAGAACTGT GTCTCATCAG TTCATACTAC
23351 CTGAGCATCT GTTGTATCTG GTGTGTTTCT AGGTCCTGGA GAAGAGGCAT
23401 TACGTGTAGC CCTGACCTTG TGATGCTTAT GTTTTTGATG GGAAATAGTG
23451 CGTGTAAAAA GAAAATAATC AACAGGCCA CACGGCAGGC AAACAATAGA
23501 GATATTCAAA TAGGTATACC TTCCTCCAGG TGAATGGCCT GAAATGACCG
23551 TGTGGAAGTG TGGGCTGGGG GCTTATAAAA TTATACACAT ACAGGCGCTA
23601 ACTAAAGCCG CCTATTCATT CCTTAAGAGG ATGCATAGAA AAGAAAGTA
23651 GGGTCCTTAA CTGAGCCATT TGGAATTTAA GGGCATGAGA GAAGCCAGCA
23701 CAAGCAGTGA AGGGAAGGAA AAGAAGTGCC CGAGAGGAGG GAGGGATGCT
23751 GTTCTGCAGA CAAGGCCTGC CGCCTGGGAG AGGCCCGCAC GCCCACCCAG
23801 GGTTCTCTGA CAGCTGGAAG GGGTCTTCAG AGACTGTTTA TATTTATTT
23851 ATTTATTTAT TTATTTATTT TGAGACAGAG TCTCTGTCAC CCAGGCTGGA
23901 GTGCAGTGGT GCGATCTCAG CTCACTGCAA GCTCCGCCTC CCAGGTTCAC
23951 ACCATTCTCC TATCTCAGCC TCCCGAGTAG CTGGGACTAC AGGCGCCTGC
24001 CACAATGCCC GGCTAATTTT TTTGTAATTT TAGTAGAGAC GGGGTTTTAC
24051 CTCGTTAGCC AGGATGGTCT TGATCTCCTG ACCTCATGAT TCGCCCACCT
24101 CGGCCTCCCA AAGTGCTGGG ATTACAGGTG TGAGCCACTG TGCCTGGCCG
24151 ACTGTTTCTA CTATTTAGA GAGAGGGTCT CACTGTCATC TGTGCTGGAA
24201 TGCAGTGATG CAGTCATAGC TCACTGCACC CTCAAACTCC TGGGCTTAAG
24251 CGACCCTCCC GCCTCAGCCT CTTAAGTAGC TGGGACCATA GGCATGTGCT
24301 GCCACACCCA GTTAACTTTA TTATTTATTT ATTTATTTAG AGAATGAGTC
24351 TCATTCTGTT GCCCAGGCTA GAGGTGCAGT GGCACGATCT CGGCTCACTG
24401 CAACCCCGCC TCCCAGGTTC AAGCGATTCT TCTTGCTCAG CCTCCTGAAT
24451 AGCTGGGATT ACAGGCACCT GCCACCACAC CTGGCTAATT TTTGTATTTT
24501 TAGTGCAGAG GGGGGGTTTC ACCATGTTGG TCAGGCTGGT CTCGAACTCC
24551 TGACCTTGTG ATCTGCCTGC CTCGGCCTCC CAAAGTGCTG GGATTACAGG
24601 CGTGAGCCAC CGTGCCCGGC CCACTTTATT ATTTTAAAAA CATTGTTTTA
24651 TTTTTATTTT TTTGAGACAG AGTCCGCTGG AGTTCAGTGG CCGGATCTCA
24701 CTCACTGCAA CCTCTGCCTC CTGGGTTCAA GTGATTCTTG TGCTTCAGCC
24751 TCTCTAGTAG CTGGGACTAC AGGCGGGTGC CACCATGCCT GGCTAATGTT
24801 TTTTGTATCT TTTTAGTAGA GACGGGGTTT TGCCATGTTG GCCAGGCTGG
24851 TCTCGAACTC CTGACCTCAA GTGATCTGCC CACTTTAGCC TCTCAAAGTA
24901 CTGGGATTAC AGGCGTGAGC CACTGTGGCT AGCCCCAGC TAACTTTAAA
24951 AAAAAATTTT GTGGGCCGGG TGCAGTGGCT CACGCCTGTA ATCCCAGCAC
25001 TTTGGAGGCC AAGCAGGGCG GATCACTTGA GGTCGGGAGT TTGAGACCAG
25051 CCTGACCAAC ATGGAGAAAC CCTGTCTCTA CTAAAAATAC AAAAAATTAG
25101 CCGGGTGTGG TGGTGCATGC CTGTAATCCC AGCTACTTGG GAGCTGAGGC
25151 AGGAGAATTG CTTGAATCTG GGAGGCAGAG GTTGCAGTGA GCTTAGATCA
25201 CGCCACTGCA CTACAGCCTG GCAACAAGA GCGAACACTC CGTCTCAAAA
25251 AAAAAAAATA AATTATGTAG AGGTGGGATC TCCCTATGTT GCCCGGACTG
```

FIG. 3K

```
25301 GTCTTGAACT CCTGGCCTCA AGTGATCCTT CCATCTCCCC CTCCCAAAGT
25351 GTTGGGATTA CAGGCATGAG CCACCCCTCC TGGCTGAGAC TGCTTATTTT
25401 ATTTATTTTT AATTTTTTTT GTTTTGAGAC TGCTTATTTT AATGGAAGCT
25451 TCAGGGGTCA GACGGGGTCA GACAGAGTCA TTGGTGAGCA AGCAAAGGTG
25501 TAGACTGTTC AGTTCAGCCT TCCTTGGACA CCTTTTATGT GCCAGACAAA
25551 AGAAGGATCA GCATATCAGG TGCAGTAAAT TATTGGGGTT ATGTTGGTGT
25601 TTCCCAAATG TGTTAGATTT ATCCCTGGTA GTGTTAAATC TCATGATTTT
25651 AGGTAGTATA TGGACAACCT ATGTAAAAAC ATTTAATAGT TTAATATTAA
25701 CTAGCATATC AAAACCTGTG ACTTTGCTCA CGCCTGTAAT CCCAGCACTT
25751 TGGGAGGCCA AGGCGGGAGG ATGGTTTGGG CCCAGGAGTT TGAGGCCAGC
25801 CTAGGTAACA TGGTGAGACC CTGTCTCTAA ACAAAACAA AACAAAACAA
25851 ACAAACAAAC AAATAAACAA ATCCCTGTA ACTTGTTCTA CAATAACCT
25901 AAACAATTTT TTATTTAAAA TTAAATAAAA AAATTGAAAC AGTAACCATT
25951 TTTTTTTTT TTTTGGAGA CAGAGTCTTG CTTTGTCACC TAGTCTAGAG
26001 TGCAGTGGCA CAATCTCTGC TCACTGCAAC CTCTGCCTTC AAACAATTCT
26051 CCTGCCTCAG GCTTCTGAGT AGGTGGGATT GATTACAGGT GCACTCCACC
26101 ATGCCCAGCT AATTTTTGTA TTTTAGTAG AGACGGGGTT TCACCATGTT
26151 GGCTAGGCTA GTCTTGAACT CCTGACCTGC AGTAGTCCAC GTGCCTTGGC
26201 CTCCCAAAGT GCTGGGATTA CAATCACAAA TTTATAGAAA AGTTGCAAGT
26251 ACCATGTAGT CAGGGTTCTT AAGAGAAATG GAACCAGTAG GAGATAGATA
26301 TATAATCATC TCCTAGGATT ATAAGTTGAC ACATAAGACT AACCGTCACA
26351 TACAGTATAA ACAACTTTTT TTCTTAAACC ATTTGATAGA TACACACACA
26401 CTGATATACA TAGAATATAT ATACACACAC ACAGAATGTA TATACACATA
26451 GAATATATGT GCATACAGAA TATATACACA GAAATATATA TGTACACATG
26501 CATAGAATAT ATTTACATAT ATATGCATAT ATATAATTTA TTTATTTTAA
26551 GCAGTTGATT TATACAGTTT TTGTTTTGT TTTTTTTTG AGACAGAGTC
26601 TCACTCTGTC ACCCAGGCTA GAGTGCAGTG GCGAGATCTC AGCTCACTGC
26651 AACCTCTGCC CCGGGTTCC AGTGATTCTC CTGCCTCAGC TCCACAAGTA
26701 GCACACCACC ATGCCCAGCT AATTTTTGTA TTTTTTTTAG TAGAGACGAG
26751 GTTTCATCAT GTTGGCCAGG CTGGTCTCGA ACTCCTGACC TCAAGTGATC
26801 CGCCCGCCTT GGCCTCCCAA AGTGCTGGGA TTTCAGGCGT GAGCCACCAC
26851 ACCTGGCTCC CATAATGTCT TTTAGAATAA AACGATCGAG TTGAGGATCA
26901 CACGTGACAC TTAATTGTCC TGTCTCTTTA GTCTCCTTCA ATCTGGAGCA
26951 GTTCTTTGAT TTTTCCTGGA CTCTCATGAC CTTGACAATT CTGATGATTA
27001 TAGGCCAGTT ATTTTGTAAA ATTTGAATTT GTCTGATGTT GCTTATGTTT
27051 AGATTTAGGG TCTTGGTCTT TGGCCGGAAT ATCTCAGACA AGATGCTCTG
27101 TTCTTATTGC ATCAGAGCAG AAGACTCTCT GTTTCAGTTG ATCACATTTA
27151 TGTTGATGCT CACTTTGATC ACTTGATTAA GGTGGTGTCA GTTATGCCTT
27201 TCTACTTGTA GGGTTACTCC TTCCTCCTTC GTGATTTTAT TTATTTTATT
27251 TTTCTTAGAG ACAGGGTCTT GCTTGGTTGC CCAAGCTGGA GTGCAGTGGT
27301 GGGATCTTGG CTCACTGCAG CCTTGAACTC CTGGGCTCAA GTAATCCACC
27351 TGCCACAGCC TCCTGAGTAA CTGGGACTGT AAGCGAACAC CACCACACCC
27401 AGCTACTTTT TGTATTGTAG AGATGGGGTC TCACTGTGTT GTCCAGGCTG
27451 GTCTGTAACT CCTGGCCTCA AGCAGTCTTC CGGCCTTGGC CTCCCGAAGT
27501 GCTGGGATTA CAGGCATGAG CCACTGCACC CAGCCTCCTT TGTAATTAAA
27551 AAAGTATTTT ATGGGGAGTT ACTTTCAAGT GATGGAAATA TTTTATATCT
```

FIG. 3L

```
27601 ATGTGGACTT GGATTTTCCT ATTTCAGTCA GTGAGTTATA ATCCATTTCT
27651 GTCACTAGTT TTATACTTAA ATTGTTCCCA ACTTGGCCAC TGAGAACCTT
27701 TTTAGGTTAG CTTTTGTGTC CTTTTCACAT GTCTCCAAGA TTCATTGAAT
27751 ACTTTCCTGC TTTCTGGTAT AGCAAGATGT TCAGGTTCTT TTGGTACTTT
27801 TACTTTCTCT GCCCTGGCTC TGGCATCAGT CATTTCTCAG AGGAGCCCTG
27851 TGCCTTTCAG TGGACAATGG TGTTTAGAGG CCAAGATCTG GACATTGGGT
27901 GTTTTCATTG CTACCGGTGT GTCACTACTC CCAGACCCCT TCAGTGGAC
27951 AGCACTAAGG AATACACATA CGTATATACA ATATATCCAC CTACACATGT
28001 GCGTGCACTC ACACACACAC ATATACATTA CATCTATATT TGTGTATCCA
28051 TGTCTATATA TTGAAAATTG TGGCTGGGCA CAGTGGCTTA TGCCTTTAAT
28101 CTCAGCATTT GGGAGGCTG AGGCAAGAGG ATCACCTGAA GCCAGGAGTT
28151 CAACACCAGC TTGGGAAACA GAGAGAGACT CTGTCTCTAC AAAAATAAAA
28201 AGGGAAAACC ATGAGTTCAC ACCCGTGCCC CCAGTTCCAA TCCAACTTCA
28251 CAGGGTTCAT TTTAGTTTTC ACCCTTTCCA TGTTTGTAAT TCTCTTCTCT
28301 GACATTATAC CCTTAATATG TTTACTTATT TTATGCATCT GTATGCATCC
28351 AATCTACTGT CTTTGTTGGT ATCCCACCTC CCCTTGGTGG GTCCAGATAA
28401 TCTGCTCTGG GTTGCCCTTT CACGTGGATG TCTTCCTTAC CCTGTGTGGG
28451 CCTGTGATAC TGGGCTGCCC CCACACATGA GTGCTGCCCT CCTCACGTTG
28501 CTTGGGACGG CACTGTGTCC TGGGCCACCA TGACTTTTCT CATAACTAGC
28551 GTGGATGCTT ACCTTGTTCC ACACCAGTGA ATGGCTTCAG GAAGAGAAGA
28601 GGAAGAGAAA AATATTTACA TTTAAAGAAA GGTAGTTTAA AGAAATATGT
28651 TAGGTAAAGA ATTGAGCAGG TAATATACGG AGCTGGCAAA AATTGTGACC
28701 AAAGTAGGTG AATGATTGAG ATTTATGCAA TTCTGGGCTA AGTGACAGCC
28751 CCTTCCCTTT CCCTTCCCTT CCCCTTCCCT TCCCTTTTCT TCCCTTTCCC
28801 TTCCCTTTCC TTCCCTTTCC CTTCCCCTTC CCTTCCCTTT CCTTCCCTTT
28851 CCCTCTTCTT CCTTCCTTCC TTCTGTTTTC TTTTCCCTTC TTTCCTTTGC
28901 CTTTTTTTTT TTTTAAAGC TAGAAACATC AGTTTAGGCA TAAAGACAGA
28951 GGAAAAGGCT TCTTTTTCCT CTCACAGTTC TTTATAATTG CTAAGCAGT
29001 TTCTTTTTTC CCTAGGTTTC ATTTTTTGAG GAAGAGCGGA ACATATTATC
29051 TCGAAGCACA AGCCCGTGGA TCCCCAATT ACAGTATGCC TTTCAGGACA
29101 AAAATCACCT TTATCTGGTG AGTCTTTACA TCTGTCTCTC TGGAATTAGC
29151 CTAGCACTCT GACACTCAGA TGCCTGTGGT AGAACTGAAT GTTGTTCTTG
29201 CCCATGTGGT CTCATTCATG CAAAGACTTT CTTACCTTAC AGGTGTCTCC
29251 CTGGTTTCCT CGTTATAAAG ATCAAGAGCT AACCCATTTA GAAACAGCCT
29301 CATTGGGCTG AACGTGGTGG CTCACGCCTG TAATCCCAGC ATTTTGGGAG
29351 GCCGAGGCGG GTGGATCACG AGGTCAGGAG ATCAAGACCA TCCTGGCTAA
29401 CACAGTGAAA CCCCGTCTCT ACTAAAAATA CAGAAAATT AGCCGGGCAT
29451 GGTGTCGGGT GCCTGTAGTC CCAGCTACTC AGGTGGCTAA GGCAGGACAA
29501 TCGCTTGAAC CTGGGAAGCG GAGCTTGCAG TGAGCCGAGA TTGCGCCACT
29551 GCACTCCAGC CTGGGTGACA GAGCAAGACT CTATCTCAAA AAAAAAAAA
29601 AGAAAAAAAA AGAAACAGCC TCATTGACAG TTGGATATTG TAGCTGTGGC
29651 TTTCAGGCAA TAATAGGGAA TCATTTATTG GGGAATAGTC TGTCATTATG
29701 TATAAGATAA TCTTGCTTTA ATTTTAAAA ACTTCCTGTG TTAGCTTGCT
29751 TAGGATTAAA AAAATGATAA TAGTGCATGG TTGTTATAAG AAAATGCAAA
29801 CACTGCAGAC ATGCATGAAG TTGAAGGGAA AGCCCCCCAT TTTCTTTTCC
29851 TTTTCTTTTT TTTTGAGACA GAGTCTCGCT TTGTCACCCA GGCTGGAGTG
```

FIG. 3M

```
29901 CGGTGGCACT ATCTCGGCTC ACTGCAATCT CCACCTCCCA GGTTCAAGAG
29951 ATTCTTCTGC CTCAGCTTCC CTAGTAGCTG GGATTACAGG CACGTGTCAC
30001 CACGCCCAAC TAATTTTTGT ATTTTTAGTA GAGATGGGGT TTTACCACGT
30051 TGGCCGGGCT GGCCGCAAAC TCCTGACCTC AAATGATCCA CCTGCCTCGG
30101 CCTCCCAAAG TGTTGTGATT ACAGGAGTGA GCCACTGTGC CCGGCCTCTC
30151 CGTTTTATTT TCTAATCCTC CTCCCTAGGG GAAGAAATGT TAAATGGTTA
30201 CATAAGCTTT CCCTTTCTGA CCCTTAACTG TGCTCTGTAG GAGCATGGTG
30251 GGGGATGTTT CTTTTCTTTT CTTCTTTTTT TGAGACCAGG TCTCACTTTG
30301 CCACCCAGGC TGGAGTTCAG TGGCATGAAC ATGGCTCACT GCAGCCTCGA
30351 CTTCCTGGGC TCCAGCAAAC TCCCACCTC AGCCTCCCGG GCATACACCA
30401 CTGTGCCTGG CTAATTTTTG TATTTTTAGT AGAGACGGGG TTTTGCCATG
30451 TTGCCCAGGC TGGTTTCGAA GTCCTGAGCT CAAGAGATCT TCCTGCCTTG
30501 GCCTTCCAAA GTGCTGGGAT TACAGGTGTG AGCCACCATG CCCAGCTCCG
30551 GTGGGGGATA TTTCTATATC CACATGTGTA TAGTTTACTT TATAAAAATG
30601 GTATGTTACT CTGTGCTTGG CTCTCCAGCT TGCTGTTGCC TTTCACCAGT
30651 GTATCCCAGA CATCCTTTCT TCCTTGTCAG TAACGCAGGT CTACTTTATT
30701 CTTTGAGCAG TGGCATAATT TTCCCTGATG TGTATATATC ATAAGTTAGA
30751 GAATGCTAAA ATTCATTTTG GGCCTTGTT TAGGTTCTTG AGGGATTAAA
30801 TTCCTAAATT TAACAAGTGT ATCCTGGAAA CAATTTTTGT TCCTGATTCA
30851 GCCCTTAAAA GAGGACTATC ATGTTACCTT GAATGGAGAT AAACAGGCTC
30901 ACGTAAGAGA AAAGGGTAAG AGGGATGAAC TCCCACTTAT CTTAAACTTC
30951 TACTGGCCCG TTTTTGGGGA ATTTGCTGCT TTTATTCCTG ACCTAAAATA
31001 AATAAGTTTA TGTGTCTTGG TTTCATATTA GTTGAGAACC CAGTGCCTGG
31051 AGAGAAGTTT TCCTTGTCCT CTGAGTGAGG ACATTCACAT ATGAATCTAT
31101 TGGCAGACTG GCTTTGACTG ACCACACGTG CCTTCAGAAC CAATGCCACA
31151 GCTCTTAGGT TTATGGCCTG AAACACCCTT TCCTTACATA TTGCCTTAGA
31201 AACTTTCCTT CCTTGAGACA TGGGGCATGG AACCCTCACC TTCACAGATG
31251 ACCTTGGTGT GTTTCTAGGG TTGCTGGTGT TCCAGGACAT CTGTTGCAGA
31301 TGCAGTATTT ACCTTGTGCT CTCTGCATCA TAAGCAGCTT CTCATGTTTG
31351 AATGTATTAA CAGACTTTTA ATTTTTTTA TTTTGAGAC AAAGTCTCAC
31401 TCTGTCACCC AGGCTAGTGT TACCCAGGCT GGAGTGCAAT GGCTCAATCT
31451 CAGCTCACTG CAACCTCCAC CTCCTGGGTT CAAGCGATTC TCTTGCCTCA
31501 GCCTCCCGAG TAGCTGGGAT TACAGGTGCA TGACACCACG CCCTGCTAAT
31551 TTTTGTATTT TTAGTAGAGA CGGGGTTTCG CCATGTTGGT GGGGCTGGTC
31601 TCAAACTCCT GACCTCAGAT GATCTGCCCG CCTTGGCCTC CCAAAGTGCT
31651 GGGATTACAG GCGTGAGCCA CTGCGCCTTT TCTTTCATT TTTTTTCTGA
31701 GATGGAGTCT TTCTCTGTCA CCAGGCTGGA GTACAGTCAT GCAATCTCAG
31751 CTCACTGCAA CTTCCACCTC CTGGGTTAAA GTGATTCTCC TGTCTTAGCC
31801 TCCTGTGTAG CTGGGACTAC AGGCGTGTGC CACCGTGCCC AGCTAATTTT
31851 TATATTTTTA GTAGAGACGG GGTTTTGCCA TGTGGGTTAG CTGGTCTTG
31901 AACTCCTGAC CTCAGGTGAT CCACCCGTCT TGGCCTCCCA AAGTGCTGGG
31951 GTTATAGGCG TGAGCCACTG TGCCCAGCCT CAGGCTTCTT TATTAAGAAG
32001 AAGTTCGGGC CAGGTGTGGT GGCTTACACC TGTAATCCCA GCAATTTGGG
32051 AGGCCGAGGT GGGCAGATCA GGAGGTCAGG AGATCGAGAC CATCCTGGCT
32101 AACATGGTGA AACCTCGTCT CTACTAAAAA TATAAAAAAT TAGGCAGGTA
32151 TGGTGGCGGG TGCCTGTAGT CCCAGCTACT CGGGAGGCTG AGGGAGGAGA
```

FIG. 3N

```
32201 ACGGTGTGAA CCTGGGAGGC GGAGCTTGCA GTGAGCCCAG ATTGTGCCAG
32251 TGCACTCCAG CCTGGGTGAC AGAGCGAGGC TCCGTCTCAA GAAAAAAAAA
32301 AAAGACGTTC CCTTGAAACA ACAGGGCTTT TGTTTGTTTT GGTTTGTGTT
32351 TGTTTGTTAT TGTTGTTTTA GATACGTATT TTTTTCTTTC TTTTTTTTTT
32401 TTAAGTGATG ATGTCTCTGT TGCAGTGGCA TGATCATAGC TCACTGTAAC
32451 CTCAAATTGC AGGGCTCAAG TGATTCTCCT GCTTCACCTT CCTGATTAGC
32501 TGGGACAACA GGTACAAACC ACCATGCCTA GCGAATTTTT AAATTTTCA
32551 TAGAGACTAG GGTCTCACTA TGTTGCCTAG GCTGGTTTCG AACTCCTGGC
32601 CCCAAGTCAT CCTCCTGCCT TGGCTTCCCA AATTGTTGGG ATCACAGGCA
32651 TGAATCACCA CACCCAGCCT ATTTTAGAT ATTTTAATTC GAGCTCTACA
32701 GGAGGTTTAG AACACTAGCT TGTGAAGATA ACTTCATTT TCAAGGCCAC
32751 ACAGAATCTA AGTGGTCCTG GAATTAGGAA GGGCTTTGAT TTTTTGGACC
32801 AAAGTTGAGA GTCCACAGTT TTCTGGTCTA CCTTGCACTG CTCCATAAAC
32851 TCATATTTCT TTTCTCTGAG CTGAAGAGCT CCCCTTCTTG GTGTCTAGTC
32901 TCAGGCAACT TATTCTTAAA AGTAAGCATT ATTGAAATGC TTTGGGATTT
32951 TCACATCATC AAGGTCCATT TTGGTAGAGG CACTGACAGA TTTTGAGTGT
33001 TCTGTGTGAA GGAACTCAGT TGAGGATTTA GTGGTCCATG TGGCAGGCTA
33051 CTGCTCAGTA GCTTCAGGGA AACCACTGCT TGCCTCCCCT GTGGCCAGTG
33101 AGGATGATCA GAGGAGTCCC AGCAGGAATG CCCAAATGTA GTTTTCTTAC
33151 ATGTTGATGG GAGTGCATTG TTTCATGTCT AAACAGTTCT CAAATCACAT
33201 CTTCAGGAGG GTACTATCTG GGCACTTTGA TAATTTCTCA CTTTGATGTC
33251 ACCGTTCTTA TTACCATCAC CTAGTTTTGT CATAGTAGAA ATAACTTTCC
33301 TTTTTCTGTG TGTGTGTGTG TGTGTGTGTG TGTGTGTGTG TGTGTGTTTT
33351 GAGATGGAGT CTTGCCGTGT TGCCCAGGCT GTAGTGCAGT GGCGTGTTCT
33401 CGGCTCACTG CAACCTCTGC CTCCGGGTT CTCCTGCCTC AGCCTCCCGA
33451 GTAGTTGGGA TTACAGGCGT GTGACACCAC GCCCGGCTCA TTTTTGTATT
33501 TTCAGTAGAG ATGGGGTTTC ACCACTTTGG CCAGGCTGGT CTTGAACTCC
33551 TGACCTTGTG ATCCGCCCAC CTTGACCTCC CAAAGTGCTG GGATTGCAGG
33601 TGTGAGCCAC CACGCCTGGC TTTTTTTTTT TTTTTTTTGA GACAGAGTCT
33651 TGCTCTGTTG CCCAGGCTGG AGTGCAGTGG CGGGATCTTG GCTCACTGCA
33701 GCCTCCACCT CCTAGGTTCA AGCAATTCTT CTGCCTCAGC CTCCTGAGTA
33751 GCTGGGATTA CAGGTGCCCA CCACCATGTC CGGCAAATTT TTGTATTTTT
33801 AGTAGAGACA GGGTTTCACC ATGTTGGCCA GGCTGGTTTC TAACTCCTGA
33851 CCCCAGGTGA TCCGCCTGCC TCAGCCTCCC AGAGTGATGG AATTACAGGC
33901 ATGAGCCACT GCGCCTGGCC ACCTTTGTCT TCTTAGTTGT GGATTTAACT
33951 GCTGTGGACA TCTGCTTGGG CATAGCCTTC CCGGAGTACC TCTTGGATTG
34001 GGACTGTCTG TGGGTTTCTG TGCTAGGACA GGCTCCCAGA TGTAGGAGGC
34051 TTCCCCAATG ATCTCACCAC TGGCATCGGC ATCCTTAGCT TCTACTCAGC
34101 TTTTCCATCT GCCATCTTGC AAGATGGAAG GTTGTTTTGT TTTTGTTTTT
34151 GTTTTTTGGT TTATTTTTTT TGAGATAGAG TCTCGCTCTG TTGCCAAGGC
34201 TGGAGTTCAG TGGCGCAATC TCGGCTCAGT GCAACCTCCA CCTCCTGGGT
34251 TCAAGTGATT CACCTGCCTC AGCCTCTGGA GTAGCTGGGA TTACAGGCGC
34301 GTGCCACCAT GTTCGTTTAA TTTTTTGTAT TTTTAGTAGA GACGGGGTTT
34351 CACCGTGTTA GCCAGGATGG TCTCGATCTT CTGACCTCAT GATCCGCCTG
34401 CTTCAGCCTC CCAGAGTGCT GGGATTACAG GCGTGAGCCA CCGTGCCCAG
34451 CCTAGGAGGG TTCTTAATGC AGCTGTTTTT TGGAGTTCTG GTTGCCTCAG
```

FIG. 30

```
34501 CACACTGCTA CTTGGGTCAA TGACATTTTT ACTCCCTTGT TTTGTAGCTC
34551 AATTGGGTAT TACTGATGGG ATTTTGTAAT TATTAATATT TTCTTGTCTC
34601 CATTTTCTTC TCAAGTACTT TGTTGCTTTT GAGTAAAATG CTTGCTAAGG
34651 GTATAGTTTT CACATAAAAG CTCAAATTTA GCATGGAAAT TAAGATATGC
34701 TCATACGTCT GCCATCCCTT ATCTGTAATT CTGAAATACC TAGAGTTCTG
34751 AATAACCTCA AATTCTTTTG TTACTTGTTT ATCAGCAAAA CCTGATTTGA
34801 ACTCAGTTTT TGGCAAAACT TGATCCAAGC TCTCTTAAGG CTCTTTTTAG
34851 TCTTTATTCA TTCCCTTTAG TGTGACTTCC CATTTTGCTA TAAAATTATG
34901 AGTGTGTTTG ATTACAAGGT GATGTCCCAG ACCCTACTGA GGGTGTTACA
34951 TAATATAAAC TGTATGTATG GCTGGGCGCG GTGGCTTATA CCTGTAATCC
35001 CAGCACTTTG GGAGGCCGAG GCGAGCGGAT AACCTTAGTT CAGGAGTTCA
35051 AGCCCAGCCT GGCCAACATG GTGAAACCCC GTCTCTACTA AGAATACAAA
35101 AATTAGCCAG GCATGATGGT GGGCGCCTGT AATCCCAGCT ACTCCTTAGG
35151 CTGAGGCAGG AGAATCACTT GAACCCAGGA GGTGGAGGTT GCAGTGAGCC
35201 AAGGTCATGC CACTGCACTC CAGCCTGGGC GACAAAGCAA GAATCTGTCT
35251 CAAAAAAAAA AAAAAAAAAG TGTGTGTACC ACTTTACCTT TCTAAAATCT
35301 GAAAAATTCT GAATCTGGAA ACCCATTCTG CTTCAAGATA AATGGATCCT
35351 AGATTTATAT CGGTACCGTA CAGTCCTGAA ATTCCATCCT ATCTATTGGC
35401 CACTTTTACA TCAACAAACC TTTGAAGTTT GGGGAAACTT ACATATCACG
35451 CTCCCTTGGC AGTTGAACAT TATTTATTTA TTTTGAGATG GAGTCTCGCT
35501 TTGCCCAGGC TGGAGTGCAG TGGCGCGATC TTGGCTCACT GCAACCTCTG
35551 CCTCCCGGGT TCAAGCAATT CTCCTGCCTC AGCCTCCTGA GTAGCTGGGA
35601 TTATAGGCAT GCAACACCAT GCCCAGCTAA TTTTTGTCTT TTTAGTAGAG
35651 ACGGGGTTTC ACTATGTTAA CCAGGCTGTT CTCGAACTCC TGACCTTGTA
35701 ATCTTCCCTC CTCGGCCTCC CAAAGTGCTG GAATTACAGG CGTGAACCAC
35751 CACGCCTGGC CCTGAAGATA CATTTTAAAT CAATGAAAAA AACAACAGGA
35801 TTCTACCTCC TATGGTATAT CCCTCCTGGC TGTCTCTTCT CTCCAGTCTT
35851 GCCTCTGCTG TGTGGGTTTC AGGCATCCAT CTTCTCTACT CTGAATTACT
35901 GTGATAACCT CTGAAGTATT TTCCCTGCCA TCTGTCTGGC CTTCTCCCA
35951 GGTCTTCCAC ATACTGCAGC CAAGTCAGCC CGCTGTTGAA ACCCTTCAAG
36001 ACTCCCTGCT GTCCTCTGGA TGAAGTCCAG ACTCTTCCAC GTGACTTACC
36051 AGGCCTTTCT TGCACTTGTC CCCAGCCACT TACTGTTTCT CTCTTTCTAC
36101 CTTAACATCC TGAACTTCCT TTGGTTCTTT GACCTTGCCT CTGACCTTTT
36151 TCCATGCTGT TCACTCTTTC CCTGTTCACC TTGCTAACTC CTCTTTCTCT
36201 TTCTGGGTTG GATCAGATTT CACTTCTTCC AGAAGCCCTT CCTAGACCCT
36251 ATACTTCTGG AATGGCGCCT TTTGACTGTA CGCTCATTGC ACCCTGTACT
36301 TCTCCTTTAT GAGTGGGTGC TGGTCTGTCC CACTAGGCTA CTTCATCCAT
36351 AAAGGGAGAG TAGAGCTTTA CCAAGTCAAT GCTTAAGCAA TATTTATTGG
36401 ATGAATGTGT GATTAATTTC ATAGAAATTT GATGTGCATT CAAATTTACT
36451 TATTGTATTA CGGAACTTGC ATTATATTCT CAGTGGAGTT ATTTTCTTTC
36501 ACGTGTGTAA TTCAAGATAG ACTCAGTGAG ATTTTCAAAA TTTGGAATGC
36551 AGTGCAAGGA AATTGAACTT GAGTTCTTTT GCATTTTGAT GGTTAAAAAT
36601 TTCCATTTG TGGTGACATA CCACAATAAG CCAGTGAATG TGGCTTATTG
36651 TTTTCTGGTC TATAGAAAAT TGTCGCAAAC TCTGTCATAA TGTCTGGTTC
36701 TATATAACAA AGCTAGTCCT GTATTCTGCA TGTGGCTGAT GGAAACAGTG
36751 CTCTGTTGAT CTGGTTCATG AAGAAATCTG TTCAATTCTG CATAACAGAT
```

FIG. 3P

```
36801 GCCTTCATCA GTGTCCTTCC ATGAAGGAGC TGATCTTCAC AAAGAACACA
36851 TAGTTTTGCA TCCCACCACT TGCAGTATTT TTTTTTTTTT TTTTTTTTTT
36901 TTGAGATGCA GTCTCGCTCT GTCACCCTGG CTGGAGTGCA GTGGCATGAT
36951 CTCAGCTCAG TGCAACCTCT ACCTCCTGGG TTCAATTGAT TCTCCTGCCT
37001 CAGCCTCCTG AGTAGCTGGG ATTACAGGCG CACACCACCA TGCCTGGCTA
37051 ATTTTTGTTG TTTTAGTAGA GACGGAGTTT CACCATATTG GTCAGGCTGG
37101 TCTCAAACTC TTGACCTCAT GATCTGCCTG CCTTGGCGTC CCAAAGTGTT
37151 GGGATTACAG GCGTGAGTCA CTGTGCCCTG CCAGTATTGT TTTGTCTAAA
37201 TTATTTGTGC TGATGTTTTT CCTACTGTGG TTTTCTTCAG ATTACCCTTG
37251 CTCTGAGCCT GCAATTGACT CATGAACTTC TTTTCCATGT TCTAACCTTA
37301 CAATGACTTC CTTGTGTTCA CTCCAAATGT TTTTCCTGG TTGCATGTAG
37351 AGATGTATTA GCTAAGGTAC ATGCTTAGCT GCTGTATCAA AGAGACCCTA
37401 ATGTACAACC CAGGCTGGTA GAGCAGCTCT GCTGTATGTG TTAATTCAGG
37451 GACCCAGGTT CCTTCCATGT TGTGACTCCC CCCTTCCTTA GGATGTTGTC
37501 TTCTTTTACA TGGCTGAAGT TGGGCCATTT CATGTCTCTG TTCCAGCTGC
37551 CTGGTAGGAA AAAAGAACAG AAATTCAGAG TAAGCAAATT CTTTTTCTAT
37601 AGATGGATGC GGAAGTTGGA CACATCATTT CCTCTCACAT TTTCTCGGCC
37651 AGAACGTAGT CATGTGACTG CACGTCTAGC TGCTAAGGAG ACTGGGAATT
37701 TACTGTCGGC TGTGTGGCCT CTGTCAAGCT AAAATTCTTA TTACTGTGGA
37751 ATAAGGGAAG GATGGATTTG GGGCACAAT TAATAGTCTG TCACAGAGGC
37801 TAAAACAGCT GCTTTTGGCT GGGCACGGTG GCTCACACAT GTAATTTCAG
37851 CACTTTGGGA GGCCGAGGCA AGTGGATCAC TTGAGATCAG GAATTTGAGA
37901 CCAGCCTGGC CAACATGGTG AAACCCTGTC TCTCCTAAAA ATATAGAAAT
37951 TAGCCGGGCA TGGTGGCGGG TACCTGTAAT CCGAGCTACT CCAGAGGTTG
38001 AGGCAGGAGA ATTGCTTGAA CCTGGAAGGC AGAGGTTGCA GTGAGCCAAG
38051 ATGGTGCCAC TGCACTCCAG CCTGGGCGAC AGAGCAAGAC TCCATCTCAA
38101 AAAAAAAAAA AAGGTTAAA TAAACAGCTG CTTTTGTAGG TGATACAAGG
38151 TACAGCTAAG CTTTGAAGCC AGGCCTGTAG TTTCACCTTC CATATTCTTA
38201 CTCAAGGCAT TATACTTCTG GATCTGAAAC CACTGGATCT GATGCCCTGC
38251 TTGGGATGAG TTCTTTATAT TATCTTGCTT TCAACCCACA CCTGTGTAAT
38301 TTTATGGGCA GCGTTTGTTT CCTATATAGG AACAATTTGA AAGTGGGCTG
38351 TTTCTAGGCT TTCATGAATA GCAGGCTATG CTGTCATTGG GAATCTGGAG
38401 GGAGTTAATG AACACAACTT CATTGTTTAC TTTAGTGAAA TGTGGCAGCT
38451 TATGATAGTT TTGACAGTGA ACATGTGCT GTTTTGATCT CTCAGCTAAG
38501 ATTATCTGAT TTTTCAGGCA TGTCTCAAAA CTCACCAGGC TGCTCACAT
38551 GCTGCTGCTT CTGAAGCCAG GGTTTGGAAA CCAGCTGCCC ATCAGAATGA
38601 GGCTGTGACT TAGAATATTG GTTCTTGTTT TATTACCATT CCTTGTTTGG
38651 TCTCTCCAGA GTCACTGGCC TTTTCCGCTT CAATTTTCTT ATCGGTGAAA
38701 TGAGATATTA ATTCCTCTTA TTGACTTCAA TTCAATTGCT GAGTGTATTG
38751 TTGCCTTTGG GAGGTTCTTT GAGTTTTCTG TGCCTTTGAA ATAGTTGTTT
38801 TTTTTATTC TGGTGTTTTG AGGCATGTTT CAAGTGAGTG CATTTACACT
38851 TCTACCATTT TAGGAGCCAC AATTCAGTTA TGTTGTCCCA GCTTGCTTGG
38901 CCCCATCCCC AGAGTTTCTG ATTCAGTAGG TCTGGGGTGG GGCCCAATAA
38951 TTTGCATTTC TTCTTCTTTT TTCGAGACAG AGTCTGACTG TGTCATCCAA
39001 GCTGGAGTGC AGTGGCACGA TCGTAGCTCA TTGTAGCCTC AAACTCCTGG
39051 GCTCAAGCCG TCCTCCCACC TCACCCTCCT GAGTAGCTGG GACTATAGGC
```

FIG. 3Q

```
39101 ATATACTACC ATGCCCTGCC ACCTTTTTAA TTTTTTGTAA GGATGGGGGT
39151 CTCACTGTGT TGCTCAGGCT GGTCTTGAAT TCCTGGGCTG AAGTGATCCT
39201 CCTGCTTCAG CCTCCCCAAA TGCCGGCATT CCTGGCATGA GCCACTGCAC
39251 TTGGCCAAGA CTTTGCATTT CTAACTAGTT TCCAGGTAAT GCTGCTGCTG
39301 GTGTAGGGAC CTCATTTTGA GAACCATTGT TCTATAGCTG TAGCTATAGT
39351 TAGTTTCTGG TTATAGCTTC TTCCTTTTGT CCCTTCAGTA ATAGTGTACA
39401 CATCCGAAAT CCCTGTCCTT GCTCTTTCAG GCCCAGGCAT GGTATCTGGT
39451 CCTCTTCTGT TGCTAGCCCT GGGGTGCTTC ATCATCCCAA GTTTATTTTT
39501 CTTCTCCTAA CCTGAACCTT TGTAAATAGC CCCTTCCCTA ATGAACGTCC
39551 TCAATTCCCT GTTTTGCGTG TCCTGTCTGT TCTTGGCAA GACTCTGGAT
39601 GATTCAGTAC TCAATGAGGA TTTTCGCAT AGATGGATGA AACAGGCTGG
39651 GTTTCATGTT TTCTAAGATA AGGTGCTTC TCTCTTTTC TCTTGGTCAC
39701 TTTGACCAAG AAGAAAATAA CAGAGTTTTT ATTCTCAAGA AGAATAATAT
39751 CGGGGCCACT CTGCTCAGAG GCCACTCTGC TTTGAGGACC CCTTCTCTCC
39801 TCCTCATGC CAAAGATCAG GAACATTGGG CAGAGCGGAT AACGATGCCG
39851 CCAGCGTCAT TACATTTTCA CGGCACTTTC AGTTGTGCTG AGCGTGCAAA
39901 CATTTCAAGG AGACATTTCT AAGAGGTGGC TAGCACAGCA TGCCTCTAAT
39951 GCCCTATGTG AATTGGAATA GAGTACTAAA GAACTGTTCA ATATTCACCC
40001 CATCCCCGCA TATGCAAGCA TGCACGTGGG TTCATTGTAT ATGTGTGTGT
40051 GCACGTGTGC ACAGACACAT TTGTCCTTCG TTTCAAATGC AACACAATGG
40101 ATGGAAATTG CCTTCCTGGT ACTGGGGTAT GGATGCAAAC ACCAACAGAG
40151 AAGCAGCCGC TACTTCCAAA CTGAACACAT GTGAGATTTG CCCTTTAATT
40201 AGCATCTGCA GCTGCTGCCA TCAGAAGGGT CTGTCTCTGT TGGCCTGAAA
40251 GTCTTTGCTT TAAAAGAGCA AGTCCATTAT AGCTCCAAGC CAGGCTCGTC
40301 TGTCAGCTGC TGTGCTTTCT CTGCCATCAG CGGGGTTGCC ACATTGTTTT
40351 GGGCTGTTTC ACTCTAGGAC TCTTTCCTCC TCCTGTGCCC CCAGCCTTTG
40401 ATTACCATGC CTTGGTGATC CTCATTTGGG TGACCTGCAG CTGCTCATTG
40451 TGTGTGCAGG AGACATCTCC AGTCCTTGTA AGGAGGGAAG ATCACTGGCT
40501 TCAGTGCTGA TGGACTGGTT ATTTCCAGC CCTTTGTCGT CAGTGATCTT
40551 GTCTTGATAT GCAGAAAGGC TCCAGGTAGT CACTGAAAAA AATATAAGCA
40601 GCAGAGGTGA TGGCTATATG AAAGTCACGT TCATCAAGG GCATTGCTGC
40651 TATGAAACT TTCAATTCAC TTGGAGTAGG GAGCCATATT GGTTCCACAG
40701 CCTCCTCAGC AGTGGGTCCC AACACAGTGC TGGGCTAGCT GCCTCTGAAT
40751 CACCGCAGTA GCTCCTTTTA CTATAGATTC CTGGGTCCCA CCCATGGAAT
40801 GTGATCCATG AAGTCTGGGG TTATTCCCTG GAATCCTTTA AGCTCCCTAA
40851 GTGGTTGGGA TGGGAAAGAG ATATGCTTTA TGTTACTATA CTTCTTCTTA
40901 TTATTATTTT AAAATTCTTG CCGGGCGCAG TGGCTCACAC CTGTAATCCC
40951 AGCACATTGG GAGACCGAGG CGGGTGGATC ACTTGAGGTC AGGAGTTCGA
41001 GACTGGCCTG GCCAACATGA TGAAATCCCG TCTCTACTAA AAATACAAAA
41051 ATTAGCTGGG CATGGTGGCG CATGCCTGTA GTCCAGCCA CTCCGGAGGC
41101 TGAGGCAGGA GAATCGCTTG AACCCGGGAG GCAGAGGTTG CAGTGAGCCG
41151 AGATCGTGGC ACTGCACTCC AGCCTGGGTA ACAGAGTGAG ACTTCATCTC
41201 AAAAAAACC CAAAAAAACA AACTCTTTT TCATTATACC GGAACGTCAG
41251 CTTTATGGAG TCGGGGATTT TTTCTGTTTT ATTCACTGCT GTTTCCCTAA
41301 CATCTAGAAT AGTGGCTGGC ACGATAGGCA CTCAAGTATT GATTTAGATG
41351 AGTCTATTTT ATTTTCTTTT AAATTTTAA TTTTTATTAG AGGTGGGGTC
```

FIG. 3R

```
41401 TGGCTTTGTT GCCCAAGCTG GTCTCAAAAC TCCTGGCCTC AAGCGATTGT
41451 ACTGCCTCAG CCTCCCAAAG GGCTAGGATA GGCATGAGCC AACATGCCTG
41501 GCTTGTCTTA TTTTTAACAA GCACTTCTGG TGATTCTGAT GGACAATCAG
41551 GCTTGGGAAG TTCTAACCTA GAGGACCTAC AGTTGTCTTG GGGTAGAAGC
41601 CAAGGCTATC CTGGTTTTTA GAATCAGTGC CTTACTGGGC ATCTCTGAAG
41651 AGTAAAAGTC AGGGACAGAG TTACATTTTT GGACAAAACC AGATGCTGTG
41701 AATGGACTCT TGGTCACAAC CTGGGTGGCG ACTTGGTCCT TAACTTCTTC
41751 ATCATTTTCT GCTGACCCTG TTCTTTGGTT CACAGCAAGT CACCTGATAA
41801 GAAGACTCAA AGACTGCTAG TTTGTTACTT TAGATGATGC TTTTGGAACC
41851 TCTTGGTACC ATTTTAACAA TCCAAACGTA TTTTATGAAA GCACTCAAGT
41901 CCTGGGTCTT TATTGTATCT TTAAGCTCTA ACAGCATGAT GATTGAATAA
41951 GCTGTGGTTG CCACACACA AGCCATCTTC CCCATGGCCT CCATTCATAC
42001 TAGAATGAGC AGCTATACCC CAGTAGTATA GTTTTGGGAT ATGGGTAACA
42051 TCTTGGGATA GCCACATTTA CTTAGTAAAT GTCTGGCTTA CATTCTCCTA
42101 ATGGTGCACT GTTGGAATTT TTGGTGTGGT AACCTGGAAT AGTGTTGGTG
42151 GGTCAAGTTT GATTAGCATC TTTGATAAGG ACCCGGTCTA TTTAGAGGTT
42201 TGTCATTGAG TGTGTCTGTT TTGGCCTCAT GTTGTGAAGC ATGCTGTGTA
42251 GCAGCTGTTG TAATTTTTGT TGCTTGTTTT CTCAATCAAC CCTGGTTTTG
42301 AAGAAATGGG AAGTTGTTCC ACTCTTAGAC TGATCTGACT TGGGAGGGGA
42351 TTTTCAGTTC AGGAAGTTGG ATCTTCTGAA TGGAAGCAAA GAATACATGT
42401 CTTTTTGCCA CTTTACAAGC TGGCTCTTGT TTTCTGAACT ATTTTACTGG
42451 TCATTGCAAA TAGAATGTCA GGAGTAGCTG CCAAATACTA AGTTGTGTTC
42501 AGTTTGTCAG TTCTTAAGAG TTGCCGGTGG CTGCTCTGCT ATGCGTATGA
42551 CTTTCTCAGC CTTAAACTTA CAAGCCATAC TGTTTTTTTC ACATCTTTAA
42601 TACAGCCATA GGAAATTTAT AACTGTGGCG TGTCGTCATA AATATGCATT
42651 GTTCTTATTT TAAGACATTT CAGTACTAAA AGTATAAGTA CTTCTGTTAT
42701 TATCTGTGAA TTTCTTTCCT TCTTCTTTTT TTGGATATTT AAGACCTTTT
42751 CGATGTCAAT ATATATTTAA AACAGACATA TAAATTAGCA TTCACCCACA
42801 TACCCAGGGC CTATGGAGAA CCAGGTTGGG ATGAGTGGGT GAGCTACAGG
42851 CAGCCAGGTG GCTCCTGTGG GCTCCTCAG GACTGGGGTG AGTAACTAAT
42901 GTCTGCTAGG AACTTGGGGG AAAGAAGGTG TGTATGTTAG GTGCTGCCCC
42951 CTTCTAAGTG TTCCTCTTGT TCATAATTTT TTTTTTTTTT TTTTTTTTA
43001 GATGGAGTCT CGCTCTGTTG CCAGGCTGGA GTGCAGTGGT GTGATCTCAG
43051 CTCACTGCAA CCTCTGCCTC CCGGGTTCAA GTGATTCTCC TGCCTCAGCC
43101 TCCCGAGTAG CTGGGACTAC AGGCATGCAC ACCATGCCC AGCTAATTTT
43151 TGTATTTTTA GTAAAGACGG GGTTTCACCA TGTTGGCCAG GGTGGTCTCG
43201 ATCTCTTGAC CTTGTGATCC GCCTGCCTCG GCCTCCCAAA GTGCTGGGAT
43251 TACAGGTGTG AGCCACTGTG CCCAGCCCAT AAATCAAAAT TTTTTCAGCA
43301 ATTGTTATAC AAGTGGAACC TTACTCTTCA AATGCAATTG TCCAGTGTCT
43351 GGCTTAATGT CTGCTGTTGT CAGAAACCAT GTGAATGGAG TAGATTCCCA
43401 GGTTATAAGG AGCCCCAGG GAGGATGCGC GAGTCACTGG CTTCTCCAGG
43451 GGTCTCTGGT TTGGGGTTGC CTTGGTGCTG GCACACTTC CTGGAGATTT
43501 TACTGGACCA GCCTGAGGCC TTTGGGCTC TGTGCAGATG CTCTACTTCT
43551 GACTTGTCTA GAGCTTTCTT CTAATTCTGG ACTAAAAGCA AGCAGGAGTT
43601 TGGAGGATGA TGGTGAGAAT TCACATCCCC GAGTTGGCTT TTGGAATGCA
43651 GTAGTTTGTG AGATTTAGTG TTTTTTTTAA GAAGTATATT CAGATCTTGC
```

FIG. 3S

```
43701 CTTTTTCCCA GAAAGCATAT GAGACAACTT CCAAGACATT TATAGCATGG
43751 CTAATAAAAT GGGAAATCAG GGCGAAGGAC AGGAGAACTC AATAAGGGTT
43801 AACATGGCTA CAGCGATTGT CTAAATGGGT TCTTTTTGCT GGCCAGAGCA
43851 GAAAGGATCA TGCAGTAAAG TGGGGGGGAA GAAAGGGAAT TGAATGGTAG
43901 GTGAAGACTT CATGTTGGTG CCAGGCACTG TGCCAGGCCC TCCTAGGACC
43951 TTGTCTTACT CAATCCTCAC ACAGTGCTGC AAGAGGATTA GTCTTATCCC
44001 TGTTTTAGAG AGGATGAAAC TGAAAGGCAG CGAGGTGAAG TCACCAGCAG
44051 GAGGCTGAAG CCGCCCAGGC TAACTGGCCT TATAGCTACC TAGGGACTCA
44101 GGAATATCAC ACCTGTTTAT CATCAAAAGG AGAAAGGATT TCAGTTCCTT
44151 GGGGTAGAAG AGTTTCTTTT TGCTAATCAA ACATTTTACT TGAGGCTTCA
44201 TATTCTTCTT CAAGATTTTT TTCCTGTGTA TGTACCAACA CATGTAATAA
44251 TTCCTTGTTT ATTTCAAAAA AGGGGTTGTA CTTTATTCTT TACAAGATTT
44301 CACTTTATAT TGTCATGGAC AATTTTCCAT GGCAGTATGA ATAAATGGAA
44351 TCTGTTTGTT TTTAATATCT TTGTCTTATC CCATTGTTTA CATATGTCAT
44401 ATTTTAGCCA GTCTCTAACT GATGGATAGC TGAATGATTT CCATGTTTTT
44451 TTCCCCTGTT ACAAACAATA CTGCAAGGAA TCTATTTATC TTTCTATTTA
44501 TCTGCAAACT ATTGTAAGTA CCTGTAAATT GTTAGAAGTG GAATTACTAG
44551 GTCAAAGGGG ATATTTTCAC ATTTAAATTT TGAATAGAGG CTGTCAGTTG
44601 CCTTCCACAC TGACTATAAA AGGAAAAGAT TGTATCACAT TTATTGCAAG
44651 CCTTCTGTAT TCTGCTGGGT GCTGAGGGGA ATACAGAAAG GATATAAGAG
44701 TGGTTGCCCT CTAGGAATAT CCGTCTACAC TGTACCTAAT CCTAGGGAAT
44751 GTCTGGGGTG TCAACTTGTG GGTGGGAAAG TGGGTGGATT TAATTCAACT
44801 GTTCAAGCTT GCCTTGCAAA CACTGTGCAT GGTGTCTGGG ACTAGTCTTT
44851 CATTATATTG ATTCCCCTGG GTAACAGATG TAATTTCCTT AGGGCAGGGA
44901 CTTCATCCTA CATGACTTAC AGCGTGCCTT ACACATCTTC TTTGCTTTGT
44951 GGAGACCTTG TTATTATAAC ACGTCAGGTG ATATTCGAGG ATCTAATTGA
45001 GGCATTCCCT ATTTTTGGGT GTGTGAAGAA TTAATAACTT TGGCATTCTA
45051 TACAGGTCAT GGAATATCAG CCTGGAGGGG ACTTGCTGTC ACTTTTGAAT
45101 AGATATGAGG ACCAGTTAGA TGAAAACCTG ATACAGTTTT ACCTAGCTGA
45151 GCTGATTTTG GCTGTTCACA GCGTTCATCT GATGGGATAC GTGCATCGGT
45201 AAGTGAGACT CTGGTAGCAT TTTTATGCTG AGGATTTTCC TGTGTCGCAT
45251 AAGAGTTCCT GCATGGAAAT GAGTGGATGA GTGATTTCAA GATCAAGATA
45301 ACGCCCCATC CAGTTTTTAG CCAGTCTACC AATAACTGGC TGAAAGCAAA
45351 CTTTCCAAGA TGGAGGACAT TCAGCTTGC TTATCCAGCA GTGCAATAGA
45401 TCTAGAATTG TAATGTGCTC AAGTTTGCTA GTAATATCTA TTAATGTAGC
45451 TAAATAAGAC TGGGAACTCT TGCATGGGTT CTTTGGGTTA TATGATAGAA
45501 GAACTGAATT TGGTTTGCAG AAGGAAATGT CATACCACAT AGTAGTGTAA
45551 GACCATGGAG CTGTACTTCT CTAACTCTGC CCGTTAGAAT TTACAATTTT
45601 TTTTTTTTTT TTTTTTTTTG AGACAGAGTC TAGCTCTGTT GCCAGGCTGG
45651 AGTGCAGTGG TACCATATTG GCTCATGGCA ACCTCCGCCT CCTGGGTTCA
45701 GGTGATTCTC CTGCCTCAGC CTCCCAAGTA GCTGGAATTA CAGGCACGCA
45751 CCGCCATGCC CAGCTAATTT TTGTATTTTT AGTAGAGATG GGGTTTCACC
45801 AGGTTGGCCA GGATGGTCTT GATCTCCTGA CCTCATGATC CACCCACCTT
45851 GTCCTCCCAA ATTGCTGGGA TTACAGGCAT GAGCCACCAT GCCTGGCCTA
45901 CAAATCCTC AGTTGGTAAG TGGTTCTTCA TGTCTTCATT CATCTGATGT
45951 TTTGTGTACA TCTGAGAATG TTGTGGGAAT ACAATGATTG TTAGTCCAGG
```

FIG. 3T

```
46001 AATCACAAAA TTTGAGATAG AGTCTCAGCT TTTCCATTGC CTAGCTACAT
46051 GACCTTGGGA AAATTTCATA GCTCCTTTTG GCCTTAGTTT TCCTCATGTG
46101 AAATGTGTGT CTCTAGGAGA ATAATCCAT  TGAATAATAT GTGTTTCATT
46151 TCTCTTCCTT TTCTTTCTCT CCTATCCTTC CTTGCTCCCT CTCGCCCTTT
46201 TTCTCTTTCC CCCTCTCTCC CTCTCTCTCT CCTTCCTTCC TTCCTTTCGG
46251 TTAAATTCAT TTTGCAAAAT GTATGCTAAT AATTTATATC CACCAATAGA
46301 GGAGGTCTAT ATAACAGAAT ACATAAACAA AGATTTTTGG CTCAATTGAG
46351 ATTCTAGGTT AGCACTTGCT TGCTGATTGG GATGGAGGAG GCAATTCATG
46401 GTCCTGATTT TCTTACAGAG ACATCAAGCC TGAGAACATT CTCGTTGACC
46451 GCACAGGACA CATCAAGCTG GTGGATTTTG GATCTGCCGC GAAAATGAAT
46501 TCAAACAAGA TGGTAAAAAA TGGAATAAGA TAGCTTAATA GAGTTTATAC
46551 TAAAAAGTAT TCTTGGTCCT CCTAAGTTTG GGAAGTGTTG GGATAAAATG
46601 GTGAACAATG TTTTGGAGCC TTTGGCAGTG TATGGGGGTG GGGACAGGGA
46651 CACAGAACCA TTTCCCAGAC CGTGGCACCT TTTTATTTAT AGTGCCTGTT
46701 AATACCCTCC AAGACATTTT TAGGAGCATT GTTATAGTTT GGTTAGAAAT
46751 AAAGGAAAAT GCTTATTTTG TTTCTCTCTT CATTTTCCTT GCCTGTTATA
46801 GACTGTCTTT TGTTATATTA TCTTTTTTAC TTTAAAATAT TTTGATGAAA
46851 TGGAAACTCC TGCATGTCAA ATCCTCTATT TCCTATGCAG CAAAATTGAA
46901 ATTAATCACT GGAGCATTTG AACCAAATAT CCTTAAGTGT TAAGAACCAA
46951 GTGCTCAAAA TATCATTTTT AAGTCTTGGA TCTTTGGTAG AAATTAAACT
47001 GTATTCCACA TGCTAAGTAG GACGGCAGGA GGGTAGCTAC TGAGATCAAG
47051 AGTGAGACTA CTTTAGGAAA AAGATGACAA AGTAAAAAAA GATTAGAGTT
47101 TAAAAATCTT CTAATAAAGT TGGTATGTAC TAAAATATGA ATTTGGAAGT
47151 CAACTCCGCA AAAAAGGATA GGTCTAAGAG AAAATCGACT TAGGTTTTAA
47201 GACTGATTTT ACAACTGAGC CATTTGGTGA CCTAGACAAA TCCTTGGGAA
47251 CTTGATCTTT TATACTTTCT CTAGAAAAAA CTGATGCTAG TGAAAATGCA
47301 TAATTTAAGA GGTTAGAGAA GCTGCTCTTC AAAATGCCCC CCAAGTCTGA
47351 GAGTTAAATC CTTTACATAA AGGACAATAT GTAAAATTTT CTTTTTCTTT
47401 TTTCTTTTTT TTTGAGACGG AGTCTCGCTC TGTCCCCCAG GCTGGAGTGC
47451 AGTGGCGCGA TCTCGGCTCA CTGCAAGCTC CGCCCCCCTG GGTTCACGCC
47501 ATTCTCCTGC CTCAGCCTCC CGAGTAGCTG GGACTGCAAG CGCCCGCCAC
47551 CATGCCCAGC TAATTTTTTG TATTTTTAGT AGAGACGGGG TTTCACCGTG
47601 TTAGCCAGGA TGGTCTCGAT CTCCTGACCT CGTGATCCAC TCGCTTCGGC
47651 CTCCCAAAGT GCTGGGATTA CAGGCATAAG CCACTGCGCC CGGCTCTTTT
47701 TTTTCTTAAA CTGCTTCCAG AAAAGTGGAT ATTATTAGGT TGATGTTAAG
47751 AAAAGGCTTG GAGTTGCATT AACTTTTGC  TTTCTAGCAT CTGGCCTGTC
47801 TGTTCTGCAG ACCTGAGACC TACTTGAGAT AATTTTCTTG GTGTTCAGGC
47851 CCTTGGAAAA ATAAGTTCCC TATGTTGTCC AGTGTCAAAG TTTCTCAACC
47901 TCAGCACTAT TCTTTTTTTC AGGTTATTTT CTTGTAATCT GTTCACTTGA
47951 TCATTACATT AAGAATTAGA TTATATTGCT ATAACTACAA AGCATTTTAT
48001 GTTTTAAAAA TTATGTACAA TTTAGAAACA GGCATGAAAA CTTAGGTATT
48051 AAATTTAGTG GAATAAAGCA CAGAAAAAAA GTTAAAATAA TGCAGTTTTA
48101 TCACTTAGGA TTAAACATTT ATATGGGCCG GGTGTAGTGC CTCACACCTG
48151 TAATCCCAGC ACGTTTGGAG GTCGAGGCGG GAGGATTGCT GGAGTTTGAG
48201 ACCAGCCTGG GCAACAAAAT GAGACCTAGT CTCTACAAAA AATCAAAAAA
48251 TTAGCCAGAC ATGGTAGTAC ATGCTTGTAG CTCCAGCCAC ATGGGAGGCC
```

FIG. 3U

```
48301 AAGACAGTAG GATCGCTGGA GCGAAGGAGG TTGAGGCTGC AATGACCGTG
48351 TTTGCACCAT TGCATTCCAG CCTGGGCGAC AGAACAAGAC CCTGTCTTAA
48401 AACAAATTTA TATGCTGCAT TCGTGAAATT AAAAAAAAAT CATGGATTTA
48451 GAAATAAATT GAAGCAAGGT ACATTGACAG TGTAACCTCA GCACTACTGA
48501 CATTTTGATC TGAATAATTC TTTGTTGTGG GGGATGCGCT GTATAAGATG
48551 TTTAGCTGCA TCCCTGACTC CTACCTCCTA GATGCCATTA GCACCCTCCC
48601 CTCCAGATGT GATAACCAAA AATGTCTCTA GACATTGCCA GATGTGCCTG
48651 GGGTAGGAGG GTTGGGGGAA GTGGGGTTTG AGAACCCTTA GTTGATCATG
48701 CCTGCAGTAG GTTGAGAAGC ATCAGAAAGC TAATTAATTA GACAGGAATA
48751 TGTGTTTGCA GTA    (SEQ ID NO:3)
```

FEATURES:
Genewise results:
Start:    3121
Exon:     3121-3216
Exon:     10089-10230
Exon:     21592-21767
Exon:     29016-29117
Exon:     45056-45198
Exon:     46419-46530
Stop:     46531

Sim4 results:
Exon:     2001-2040,    (Transcript Position: 1-40)
Exon:     3108-3216,    (Transcript Position: 41-149)
Exon:     10089-10230,  (Transcript Position: 150-291)
Exon:     21592-21767,  (Transcript Position: 292-467)
Exon:     29016-29117,  (Transcript Position: 468-569)
Exon:     45056-45198,  (Transcript Position: 570-712)
Exon:     46419-46764,  (Transcript Position: 713-1058)

CHROMOSOME MAP POSITION:
Chromosome 12

ALLELIC VARIANTS (SNPs):
DNA

| Position | Major | Minor | Domain |
|---|---|---|---|
| 722 | A | G | Intron |
| 11380 | T | - A | Intron |
| 14282 | G | C | Intron |
| 30482 | A | G | Intron |
| 30903 | G | A | Intron |
| 31969 | T | C | Intron |
| 33307 | G | - T | Intron |
| 38763 | A | G | Intron |

FIG. 3V

| | | | |
|---|---|---|---|
| 38854 | A | G | Intron |
| 46559 | G | A | Exon, 3' UTR |
| 47193 | G | A | Intron |
| 48129 | T | C | Intron |
| 48676 | G | - | Intron |

Context:

DNA
Position

722
TCTGGCTGTTGCTTTCTTTATGGTTTTGTCATTACTTTAAACAATGACAAAAACTGCAAT
GATTTGCATCAACCTAATACATCCCTCCTTAAACAATGTTGCTTTGTTTTGTCCTGTTTT
GGAACTTATAAGAATGGAATCATAATGGAATCATATGTTATTTTCTTGCTTCCTTCATTA
GGCCTTGTTTTGAGACTCATTATGTCATTGTGGTTAGTTGCAGTTTATTCTTTTTCATTG
CTTGTGAAAACACTGCAATATACAATTTTGTCTTTTCTACTGCTGATGGACATTTATATC
[A,G]
CTTCCAGTTTTTTGCGAACACTATTTTGTATTCTTATACACATCTCTTGGTGTACATAAG
TAGGAGTTTCTCGCCGGCGTGGTGGCTCAGGGCCTGTAATCTCAGCACTTTGGGAGGCCG
AGGTGGGCAGATCACTCGAGGTCAGGAGTTCAAGACCAGCCTGGCCAACACGGTGAAACC
CCATCTCTACTAAAAATACAAACAATTGGGCATGGTGGCATGCACCTGTAATCCCAGTTA
CTTGGGAGGATGAGACAAGAGAATAGCTTGAACCTGGGAGGTGGAGGTTGCAGTGAGGCG

11380
TTGCCCTATTACCCAGGCTGGATTGCAGTGGTATATCATGGCTCACTGCAGTTTCAACCT
TCTAGGCTCAAGCAATCCTTCCACCCCAGTGGCTGGGACTACAGGCTCACACTACCACGC
CCAGCTAATTTTGCTTTTTTCTCTGTAGAGATAGGGTCTTACTATGTTACCCAGGCTGG
TTTCAAACTCCAGGCTTGAAGCAGTCTTCCTGCCTCAGCCTCCCAAAGCTTTGGGATTAC
AGGTGTGAGCCACCATGCCTGGCCCCATAAAATATAATTTTTGAATTCTTTTTTGTTTTT
[T,-,A]
ATGGAGGAAGGGGCTGAGGAAGGCAAAAGTACCTAGGGCCTATGAAGTCATATATTGGCC
TTGCCTTCACCCTGTTTCTGACTTTGCTTGACTTCCATGTGATGAGGCAGTTGGCTGTTA
GTGTCCCAGTTTCATACTCTTACATTAGTGTTTTTCAACCAGTGGGTGATTTGACGTTTT
CGGTTGTCAGAGCTAGTTGGGGGTGGTGGTGTGTGAGTTTGGGGGGAAGGGTCCTACTGT
CAGTTAATGGGTGAGGCCAGAGATGCCACCAAACACCTTACAGTGCACAAAGCAGCCCCC

14282
CTTACTGAGCCATCTGCAGGCACCTTCATTAGTCTTGAGACTGTCCTCTGGTTACTTAAC
AGCAGTGAATTATCTAGAATCATTTAGTGATCAGAAGACTTGGTTTAGTGGAATGTAGAT
TTTTTTCTAATAGACCCCTCTTCCAGGGAAATGTTTCATATTTTTGAAGAGGTTTCCTGG
GGAGTGTTTAAGAGGCCATGATTGAAAATGGGTGATTACATTAGTGTGTTTTCTATTCCT
CCCCTTTTTGAGTTTCTGTTTTGGAATGTAAGCTTTGTTTTTCTACGTGGAGAAGGGTCC
[G,C]
TCAGCTGCTTCTGCCCAGGTTTTTTGAATCTTCCTATAGGGATGGAGATTTTCTTTGGGG
ACTGTTAGAGAAATGGAATAGAGTGTAGCTCTGAAGGAGAAGGATGTCTCCAGCAGAAG
TACCTCTAGCCTTGGGCCAAGGGAGGGAAGGGAAGGGAACGAGCATCTGGGAACCAGGGA
AGGGATTTTGTCTTTCTTAATTACTCTTACATCCCCAGTGCCCAAAATAGTGTCTGGCA
TATGTTAAGTCCTTAGTAAATACTTGTTGAATGAGTGTATGCTCAGTGAACAAAATAAAT

30482
AAGAAATGTTAAATGGTTACATAAGCTTTCCCTTTCTGACCCTTAACTGTGCTCTGTAGG
AGCATGGTGGGGATGTTTCTTTTCTTTTCTTCTTTTTTTGAGACCAGGTCTCACTTTGC
CACCCAGGCTGGAGTTCAGTGGCATGAACATGGCTCACTGCAGCCTCGACTTCCTGGGCT
CCAGCAAACCTCCCACCTCAGCCTCCCGGGCATACACCACTGTGCCTGGCTAATTTTTGT

FIG. 3W

```
         ATTTTTAGTAGAGACGGGGTTTTGCCATGTTGCCCAGGCTGGTTTCGAAGTCCTGAGCTC
         [A,G]
         AGAGATCTTCCTGCCTTGGCCTTCCAAAGTGCTGGGATTACAGGTGTGAGCCACCATGCC
         CAGCTCCGGTGGGGGATATTTCTATATCCACATGTGTATAGTTTACTTTATAAAAATGGT
         ATGTTACTCTGTGCTTGGCTCTCCAGCTTGCTGTTGCCTTTCACCAGTGTATCCCAGACA
         TCCTTTCTTCCTTGTCAGTAACGCAGGTCTACTTTATTCTTTGAGCAGTGGCATAATTTT
         CCCTGATGTGTATATATCATAAGTTAGAGAATGCTAAAATTCATTTTGGGGCCTTGTTTA

30903    ATGTTACTCTGTGCTTGGCTCTCCAGCTTGCTGTTGCCTTTCACCAGTGTATCCCAGACA
         TCCTTTCTTCCTTGTCAGTAACGCAGGTCTACTTTATTCTTTGAGCAGTGGCATAATTTT
         CCCTGATGTGTATATATCATAAGTTAGAGAATGCTAAAATTCATTTTGGGGCCTTGTTTA
         GGTTCTTGAGGGATTAAATTCCTAAATTTAACAAGTGTATCCTGGAAACAATTTTGTTC
         CTGATTCAGCCCTTAAAAGAGGACTATCATGTTACCTTGAATGGAGATAAACAGGCTCAC
         [G,A]
         TAAGAGAAAAGGGTAAGAGGGATGAACTCCCACTTATCTTAAACTTCTACTGGCCCGTTT
         TTGGGGAATTTGCTGCTTTTATTCCTGACCTAAAATAAATAAGTTTATGTGTCTTGGTTT
         CATATTAGTTGAGAACCCAGTGCCTGGAGAGAAGTTTTCCTTGTCCTCTGAGTGAGGACA
         TTCACATATGAATCTATTGGCAGACTGGCTTTGACTGACCACACGTGCCTTCAGAACCAA
         TGCCACAGCTCTTAGGTTTATGGCCTGAAACACCCTTTCCTTACATATTGCCTTAGAAAC

31969    CACTGCGCCTTTTCTTTTCATTTTTTTTCTGAGATGGAGTCTTTCTCTGTCACCAGGCTG
         GAGTACAGTCATGCAATCTCAGCTCACTGCAACTTCCACCTCCTGGGTTAAAGTGATTCT
         CCTGTCTTAGCCTCCTGTGTAGCTGGGACTACAGGCGTGTGCCACCGTGCCCAGCTAATT
         TTTATATTTTTAGTAGAGACGGGGTTTTGCCATGTGGGTTAGGCTGGTCTTGAACTCCTG
         ACCTCAGGTGATCCACCCGTCTTGGCCTCCCAAAGTGCTGGGGTTATAGGCGTGAGCCAC
         [T,C]
         GTGCCCAGCCTCAGGCTTCTTTATTAAGAAGAAGTTCGGGCCAGGTGTGGTGGCTTACAC
         CTGTAATCCCAGCAATTTGGGAGGCCGAGGTGGGCAGATCAGGAGGTCAGGAGATCGAGA
         CCATCCTGGCTAACATGGTGAAACCTCGTCTCTACTAAAAATATAAAAATTAGGCAGGT
         ATGGTGGCGGGTGCCTGTAGTCCCAGCTACTCGGGAGGCTGAGGGAGGAGAACGGTGTGA
         ACCTGGGAGGCGGAGCTTGCAGTGAGCCCAGATTGTGCCAGTGCACTCCAGCCTGGGTGA

33307    TGAAGGAACTCAGTTGAGGATTTAGTGGTCCATGTGGCAGGCTACTGCTCAGTAGCTTCA
         GGGAAACCACTGCTTGCCTCCCCTGTGGCCAGTGAGGATGATCAGAGGAGTCCCAGCAGG
         AATGCCCAAATGTAGTTTTCTTACATGTTGATGGGAGTGCATTGTTTCATGTCTAAACAG
         TTCTCAAATCACATCTTCAGGAGGGTACTATCTGGGCACTTTGATAATTTCTCACTTTGA
         TGTCACCGTTCTTATTACCATCACCTAGTTTTGTCATAGTAGAAATAACTTTCCTTTTTC
         [G,-,T]
         GTGTGTGTGTGTGTGTGTGTGTGTGTGTGTGTGTGTGTTTTGAGATGGAGTCTTGCCG
         TGTTGCCCAGGCTGTAGTGCAGTGGCGTGTTCTCGGCTCACTGCAACCTCTGCCTCCCGG
         GTTCTCCTGCCTCAGCCTCCCGAGTAGTTGGGATTACAGGCGTGTGACACCACGCCCGGC
         TCATTTTGTATTTTCAGTAGAGATGGGGTTTCACCACTTTGGCCAGGCTGGTCTTGAAC
         TCCTGACCTTGTGATCCGCCCACCTTGACCTCCCAAAGTGCTGGGATTGCAGGTGTGAGC

38763    GACAGTGAGACATGTGCTGTTTTGATCTCTCAGCTAAGATTATCTGATTTTTCAGGCATG
         TCTCAAAACTCACCAGGCCTGCTCACATGCTGCTGCTTCTGAAGCCAGGGTTTGGAAACC
         AGCTGCCCATCAGAATGAGGCTGTGACTTAGAATATTGGTTCTTGTTTTATTACCATTCC
         TTGTTTGGTCTCTCCAGAGTCACTGGCCTTTTCCGCTTCAATTTTCTTATCGGTGAAATG
         AGATATTAATTCCTCTTATTGACTTCAATTCAATTGCTGAGTGTATTGTTGCCTTTGGGA
         [A,G]
```

FIG. 3X

```
             GTTCTTTGAGTTTTCTGTGCCTTTGAAATAGTTGTTTTTTTTATTCTGGTGTTTTGAGG
             CATGTTTCAAGTGAGTGCATTTACACTTCTACCATTTTAGGAGCCACAATTCAGTTATGT
             TGTCCCAGCTTGCTTGGCCCCATCCCCAGAGTTTCTGATTCAGTAGGTCTGGGGTGGGGC
             CCAATAATTTGCATTTCTTCTTCTTTTTTCGAGACAGAGTCTGACTGTGTCATCCAAGCT
             GGAGTGCAGTGGCACGATCGTAGCTCATTGTAGCCTCAAACTCCTGGGCTCAAGCCGTCC

38854   GCTGCTTCTGAAGCCAGGGTTTGGAAACCAGCTGCCCATCAGAATGAGGCTGTGACTTAG
             AATATTGGTTCTTGTTTTATTACCATTCCTTGTTGGTCTCTCCAGAGTCACTGGCCTTT
             TCCGCTTCAATTTTCTTATCGGTGAAATGAGATATTAATTCCTCTTATTGACTTCAATTC
             AATTGCTGAGTGTATTGTTGCCTTTGGGAGGTTCTTTGAGTTTTCTGTGCCTTTGAAATA
             GTTGTTTTTTTTATTCTGGTGTTTTGAGGCATGTTTCAAGTGAGTGCATTTACACTTCT
             [A,G]
             CCATTTTAGGAGCCACAATTCAGTTATGTTGTCCCAGCTTGCTTGGCCCCATCCCCAGAG
             TTTCTGATTCAGTAGGTCTGGGGTGGGGCCCAATAATTTGCATTTCTTCTTCTTTTTTCG
             AGACAGAGTCTGACTGTGTCATCCAAGCTGGAGTGCAGTGGCACGATCGTAGCTCATTGT
             AGCCTCAAACTCCTGGGCTCAAGCCGTCCTCCCACCTCACCCTCCTGAGTAGCTGGGACT
             ATAGGCATATACTACCATGCCCTGCCACCTTTTTAATTTTTTGTAAGGATGGGGGTCTCA

46559   ATTTTGCAAAATGTATGCTAATAATTTATATCCACCAATAGAGGAGGTCTATATAACAGA
             ATACATAAACAAAGATTTTTGGCTCAATTGAGATTCTAGGTTAGCACTTGCTTGCTGATT
             GGGATGGAGGAGGCAATTCATGGTCCTGATTTCTTACAGAGACATCAAGCCTGAGAACA
             TTCTCGTTGACCGCACAGGACACATCAAGCTGGTGGATTTTGGATCTGCCGCGAAAATGA
             ATTCAAACAAGATGGTAAAAAATGGAATAAGATAGCTTAATAGAGTTTATACTAAAAGT
             [G,A]
             TTCTTGGTCCTCCTAAGTTTGGGAAGTGTTGGGATAAAATGGTGAACAATGTTTTGGAGC
             CTTTGGCAGTGTATGGGGGTGGGGACAGGGACACAGAACCATTTCCCAGACCGTGGCACC
             TTTTTATTTATAGTGCCTGTTAATACCCTCCAAGACATTTTAGGAGCATTGTTATAGTT
             TGGTTAGAAATAAAGGAAAATGCTTATTTTGTTTCTCTCTTCATTTTCCTTGCCTGTTAT
             AGACTGTCTTTTGTTATATTATCTTTTTACTTTAAAATATTTTGATGAAATGGAAACTC

47193   AAATTGAAATTAATCACTGGAGCATTTGAACCAAATATCCTTAAGTGTTAAGAACCAAGT
             GCTCAAAATATCATTTTTAAGTCTTGGATCTTTGGTAGAAATTAAACTGTATTCCACATG
             CTAAGTAGGACGGCAGGAGGGTAGCTACTGAGATCAAGAGTGAGACTACTTTAGGAAAAA
             GATGACAAAGTAAAAAAGATTAGAGTTTAAAAATCTTCTAATAAAGTTGGTATGTACTA
             AAATATGAATTTGGAAGTCAACTCCGCAAAAAAGGATAGGTCTAAGAGAAAATCGACTTA
             [G,A]
             GTTTTAAGACTGATTTTACAACTGAGCCATTTGGTGACCTAGACAAATCCTTGGGAACTT
             GATCTTTTATACTTTCTCTAGAAAAAACTGATGCTAGTGAAATGCATAATTTAAGAGGT
             TAGAGAAGCTGCTCTTCAAAATGCCCCCAAGTCTGAGAGTTAAATCCTTTACATAAAGG
             ACAATATGTAAAATTTTCTTTTCTTTTTCTTTTTTTTGAGACGGAGTCTCGCTCTGT
             CCCCCAGGCTGGAGTGCAGTGGCGCGATCTCGGCTCACTGCAAGCTCCGCCCCCCTGGGT

48129   ATAATTTCTTGGTGTTCAGGCCCTTGGAAAAATAAGTTCCCTATGTTGTCCAGTGTCAA
             AGTTTCTCAACCTCAGCACTATTCTTTTTTCAGGTTATTTCTTGTAATCTGTTCACTT
             GATCATTACATTAAGAATTAGATTATATTGCTATAACTACAAAGCATTTATGTTTTAAA
             AATTATGTACAATTTAGAAACAGGCATGAAAACTTAGGTATTAAATTTAGTGGAATAAAG
             CACAGAAAAAAGTTAAATAATGCAGTTTTATCACTTAGGATTAAACATTTATATGGGC
             [T,C]
             GGGTGTAGTGCCTCACACCTGTAATCCCAGCACGTTTGGAGGTCGAGGCGGGAGGATTGC
             TGGAGTTTGAGACCAGCCTGGGCAACAAAATGAGACCTAGTCTCTACAAAAAATCAAAAA
```

FIG. 3Y

```
        ATTAGCCAGACATGGTAGTACATGCTTGTAGCTCCAGCCACATGGGAGGCCAAGACAGTA
        GGATCGCTGGAGCGAAGGAGGTTGAGGCTGCAATGACCGTGTTTGCACCATTGCATTCCA
        GCCTGGGCGACAGAACAAGACCCTGTCTTAAAACAAATTTATATGCTGCATTCGTGAAAT

48676   GCGACAGAACAAGACCCTGTCTTAAAACAAATTTATATGCTGCATTCGTGAAATTAAAAA
        AAAATCATGGATTTAGAAATAAATTGAAGCAAGGTACATTGACAGTGTAACCTCAGCACT
        ACTGACATTTTGATCTGAATAATTCTTTGTTGTGGGGGATGCGCTGTATAAGATGTTTAG
        CTGCATCCCTGACTCCTACCTCCTAGATGCCATTAGCACCCTCCCCTCCAGATGTGATAA
        CCAAAAATGTCTCTAGACATTGCCAGATGTGCCTGGGGTAGGAGGGTTGGGGGAAGTGGG
        [G,-]
        TTTGAGAACCCTTAGTTGATCATGCCTGCAGTAGGTTGAGAAGCATCAGAAAGCTAATTA
        ATTAGACAGGAATATGTGTTTGCAGTA
```

FIG. 3Z

SEQUENCE LISTING

<160> NUMBER OF SEQ ID NOS: 6

<210> SEQ ID NO 1
<211> LENGTH: 1133
<212> TYPE: DNA
<213> ORGANISM: Human

<400> SEQUENCE: 1

```
gcggggcgga acagatcgca gacctggggg ttcgcagagc cgccagtggg gagatgttga      60
agttcaaata tggagcgcgg aatcctttgg atgctggtgc tgctgaaccc attgccagcc     120
gggcctccag gctgaatctg ttcttccagg ggaaaccacc ctttatgact caacagcaga     180
tgtctcctct ttcccgagaa gggatattag atgccctctt tgttctcttt gaagaatgca     240
gtcagcctgc tctgatgaag attaagcacg tgagcaactt tgtccggaag tattccgaca     300
ccatagctga gttacaggag ctccagcctt cggcaaagga cttcgaagtc agaagtcttg     360
```

-continued

```
taggttgtgg tcactttgct gaagtgcagg tggtaagaga gaaagcaacc ggggacatct    420
atgctatgaa agtgatgaag aagaaggctt tattggccca ggagcaggtt tcattttttg    480
aggaagagcg gaacatatta tctcgaagca caagcccgtg gatccccaa ttacagtatg     540 cctttcagga caaaaatcac ctttatctgg tcatggaata tcagcctgga ggggacttgc    600
tgtcactttt gaatagatat gaggaccagt tagatgaaaa cctgatacag ttttacctag    660
ctgagctgat tttggctgtt cacagcgttc atctgatggg atacgtgcat cgagacatca    720
agcctgagaa cattctcgtt gaccgcacag gacacatcaa gctggtggat tttggatctg    780
ccgcgaaaat gaattcaaac aagatggtaa aaatggaat aagatagctt aatagagttt      840
atactaaaaa gtgttcttgg tcctcctaag tttgggaagt gttgggataa aatggtgaac    900
aatgttttgg agcctttggc agtgtatggg ggtggggaca gggacacaga accatttccc    960
agaccgtggc acctttttat ttatagtgcc tgttaatacc ctccaagaca ttttttaggag  1020 cattgttata gtttggttag aaataaagga aaatgcttaa aaaaaaaaaa aaaaaaaaa     1080 aaaaaaaaaa aaaaaaaaaa aaaaaaaaaa aaaaaaaaaa aaaaaaaaaa aaa          1133
```

<210> SEQ ID NO 2
<211> LENGTH: 257
<212> TYPE: PRT
<213> ORGANISM: Human

<400> SEQUENCE: 2

```
Met Leu Lys Phe Lys Tyr Gly Ala Arg Asn Pro Leu Asp Ala Gly Ala
1               5                   10                  15

Ala Glu Pro Ile Ala Ser Arg Ala Ser Arg Leu Asn Leu Phe Phe Gln
            20                  25                  30

Gly Lys Pro Pro Phe Met Thr Gln Gln Gln Met Ser Pro Leu Ser Arg
        35                  40                  45

Glu Gly Ile Leu Asp Ala Leu Phe Val Leu Phe Glu Glu Cys Ser Gln
    50                  55                  60

Pro Ala Leu Met Lys Ile Lys His Val Ser Asn Phe Val Arg Lys Tyr
65                  70                  75                  80

Ser Asp Thr Ile Ala Glu Leu Gln Glu Leu Gln Pro Ser Ala Lys Asp
                85                  90                  95

Phe Glu Val Arg Ser Leu Val Gly Cys Gly His Phe Ala Glu Val Gln
            100                 105                 110

Val Val Arg Glu Lys Ala Thr Gly Asp Ile Tyr Ala Met Lys Val Met
        115                 120                 125

Lys Lys Lys Ala Leu Leu Ala Gln Glu Gln Val Ser Phe Phe Glu Glu
    130                 135                 140

Glu Arg Asn Ile Leu Ser Arg Ser Thr Ser Pro Trp Ile Pro Gln Leu
145                 150                 155                 160

Gln Tyr Ala Phe Gln Asp Lys Asn His Leu Tyr Leu Val Met Glu Tyr
                165                 170                 175

Gln Pro Gly Gly Asp Leu Leu Ser Leu Leu Asn Arg Tyr Glu Asp Gln
            180                 185                 190

Leu Asp Glu Asn Leu Ile Gln Phe Tyr Leu Ala Glu Leu Ile Leu Ala
        195                 200                 205

Val His Ser Val His Leu Met Gly Tyr Val His Arg Asp Ile Lys Pro
    210                 215                 220

Glu Asn Ile Leu Val Asp Arg Thr Gly His Ile Lys Leu Val Asp Phe
225                 230                 235                 240
```

```
Gly Ser Ala Ala Lys Met Asn Ser Asn Lys Met Val Lys Asn Gly Ile
            245                 250                 255
Arg

<210> SEQ ID NO 3
<211> LENGTH: 48763
<212> TYPE: DNA
<213> ORGANISM: Human

<400> SEQUENCE: 3
gggtgacgga gtgagattct gtctaagaaa aagaaaaaa aaagaggtgc ttgataaata      60
gtagctatcc attattggcc ccgggaacaa gaagtaagtt atgtttgggg aaggaaaaaa    120
gaacaaatgt gtattaagca agcctgtagc tctaattatg tgctggtgtg cgtgtgtgtg    180
tgtgtgtgtg tgagagagag aacacatctc cagttctgtc tactgtagaa ttaggagagt    240
acaaaaagga ctttacatat ataaatagaa catacacaca cacacatgcg tgcacacata    300
tacacacaat ttaatcatta tgaaaccaca tccatattgt tgctacctag gttaagaaat    360
agatcacagc agcaccccaa caccctgaaa ggcctccatc ccaaccccag gtaactacta    420
ttctggctgt tgcttcttt atggttttgt cattacttta aacaatgaca aaaactgcaa    480
tgatttgcat caacctaata catccctcct taaacaatgt tgctttgttt tgtcctgttt    540
tggaacttat aagaatggaa tcataatgga atcatatgtt attttcttgc ttccttcatt    600
aggccttgtt ttgagactca ttatgtcatt gtggttagtt gcagtttatt cttttttcatt   660
gcttgtgaaa acactgcaat atacaatttt gtcttttcta ctgctgatgg acatttatat    720
cacttccagt tttttgcgaa cactattttg tattcttata cacatctctt ggtgtacata    780
agtaggagtt tctcgccggc gtggtggctc agggcctgta atctcagcac tttgggaggc    840
cgaggtgggc agatcactcg aggtcaggag ttcaagacca gcctggccaa cacggtgaaa    900
ccccatctct actaaaaata caaacaattg gcatggtgg catgcacctg taatcccagt    960
tacttgggag gatgagacaa gagaatagct tgaacctggg aggtggaggt tgcagtgagc   1020
cgagatcgtg ccattgcact ccagcctggg agacagagca agactccatc tcaaaataaa   1080
taaataaata ggagttttc ttaggtagag aaactacacc tagcaatagt catagaatgc   1140
acaaatcttc aatgttagca ataatgcca aacttttttt tcaaatttca aagagattgt    1200
atccatttac acgcctacgg gtactgtata agtgtgtgta cttccacatc ttcgcaaaca    1260
ctgtcacatc cttttgttgt tgttgttctc gaatttgagt gttattcttt ctcactgtga    1320
ctttattttt catattttct gattatgaac gaggttgaca actttcacac atttgttggt    1380
catctggatt ccttttttgg tgaagtgcct gtttaagtat ctcgtctata atttattta    1440
aagtgtcctt tcagacagtc tcaatgactg tcaccaactc cttgcagggc agtcagcccg    1500
gagatagagt aatcaaggta ggttgaagtc aagctcaaaa cattcgctgc ctcagctgta    1560
gcagaggacc actgggcttc cccaggtaac aagtacttct accttagcca catgagagag    1620
aaagaagacc aggcagagca gcctggctgc cttcctcctt gcaggtggcc gagagcaggg    1680
gacagcgccc tggcgacctc ctcagggatc ctagattaac agtcgcgtcc tcaaacgcag    1740
catcctgcgt aaccgccaat ttcaaacttc caagacctgc cctgctgatt ttgcccttcc    1800
cttttttccg ttggtcgcga gtcaaaggaa gatgcaattt gattggctct cccttcact    1860
ttcctccatg cctttaggga catgggcggg gcctggctga gacgcccatg tctatcatag    1920
gagcggagac gctgattggt ccaaacacgg ctgagacccg cccgcgccgt tcctcgggtt    1980
```

```
caaacgcggc ggcgggaggc gcggggcgga acagatcgca gacctggggg ttcgcagagc   2040
gtgagtctga tcccccagac ccaattctac cgcacccggc tctgcaaggc caggggaggg   2100
ccgcctccac ccatacaagt cccgggtttc cctcccgccc cggggagggc ggcgattcca   2160
cccccagggc tgcgggaggc ctggagggtc ttccggggct agctgtgcgc gcgcccacct   2220
tccttgggag ccgaggggtc agccgagtgg tgctgggca ggaggcttgc tcctccccta    2280
aaccaggcgg agtgctttgt ctcttcagct ctgcctcctg tcagcactaa ctgcattatt   2340
ctgcccagtg tagtcggccg gttccttatt atctgcgtga acttagccat ttacttaacc   2400
tctctgtttc agcgtattca taccccgtgc ccaccccatc acctcatgat gccccgcct    2460 ctttcgctct gctccagtcc gtctggcctc gctgttgctg gagaggccag gtcctgcctc   2520
agtgcttttg gcttggctgt ttcgtttgcc acggatgtct ttctttcccc agatatcaac   2580
atggcttgct ggtcattcgc ttcaggtctt caagtcttgg gtcaaatggt ggcttctcag   2640
tgaagtctta tttgaccaca ctaaaaattg caccatctca ccccattgt ccttttcttg     2700 ctcgatttg ttttttaccc catagcactta acacttaca caagctata tattttgctt      2760 atttcagtca ttcatttaat aactattcgc acctatttgt gtgccaggct atgtgtgccc   2820
ccactgcatg ggggcaaaca tctctgccct tgtggagctt ccattctaag gggggagata   2880
ataaacacat ttataagtaa gagagtatgt cagataagtg tatcatctcc tgtcacagtg   2940
agttaaaatc tggtgtttaa tctccatgat tagactgagc ttcctaaaac tggagtggta   3000
gctgattttc acctccttgt ccctgatatc ttgagggaga tcaggatctc tcaggccctt   3060
cctgctcaaa acataggaca cacttgactt ttctgatatc ctttcagcgc cagtggggag   3120
atgttgaagt tcaaatatgg agcgcggaat cctttggatg ctggtgctgc tgaacccatt   3180
gccagccggg cctccaggct gaatctgttc ttccaggtaa cagcctaccc tgccaacttt   3240
gctcacctgt gtgtgtcctt ggaatctcct tgtcactcac ctttgctttt atttatttgt   3300
ttatttattt agagtctcag tctctcaggc tggagtacag tggtgcaatc tcagctcact   3360
gcaacctccg cctcctgggt tcaagcgatt ctcctgcctc agcctccaga gtagctggga   3420
ctacagccgc ctgccaccac acccggctaa attttgtatt tttcttttta gtagagacgg   3480
ggtttcacca tgttggccag gctagggtcg aactcctgac ctcaagtgat ccacctgcct   3540
tggcctccta aagtgctggg attacaggca tgaaccgtgc ccagcttgct tttattatag   3600
gaccagggat aatattttag gggaaattct gttttgtttt gtttgaaaca aggtcttctg    3660
tcgactctag gcctgtgcca ccatgcctgg ctaattttt aatttttgt agggatgggg     3720 tctcactgtg ttgcccaggc tgatatagaa cacctgactt caagtgagcc tcttgccttg   3780
gcctcccaaa gcactgggt tataggtgtg agccactgca cctggccctc tatttagagt     3840
tttatatgca ctgattcttt tggaaaaaag acactgtgca gaagtagata gctgaacttg   3900
ccttagaagg gagatctttt catatttctc acactttaca cttctgtact aaagtttatt   3960
cattcattga ttgattggtt gcttgcaaga cagggtcttg ctctgtggct caggctggag   4020
tgcattggca caatcacggc ttactgcagc cttgacctcc tgggctcaaa cgatcctccc   4080
acttcagctt cctgagtagc tgggaccaca ggtgtgtgcc accatacctg gctaattttt   4140
gtattttttg tagagatgag gtttcaccat gttgcccagg caggtctcga attcctgggc   4200
tcaagtgatc tacttgtcac agcttctgca agtgttgggc ttacaggcat aagcccctgt   4260
accagggcaa gtttgtcctt ttattgaaga aagaaaaata aatgaacaaa gatgcttttt   4320
```

```
aaaactacaa tttctgtggg tataatccta ttcattttca ttgcaggat gtttatttt    4380
taagatttt tttttttttt tttgagacag agtcttcgct gtcgcccagg ctggagtgca   4440
gtggcgcgat ctcggctcac tgcaggctct gccccccggg gttcacgcca ttctcctgcc  4500
tcagcctccc acgtagctgg gactacaggc gcccgtcacc tcgcccggct aattttttgt  4560
attttttagta gagacggggt ttcactgtgt tagccaggat ggtatttttt aagattttaa  4620
aaaaagtttt gatgaatacc acacctgttt aaccctcatt cctctcaaga tacacatttc  4680
tgtcacccca gatgcgttaa aacttaatat cataagatta cttccaaata gatttttaat  4740
tcttttgttt ctgatgtatg tggaacactg gtgaagtaga aatccttgtt tgatttatgt  4800
attcgtaagt caggggggaca atagagacca tgaagattta gaattgaatc ccagtcccag  4860
cactagttag ctgcattact ttgggtgagt cagttacctt ttctgagtcc atttgctatt   4920
ctttaaaata ggttgtagcc tgtaatgcca gtattttcgg aggctgaggc gggcggatta   4980
cttgaggtca cgggttcgag accagcctgg acaacgtggt gaaaccctgt ctctactaaa   5040
aatatagaaa attagctggg catggtggtc gcatgtacct gtaatcccag ctacttgaaa   5100
agctgaagca ggagaatcat ttgaacccgg gaggcggagg ttgtcgtgag ccgagatggt   5160
gcactgcact ccagcctggg cgacagagtg gtaagactc catctcaaaa caaaacaaaa    5220
caaaagaaaa caaaaaaaat aacatagagg ttgtagtacc taatccacag ggttgttgtg   5280
aggattagat gagatattcg atttaaagca cttagcacct tgcctggctc ttagtaaact   5340
ccttataaaa aatggtaatt attgttaata ctcagcatag aatagtatta gttataatat   5400
taatactaaa tttgtttcct taatagtaat tatatttggg aaggtagtta tgtaggatac   5460
ctgtaagatg atgaatgatg aagtattctt gataactttt ttttttttttc caaaatattg   5520
gtattgggtg tttaaacaga tgagagtgga aacaaattga aagcttaggt ttttctgtgg   5580
gaccatcccc atcagcattt taagtcttga catatctttc acaaatgaat agtctgtctt   5640
taaccttaga tggctggagt gctgccacgt ttcagcccct ttatcatgct actttaaaat  5700
atctccaact tgctgggcgt ggtggctcac gcctgtaatc ctagcaattt gggaggctga   5760
ggtgggtgga ttgcttgagg tcaggagttc gagagcagcc cgggcaacat ggtgagcccc  5820
tccgttttcta ctaaaaacac aaaaaatagc tgactgtgat ggtgtgtgcc tgtagtccca  5880
gctactcggg aggctgaggc aggaggatca cttgagccct agaggcagag gttgcagtga   5940
gctaagattg tgccactgca cttcagcact tcagcctagg cgacagagca agaccctgta   6000
aattaaaaaa aaaaaaaaaa agaaaaggaa aaaaatttcc aacttattaa gggcttatag   6060
tgtgctgatt atgtaatagt tatggcttcc aatgtgtctg gcatagaact ggcatgtttc   6120
tgagtatctc acttcagcct catgacagag gtaaggacta tttttaattt aaactttaaa   6180
taggaggcaa caggccaggt gtggtggctc acacctgtaa tcccagtact ttgggaggct   6240
gaggcaggtg gattgcttga gtccaagagt tcaagactag cctgggcaaa atggtgaaac   6300
cccatctcta caaaaaatat aaataattag tcaggcatgg cggtgtgtgc ctgtagtccc   6360
agctactcag gaggctgagg tggggcatc tctgggccc cggaggcaga ggttgtagtg    6420
agttgagatt gcaacactgc actccagcct gggcaacaga acgagaccct gtttctaaat   6480
aaatacataa ataggaggca acagatatag acagatatgg aggtaggtaa ggccttgccc   6540
aagatcatac acgttgggtt ttgcagatga ggccaagatc agactccatc tttggttggt    6600
ctgactccaa aggctgacca catagccatt gggcacagc acctgtgcac gtcagaattt   6660
attaagtata tcttgtattt agtcattata acaggaagac ttatgggtaa accctcagtt   6720
```

```
catctctttt taatgctgag atcccectgc ccagtaaagc tattattgca agtatagtat    6780
atacctatca tttgccttga gttatcaggt aaggatgctg tttgttcttt tcccatatag    6840
tgctgtttga atgaggttga gatacagtag caattttgtt ttccattcag gtgagtacct    6900
tagactgagt gtcattttgt cttttttact tctactcaac aggatttcct gacatgttcg    6960
aggtcagtga ttgtcagact ttctgagcca gcaaaatttc ccaaattgct gggtagacac    7020
aggttttcca acttttatt ttgccaagta aggatatata aaaaaaaat aaaagaaag      7080
acctattatt ttctggccct tgtatttcat aaagggcatt ttaagaaaca caagacagg    7140
aagaacatca tctcagaata aaggaccatt tttaaatttg aatacattta gttttataaa    7200
aaagatatca tgtggtgttc atttttctc atttcactgc aggctgttga aaactttgtt    7260
aagaaccagt actatatttg ggaaccectg ctttaattga tctaaactct tgaagaatag    7320
aagaaacaaa gcatttatt tttctgagtt actggcaact attactaaag tgacagatat    7380
ggtggccttg aatgcagtgc ttcccaaacc tgattgaggt ctgactctct ggggaccag    7440
ggtctcattc tgttgcccag gctggagtgt ggcagcacaa tcttggctca ctgcagcctt    7500
tacttcttgg gctcaagtga tccttctacc tcagtctcac aagtggctag gactacagga    7560
ccatggcact acacctggct aattttttt tgtttgtttg tagagatggg atctcgctgt    7620
gttgccctgg ctggtcttga actcctgggc tcaagtgatc ctcccaccctt ggcctcccaa    7680
agtgctagta ttccaggtgt gagccacctc tccctgctgg ggaacttgtt aataaaacag    7740
attctaggct acagtctgga aaattctaat tcatttggtt gtggggagg ggggcatagg    7800
accagagaat gtgtttgttt gtttgttttgt ttttcttaaa ttctccagtg ctgttgtgat    7860
tcaaatgcag ccggtctgtt tctgttatca agtgctgtgt aacaaagcac tcacaaagtt    7920
taaagcaaca atgatttatt ttttcttagg attctgtggg ttggctggac tcagctaggt    7980
agttctgctt catcctgtga tgtcagctgg ggtcacttgt ggggctacat tcagctggga    8040
ttatgtctgg gactggaaca tgtgggtgct gactgctggc tggggcacct tagtgttct    8100
cacatggcct ctcttctcca tgaggtctttt cagtagtata gcccaggact cgtaacttt    8160
tttttttttt taagacagac tgtcgccctg tcgcccaggc tggagtgcag tggcacgatc    8220
tctgctcact gcaacctccg cctcctgggt tcaagcaatt ctcctgcccc agcctcccga    8280
gtagctggga ttacaggcac gtgcctccac gcccggctaa tgtttgcatt tttagtagag    8340
atggggtttc accacgttgg tcaggctggt ctcgaacttc tgacctcgcg atccgcctgc    8400
ctcggcctcc caaagtgttg gaattacagg tgtgagccac tgcacctggc cgactcgtaa    8460
cttttttttgt aagtaataaa tattttaggc tttgtgggtc ctgtagtctc tgttcaacc    8520
actcaacttg gccatggtag cacaaaagca gctaaagaca atatgtaaat gatgggtgta    8580
gctgtgttcc agtaaaactt ataaaagtc cgtgggctgg atttggtcca agggctacag    8640
attgcacacc cctggtctag cccaagcatc tgtgcatggt ggctggcttc ccaaaagtgg    8700
aagctgctaa gctgccttt ttttttttt ttttttttt gagagggagt ctcactgtgt    8760
tgcctaggct ggagtgcggt ggtgtgatct cggctcactg caacctccat ctcccgggtg    8820
caggcaattc tcatgcctca acctcccagg tagctgggat tacgggtgcc taccaccacg    8880
cctggctaat ttttgtattt tggtagagac agggtttcac catgttggcc aggctggtct    8940
caaactcctg acctcaagtg atccacccgt cttggcctcc caaagtgctg ggattacaga    9000
tgtgagccac cgtgtctggc cgcttgacaa gcttcttaaa ggcactgccc tgaactggca    9060
```

-continued

```
cagtgtcact tgtgtcacat tcttttggtt gaagagagtc tcagagatgg cacagattca    9120
aaggcaggag aaatagactc cagcgcttaa agtaaggagt agcatgtgcc tacagaattg    9180
gaggaactgt tggaggccat ctttgaagag agaccaccac tatccatggc ttggcacgtg    9240
ggaatcactg ctctatacca gggttgcaga ctcatgtctt tgggggccag gcagtgagta    9300
taaatgagtc aagtgggcca gttggaagat ggagtcagac ctgcagtgaa ctcccaaaca    9360
catctgctac cgggaggggc agcattactc agctccagct cagcgtcatc aggcaggaag    9420
gcgaggcagt gttgccggat gtgccagtgt ttcaaaagaa gccagagact ccattttttat   9480
ttttttgtat ggaatctcct gattttgaaa tattggcaga taattcaaat tatcttaaac    9540
actacaggcc aaacaaaaca tatctgtggg ctagagacag tctgccagtt tgtaactatt    9600
tctccagatc atgagtaaat ttggctttac gatggtcact cagttcttat tactctaggt    9660
tgttcaaatg aattaaaaaa gctgaaatta tatgaataaa cccctgggca cacatgaaag    9720
aagtgaaaaa cccattgttt cctattgtag aaacatggaa gcatgtcaga gccagaggat    9780
ccagaggaaa tattctcact agcctcagac cctcaggagt gagggagctt ttcttgttaa    9840
tggccacgct tgtgcagttt tccttcccag gtgctggtga agaaaccca cagtcttgga     9900
atcatggaag tgataccata atgactgtca gttgacgttg ctttaaagaa tgaagccaca    9960
gaattgtgct gttagcatgt cgtgagcagt tagttgagtt ggtggcttgt aatttactct   10020
gtgtggatgt tattgatcaa agcttttcat tattgacagt gtctccatct gctgtttgct   10080
gttttttaggg gaaaccaccc tttatgactc aacagcagat gtctcctctt tcccgagaag  10140
ggatattaga tgccctcttt gttctctttg aagaatgcag tcagcctgct ctgatgaaga   10200
ttaagcacgt gagcaacttt gtccggaagt gtaagtttgg ggaactttt cttgaaaact    10260
gtcctgagag agaaaaacta gaaagatgct tgaggcagaa tgagttactg gttgatagta   10320
gtcggtaaga actctggttc tatataagac agatccaggt tcaaattcag gctgcacctc   10380
ttatagctgg gagaccaggt aagttgggct tcttggttgc aagcgacaaa cttaattcaa   10440
agactgaatt taggccaggt gcaatggctc atacctataa tctcagccct tgggaagct    10500
gaggtgggtg aatcgcttga gcccaggagt tcaagaccag cttgggcaac atggtgaaac   10560
cccatctcta caaaaatac aaaaattagc tgggtatggt ggcttgcacc cgtggtccca    10620
gctgctgagg aggctgaggt gggaggatca ctggagcccg ggaggttgag gctcaatgag   10680
ctgtgattgt gccattgcac tccagtctgg gtgacagagt gagaccctgt gtgaataaaa   10740
gagtgaattt attggctcat gaaactgaga aatccaggaa tgagttaagt tttagcttta   10800
ggcatagcta gttccagaga cctcaataat atcccgtggc cctgtcctta tactcactca   10860
gggctgactt tctattaggc agagtaggca cggtgcttag gatctgtgat atttaatttt   10920
aatgaattta attacttta attaactgaa ttaaatttta atttgtttta aaattatagg    10980
aaaaatgaat ataataatgt ataatgattc tggattacat tcatctttat actaatgtag   11040
tcataaaata taattttgt ttttttgga gacagagtct tgccctatta cccaggctgg    11100
attgcagtgg tatatcatgg ctcactgcag tttcaacctt ctaggctcaa gcaatccttc   11160
cacccagtg gctgggacta caggctcaca ctaccacgcc cagctaattt ttgctttttt    11220
ctctgtagag atagggtctt actatgttac ccaggctggt ttcaaactcc aggcttgaag   11280
cagtcttcct gcctcagcct cccaaagctt tgggattaca ggtgtgagcc accatgcctg   11340
gccccataaa atataatttt tgaattcttt tttgtttta atggaggaag gggctgagga    11400
aggcaaaagt acctagggcc tatgaagtca tatattggcc ttgccttcac cctgtttctg   11460
```

-continued

```
actttgcttg acttccatgt gatgaggcag ttggctgtta gtgtcccagt ttcatactct    11520
tacattagtg ttttttcaacc agtgggtgat ttgacgtttt cggttgtcag agctagttgg    11580
gggtggtggt gtgtgagttt gggggaagg gtcctactgt cagttaatgg gtgaggccag     11640
agatgccacc aaacaccttca cagtgcacaa agcagccccc ataacacaga attatgtagc    11700
ccacaatgcc aacagtgctg aatttgagaa accccacctt gtacaacatt gctgtgcaac    11760
caaccaccct aaatattact gacttaaaac aatagtcact gtggctgggc gcggtggctc    11820
atgcgtgtaa gcccagcgct ttgggaggct gaggcggcgg atcacttgag gtcaggagtt    11880
ccagaccagc ctggccaaca tggtgaaacc ttgtctctac taaaaataca agaattagct    11940
gaatgtggca gcgggcgcct gtaatcccag ccatttggga ggcagaggca ggagaatcgc    12000
ttgaacctgg gaggtggagg ttgcagtgag ccaagatctc accattgcac tccagcttgg    12060
gcaatgagtg agactctgtc ttaaaaaaaa aaaaagtta ttgtattacc tcttgtgtgt     12120
gtaggttaat tggactcagc tggggattcc tctgctctgt attacattgg ccaggattgc    12180
agtcacctgg ggctctcctg ggctggaatg tgtgagaggg cttactcagt gtttggtgcc    12240
ctggcttgga ggctgggccc agctgggcct ctctctcttc atgaagtttc agggcctttt    12300
gctgtccaca tggcacctct atgtggtctc caaatcagaa gtcaaggaac tacagcctgt    12360
gatgcctatt ttgtaaagaa ggttttactg gaacacagcc ctacccatgt gtttgtacag    12420
tgcctatggc tgctttcaca tcataacagc atttattcc attttattta ttttttttg     12480 agacaaagtc tcactctggc tggagtgcag cagcacaatc atagctcact gcagcctcca    12540
actcttgggc tcaagcaatc ctcctgtctc agcctcctca gtagctagta ctacaggccc    12600
atgccaccac taatggctaa tttttttaatt ttgtgtagag atgggacctt gtgagattgc    12660
ctaggctggt cttgaactcc tggcctcaag aaatcctccc accttggcct cccaaaatgc    12720
ttggattaca ggcatgagcc actgtgccca gcccacaaca gcatttgagt agttgtgata    12780
gagaccaaat ggcctacaaa gcccaaaata gttcctgttt ggcccatttc gaaaaggctt    12840
gctgacctct gagctacatg gtctctctag caggacagcc tcgacggtag ctcaggtttc    12900
caaaacacaa aagtggaagc tgccaggctt tcttaggggt tatcctagga gggacatagg    12960
atctctttga ctgcatttta ttgtttgatg catgctctgg ggctgctcaa attccacctg    13020
agaggaaact acacaaggtc atgaatccca agaggactgg ggcattgggt gctatttttg    13080
gagactggct accacaccct gcccaatggt aatcttccct tatctagatt aatacaaccc    13140
cagggaagat tctaacttgg ctctgctttg ggtcatttgc ctccctggag gtgaggtgtt    13200
gtgatcggtt ttgttggaat gcccaaaggg gtcagggcag tgtgattacc aggacctcat    13260
ggaatggggg atgcgtggtt atgcaaagga gccggggatg ctgggtagaa aaaaaatcag    13320
catatgttca ctatagtgct cttcagtatt ttacatgtac tttgttctca gttttctcat    13380
ctgtaaaata ggaataatgt atatccttttt tttttttttt ttttggagt cttgctctgt    13440 tgtccaggct ggagtacagt ggcacaatct cagctcactg caacctccgc atcccgggtt    13500
caagtgattc tcctgcctca gcctcctcag tagctgggac tacaggcgtg caccaccaca    13560
ctcagctagt ttttgtattt ttagtagaga tggggtttcg ccatgttggc caggctggtc    13620
tcaaactcct gacctcaagt gatctgcctg cctcggcctc cgaaagtgct ggaattacag    13680
gcatgagcca ccacgcccat tgggaataat gtatatctaa tgaggctgtg ttggaattga    13740
atgagttaat gcacagacca gatttgtcat gttgcctggc ccataggaga caataaatgg    13800
```

```
tacccagtat taataactgt gaatgtcaac aacatttaat atattgtata tcttcaaaat   13860
gtacttgagg tatttgttca tcattctgtt tttgtttgaa taagctcgtg ccttcttttt   13920
gtgaatattt aaatttataa gtagcgagtg ggagggaag gaagttatgt gatgaggcta    13980
gcttactgag ccatctgcag gcaccttcat tagtcttgag actgtcctct ggttacttaa   14040
cagcagtgaa ttatctagaa tcatttagtg atcagaagac ttggtttagt ggaatgtaga   14100 ttttttttcta atagacccct cttccaggga aatgtttcat attttttgaag ggtttcctg   14160 gggagtgttt aagaggccat gattgaaaat gggtgattac attagtgtgt tttctattcc   14220 tcccctttt gagtttctgt tttggaatgt aagctttgtt tttctacgtg gagaagggtc    14280
cctcagctgc ttctgcccag gttttttgaa tcttcctata gggatggaga ttttctttgg   14340
ggactgttag agaaaatgga atagagtgta gctctgaagg agaaggatgt ctccagcaga   14400
agtacctcta gccttgggcc aagggaggga agggaaggga acgagcatct gggaaccagg   14460
gaagggattt ttgtctttct taattactct tacatcccca gtgcccaaaa tagtgtctgg   14520
catatgttaa gtccttagta aatacttgtt gaatgagtgt atgctcagtg aacaaaataa   14580
atggcaaaca ttaagcacag tatcagataa tttgtgtaaa aaatatacag cagtgttata   14640
ctaaaacttg cacagaggcc aggtgcagtg gctcacgcct gtaatcccag cactgggagg   14700
ccgaggtggg cagatctttg agctcaggag tttgagacca acctgggcaa catgctgaaa   14760
ccctgtctat acaaaaaata caaaaagtag ctgggcatg gggacgcaca tctgtggtcc     14820
cagctacttg ggaggctgag gctggagaat tgcttgaagc tgggaggtgg aggttgcagt   14880
aagccaagat tgtgccactg caccccagcc tgggtgacag agtaagaccc tgtctcaaaa   14940
cacaaaacaa cacccccttc aaaaaaaatc caaaccacc accacaacaa aaaaacttac    15000
acagaaaagt gttgataatt gtcaaaattg ggctgttatt ggcaatttga cagtagctga   15060
attactacca ttttgagctat attcactata gataagatct tcaatatatt tacaactta    15120 gtactaatgg gaaaatgata acttttgaaa agttttttt ttttcttatt gcaaacaata    15180
cacaatacaa tgttaaatat agaaggttaa acgtgcatct gagtctgttt gggctgcgat   15240
aatagatacc ttagacttgg caatttataa acaatagaaa ttcattgctg acagttgtga   15300
agactgggaa gtccaagatc aaggcgccag cgaatctggt atctggtgat ggctccctgc   15360
ttcaaaaatg gcgccttctt gctgcatctt cacctggcag aaggggcaaa catgagtcct   15420
tcagcttctt tttttttttt tttctatgtt taaaactttt ggtccggcgt ggtggctcat   15480
gcctgtaatc ctagcacttt gggaggccga ggcaggtgca tcatgaggtc aagagatcga   15540
gaccatcctg gccaacatgg tgaaaccccc ccgtctctat actaaaaata caaaattag    15600 ccaggcatgg tggcgtgtgc ttgtagtccc agctactcag gaggctgagg caggagaatt   15660
gcttgaacct gggaggcaga ggttgcagtg agccaagatt gcgccactgc actccagcct   15720
ggcaacagag taagactccg tctcaaaaca aacaaacaaa aaaacaaaa aaaaactttt    15780 attttaggtt catgggtaaa tgtacaggtt tgttatgtag gtaaacttgt cttgggttt     15840 gttatagatt atttcgtcac ccaggtacta agcctagtaa ccaatagtta ttttttcaga   15900
ttgtctccct cctcccaccc tctgtcctct agtaggctcc aatgtctgtt gttcccttct   15960
tagtgtcctt gtgttctcat cctttagctc ccatttatat gtgagaacat gtggtatttg   16020
gttttctgtt cctgcattag tttgctaagg ataatgtcag cctctttttt ttttttttt    16080 ttttttttga tacagagtct cgctctgttg cccaggttgg agtgcagtgg tgcgatcttg   16140
gctcactgca acctctgcct cccgggttca agtgattctc ttgccttagc ctcctgagta   16200
```

```
gctgggacta caggtgcgca ccaccatgcc aggctaattt ttgtatttta gtagagatag   16260 ggttttcacca tgctggccac gctggtctcc aactcttgac cttgtgatcc gccggcctcg   16320 tcttttttccc aaagtgctga gattacaggt gtgagtcact gcacccggcc caatgtcagc   16380
ctctttttta gggaagtgat ttaatcactt ccctaaaagt cctacctcgt tttttttttt   16440
ggttttttct tttttttttt tttttttttt tttttttttt taggtagagt cttgctctgt   16500
cacccaggct ggagtgcagt ggtgcgatct tggctcactg caacctccac ctcctgagtt   16560
caagcaattc tcctgcctca gcctcctgag tagctgggat tataggtgcc tgccaccacg   16620
cctggctaat ttttttgtat ttttagtaga gttggggttt caccatgttg gccaggctgg   16680
tcttgaactc ctgacctcaa gtgatctgcc caaaatgctg ggattacagg cgggagccac   16740
tgtggccagc ccctgcaagt cctacctctt aatagtatta cactggggat tacatttcaa   16800
catgaatttt gtaggggcga ggggcacaaa cgtttagaat atagcacatc acatacatag   16860
tgagagaaaa atccctcaaa atcttacctg agacaatcac tgccaacaga ttgctgtata   16920
gtgtgccaat tttgtttgtg tgtgtgtgtg ccttaaaaat atttattatg gaatttaaa    16980 aacgtacccc aaggtggcca ggtgtagtgg ctcacgcctg taatcctggc actttgggag   17040
cccgaggtgg gtgtattact tgaggtcagg agtttgagac cagcctggcc aaaatggtga   17100
taccagtctc ctaaaaatac aaaaattagc cgggtgtggt gggcacctgt agttccagct   17160
actcgggaga ccaagtcatg agaattgctt gaaccctgga ggcagaggtt gcagtgagcc   17220
aagaccatgc cactgcactc cagccagggt gacagagtga gactccatcc tagaaacaaa   17280
caaacaaaca aacaaaccaa ctaaccaacc agagaaaact ccctgtctgt aaggagtatg   17340
tgttctaatg gatactgagc catcttgttc tgtttaacat gtgcctaatg ttcttttata   17400
tgggcggact tgtaggttgt ttcaactttt ctgttgatga acctttaggt ggtttctgat   17460 tattttgtg ttacaacagt tttcatcatt cacatctttg tatgcatctt ttttgagcac    17520
atgtgcaagt atttctgtgg acaatggatg attcctagaa attgaaagtt tggattactg   17580
tgttccaaaa aaggaagcaa tacacccagc tatgttggct tttgctcttg ggtccagatg   17640
attatctgac aaagttattc tctgattgca ttttctttttc ttttcttttc ttttttttt    17700 ttgagatgga gtttcgctct tgttgcccag gttggagtgc aatggcgcga tctcggctca   17760
ctgcaacctc tgcctcccag gttcaagcga ttctcctgcc tcagcctcct aagtagctgg   17820
cattgcaggc atgcgccacg acacctggct aattttttgt attttttagta gagatgggat   17880 ttctccatat tggtcaggct ggtcttgaac tcttgacctc aggtgatcca cccgcttcag   17940
cctcccaaag tgctgggatt acaggcgtga gccacagtgc ctggcctct gactgcattt    18000 tcacagtgtt ttgggtcctt atctctacct cagtacctca atattcagtg cccactgggc   18060
ccttagatac tgcagctaaa agtgcacagg ggtggagtga tgtgacggtt ttggggtcac   18120
agaagcagct ggtatagaga gaagttgtga agttttttttt ttttttcctg agacagagtc   18180
tcgctgtatc ccctaggctg gagtgcagtg gcttgatctc ggctcactgc aacctctgtc   18240
tccctggttc aagtgattct tatgcctcag cctcccgagt agctgggatt ataggcatgt   18300
gtcaccatac ccagctaatt tttgtgtttt tagtagagat ggggtttcac catgttggcc   18360
aggctggtct tgagctcctg acctcaggtg atccgcccac ctgggcctcc caaagtgctg   18420
ggattacagg cctgagccat tgcgcctggt cttttttttt ttttttaag taatcatagg    18480 cttgaatgta gcctctcatc tgttcacctt aataatccaa aagcctttag ataaagaaat   18540
```

```
ggagatttgg aatggcttct cagaattcca agagagtatt gtcatggttt tgcctgcaaa   18600
gcaccgtggt ctgtctcctt gtgcagttga gaaagctggt ggtcgccact gacaggccca   18660
gagttattaa gttggacact gctttaagca actttgtaaa caatccaagg catactagag   18720
aattaggaga gattggcttt gtgtatgagc aataacaaaa tcaagttcaa tccagcaagt   18780
ttttggggaa ttataattca aaactcaaat acttgatctg gaagaaactt ggaaagaggg   18840
aaggaagaca ggcttgttac agcattgtca gggtaaaagg aaaataccgt gcagcttttq   18900 attttgcttc ttcatggcat tccccatgta ggtgccctag atttgttttt tacagtggtc   18960
acgacttcat gtggatccac ccaccactct tgcctggttc cccaagggac caagggaagg   19020
tgtattcagg atgattgctg aagtgagggg tggggtctgt ggctgagaag actctcaata   19080
ccgcggcact cattataagc ctctgacaca ggagatttca actccacccg tgcaacaaag   19140
gaacagggtg ggcaagagta gttacagttg caggctgagt gcgatggttc atgcctgtaa   19200
tcccagtgct ttgggaagcc aaggtgggag gattgcttga gtctaggagt ttgagaccag   19260
cctgggtgac ataatgagac cctacctgta caaaaaaatt ttaaaaatta gccagattgg   19320
tggtgtgcgc ctatagtccc agctactctg gagaatgagg tgggtgaggg tcccttgagt   19380
ccaggagttc gaggctgcag tgagttatga ttctatgatt tcaccactgc attccagcct   19440
gggcgacaga gcaagattgt gttcttttt ttttttgaga cggagtctca ctctgtcacc   19500
caggctgaag tgcagtggta cgatctctgc tcactacaac ctgcacctcc caggttcaag   19560
tgattctctc cctcagcctc ccgagcagct gagattaaaa gcggccgctt gtgtgcagct   19620 aattttgta ttgttagtag agatgggggtt tcatcatgtt ggtcaggctt gtcttgaact   19680
cctgacctca ggtgatccac cgcctcgcc ctcccaaaat gctgggatta caggcgtgag   19740
ctactgcgcc cagccatttg tgtctcttaa aaaaaaact aagaaatga aaaaatgac    19800 attggccaat tcattaaaat gccactcact gactgtggta tgaaatggct ttcccttga    19860 tggaccgagt ctgtctcatt gtgtgagcca cttgcagggc tgagtatgac tctggaatgt   19920
agctcctaac cttatctgct gcccagccat tgaaatggcc atcccttcca gttcccagaa   19980
gattccagtg tgtgtttggg attttaagac agtctcttgg tcttcagtgt ggcatctttc   20040
tgccggattt tccaggataa ttttgattat aagcattgca ttgcccttgg tgtgtaatgc   20100
ctgtgtatga tgctgttccc ttgtaacgtg caggattaaa tttttgggtc agccactgct   20160 gctcccttc attcctgcag gtcattagag tcatcgtaca tttagcgatg tctcagatca   20220
gtgtatctag agtgttaata acatgttag attccaaatc tactgtccat ttaatccata   20280
cttcatacgt tgaggatctc tgactgaaag attagacttg gaaaaataat aagactgtat   20340
ggtaagaaaa ctatagttgc aaatccattt ggacatgtag tatgtcagcc ctgcagagca   20400
gatgtcagaa ccccatttag ttctctgagt gctaagccct tctgcccacc acgctgtttt   20460 tttttttga gatggagtct cgctctgtca ctcaggctgg agtgcagtgg tgtgatctcg   20520
gctcactgca agctctgtct cccaggttca cgccattctc ctgcctcagc ctcccaagta   20580
gctgggacta caggtgctca ccaccatgcc cagctaattt tttgtatgtt tttggtagag   20640
acggggtttc actgtgttag ccaggatggt ctggatctcc tgaccttgtg atccaccgc    20700 ttcggcctcc caaagtgctg ggattacagg cgtgagccac tgctcctggc ccccacgcct   20760 ttttttttt ttggagacag agtttcactc tgtcacccag attggagtgc tgtggcacaa   20820
tctcagctca ttgtgtcctc tgcctccag gttcaagtga ttcttgtgcc tcagcctcct   20880
gagtaggtgg aattacaggc gtgcaccaca cacctggct aattttgta tttttagtag   20940
```

```
agatggggtt tcaccatgtt ggccaggctg gtctcgatct cctgacctcc agtgatccac   21000
ttgcctaggc ctcccaaagt gttgggatta caggcgtcag ccaccatgcc tggacccctc   21060
tgccccttta agcactgcca catattagat ctacgaaggc tttatggata caatccaagg   21120
aagatgaacc ttgggctagt gggataaaac taagcgcatg tagttagaat ggaatgatct   21180
ggaaaccagg tcccaagttg gtctaaatta gactcatgtt gactatgtca cactgtaaac   21240
cagtctaaat gctaataagc atgcttgacc aaacactgcc ctgcagcctt cagagaggaa   21300
gaaggaaaac ataatttgta tcctctctcc ctattttctg agtctatggg attcaaattg   21360
tagctgccat ggaaactgta ctttggaatt tctagagccc ttaattttaa cttaacatat   21420
aaaaacactt ttgtactgat tttataatta ttcatgatgg atgagaaagt gaatgtcttt   21480
gacagtgagg gaagctatcc gaatgctatt ttctttttt ttttctttc ataaagatgc   21540
atatatttgc atgctttatt tacctggggc taactcttgc atcttttgca gattccgaca   21600
ccatagctga gttacaggag ctccagcctt cggcaaagga cttcgaagtc agaagtcttg   21660
taggttgtgg tcactttgct gaagtgcagg tggtaagaga gaaagcaacc ggggacatct   21720
atgctatgaa agtgatgaag aagaaggctt tattggccca ggagcaggta ggaggatttt   21780
aacatcatgc ttttccactt tctgtaccgg agtgttcatt gcaaagacga taatctgctg   21840
cactggcgtc taggatcaag cacgttttcc tctgtgactc tatatttaat tatagttggg   21900
gcaaaaaggt ctctcatgtt cttagctcat cttcttgaac tgatgttggc taattttgaa   21960
ggctcacaaa ttcctcttga tgtatcatgt ttctatcgtt gtaatttatt tcagaaccaa   22020
ggtggccttt tagctaatga atttaagatg atcttttatg accattagct gaggactcag   22080
gatatacata tggtggggtg aatcagattg cttttgtaca cgctttaggt atttgtgttg   22140
tgggcatatg gatttggttt taaaacaggc ctttgaagaa atcaaataac attctttgtt   22200
atgtggctag ggagttgctt gtttgagagc aggtagaacg ttatctttt tgttgtggta   22260
tttttctttc ttttaaacaa ggctactgtc tctagacata ttgattcatt tgctgtgttt   22320
tagagagatg gccgtcagcc ttggaattca gagagtaatt tattacttac agacatttta   22380
gtgcacatga tatgtctgat aatgtaccca gctctgcagg aagcttgcaa aaggaataga   22440
agtcccatgg ttgctatttt cagtgtttaa aaacaacctt ggaaagtgga ggaaaaatgc   22500
aaatgtataa agcaggtgct taccagctaa agtatcacag aagtgggaga gcaattagca   22560
aattaattaa cgatgatgtg aggggagatg ttgtgggtga gcaagggaca gttagggaca   22620
gttctcaccg atgggggaa atgtaggttc tcggcagaga gaagtgatga gaacatgttg   22680
ggtagaagtg tgacattctg gagtactaga atgctatgca agtgtgtgtg tgtgggtgtg   22740
tgtgtgtgtt cagtggttca gaacagactg ggaaatggcg aaatgaggac atttgggtgg   22800
ggaggggaa atgggtggga aactcaagaa ccttttttta aaaattgtg gtaaaatata   22860
tataacataa agtgtaccat tttaaccatt tttaaatgtg caactgagtg gtattcagtg   22920
cattcatgat gttgtacaac catgaccgct ctccatttct agaattttc tatcatccca   22980
aacagaaact ctctatccat tatacaatac ctccccattc ccccaagaac cagttttga   23040
attgcagttt actttgtgag gctgttgggg attatttagg cctctggaag gaggaggttg   23100
ggatcagagt ctggccctgt ggacttcaat gactttgtgt ggcctccaat cagagaagca   23160
gcggagggca ggaagctgct tgtcagaatc tgagagtgat gtggcttctt tgtttagcaa   23220
taaaatgtga gcacataata gaaaggaaaa gtgacaggac atggcagata atttggaaga   23280
```

```
gaggagtgga agatgctcac tcagcctccc agctcctgag aaagaactgt gtctcatcag     23340
ttcatactac ctgagcatct gttgtatctg gtgtgtttct aggtcctgga agagaggcat     23400
tacgtgtagc cctgaccttg tgatgcttat gttttgatg ggaaatagtg cgtgtaaaaa      23460
gaaaataatc aacaggcca cacggcaggc aaacaataga gatattcaaa taggtatacc      23520
ttcctccagg tgaatggcct gaaatgaccg tgtggaagtg tgggctgggg cttataaaa      23580
ttatacacat acaggcgcta actaaagccg cctattcatt ccttaagagg atgcatagaa     23640
aagaaaagta gggtccttaa ctgagccatt tggaatttaa gggcatgaga gaagccagca    23700
caagcagtga agggaaggaa aagaagtgcc cgagaggagg gagggatgct gttctgcaga    23760
caaggcctgc cgcctgggag aggcccgcac gcccacccag ggttctctga cagctggaag   23820
gggtcttcag agactgttta tattttattt atttatttat ttatttattt tgagacagag    23880
tctctgtcac ccaggctgga gtgcagtggt gcgatctcag ctcactgcaa gctccgcctc     23940
ccaggttcac accattctcc tatctcagcc tcccgagtag ctgggactac aggcgcctgc    24000
cacaatgccc ggctaatttt tttgtaattt tagtagagac ggggttttac ctcgttagcc    24060
aggatggtct tgatctcctg acctcatgat tcgcccacct cggcctccca aagtgctggg    24120
attacaggtg tgagccactg tgcctggccg actgtttcta ctatttaga gagagggtct     24180
cactgtcatc tgtgctggaa tgcagtgatg cagtcatagc tcactgcacc ctcaaactcc    24240
tgggcttaag cgaccctccc gcctcagcct cttaagtagc tgggaccata ggcatgtgct    24300
gccacaccca gttaactta tttatttatt atttattag agaatgagtc tcattctgtt      24360
gcccaggcta gaggtgcagt ggcacgatct cggctcactg caaccccgcc tcccaggttc    24420
aagcgattct tcttgctcag cctcctgaat agctgggatt acaggcacct gccaccacac     24480
ctggctaatt tttgtatttt tagtgcagag gggggttttc accatgttgg tcaggctggt    24540
ctcgaactcc tgaccttgtg atctgcctgc ctcggcctcc caaagtgctg ggattacagg    24600
cgtgagccac cgtgcccggc ccactttatt attttaaaa cattgtttta tttttatttt    24660
tttgagacag agtccgctgg agttcagtgg ccggatctca ctcactgcaa cctctgcctc    24720
ctgggttcaa gtgattcttg tgcttcagcc tctctagtag ctgggactac aggcgggtgc    24780
caccatgcct ggctaatgtt ttttgtatct ttttagtaga cgggggttt tgccatgttg     24840
gccaggctgg tctcgaactc ctgaccttaa gtgatctgcc cactttagcc tctcaaagta   24900
ctgggattac aggcgtgagc cactgtggct agccccagc taactttaaa aaaaattt     24960
gtgggccggg tgcagtggct cacgcctgta atcccagcac tttggaggcc aagcagggcg   25020
gatcacttga ggtcgggagt ttgagaccag cctgaccaac atggagaaac cctgtctcta    25080
ctaaaaatac aaaaaattag ccgggtgtgg tggtgcatgc ctgtaatccc agctacttgg   25140
gagctgaggc aggagaattg cttgaatctg ggaggcagag gttgcagtga gcttagatca    25200
cgccactgca ctacagcctg ggcaacaaga gcgaacactc cgtctcaaaa aaaaaaaata   25260
aattatgtag aggtgggatc tccctatgtt gcccggactg tcttgaact cctggcctca     25320
agtgatcctt ccatctcccc ctcccaaagt gttgggatta caggcatgag ccacccctcc    25380
tggctgagac tgcttatttt atttattttt aattttttt gttttgagac tgcttatttt     25440
aatggaagct tcagggtca dacggggtca gacagagtca ttggtgagca agcaaaggtg     25500
tagactgttc agttcagcct tccttggaca cctttatgt gccagacaaa agaaggatca     25560
gcatatcagg tgcagtaaat tattgggtt atgttggtgt ttcccaaatg tgttagattt    25620
atccctggta gtgttaaatc tcatgatttt aggtagtata tggacaacct atgtaaaaac    25680
```

```
atttaatagt ttaatattaa ctagcatatc aaaacctgtg actttgctca cgcctgtaat   25740
cccagcactt tgggaggcca aggcgggagg atggtttggg cccaggagtt tgaggccagc   25800
ctaggtaaca tggtgagacc ctgtctctaa aacaaaacaa aacaaaacaa acaaacaaac   25860
aaataaacaa atcccctgta acttgttcta acaataacct aaacaattt ttatttaaaa    25920 ttaaataaaa aaattgaaac agtaaccatt tttttttttt tttttggaga cagagtcttg   25980
ctttgtcacc tagtctagag tgcagtggca caatctctgc tcactgcaac ctctgccttc   26040
aaacaattct cctgcctcag gcttctgagt aggtgggatt gattacaggt gcactccacc   26100
atgcccagct aattttttgta tttttagtag agacggggtt tcaccatgtt ggctaggcta   26160
gtcttgaact cctgacctgc agtagtccac gtgccttggc ctcccaaagt gctgggatta   26220
caatcacaaa tttatagaaa agttgcaagt accatgtagt cagggttctt aagagaaatg   26280
gaaccagtag gagatagata tataatcatc tcctaggatt ataagttgac acataagact   26340
aaccgtcaca tacagtataa acaactttt ttcttaaacc atttgataga tacacacaca    26400
ctgatataca tagaatatat atacacacac acagaatgta tatacacata gaatatatgt   26460
gcatacagaa tatatacaca gaaatatata tgtacacatg catagaatat atttacatat   26520
atatgcatat atataattta tttatttta gcagttgatt tatacagttt ttgttttttgt    26580 tttttttttg agacagagtc tcactctgtc acccaggcta gagtgcagtg gcgagatctc   26640
agctcactgc aacctctgcc cccgggttcc agtgattctc ctgcctcagc tccacaagta   26700
gcacaccacc atgcccagct aattttttgta ttttttttag tagagacgag gtttcatcat   26760
gttggccagg ctggtctcga actcctgacc tcaagtgatc cgcccgcctt ggcctcccaa   26820
agtgctggga tttcaggcgt gagccaccac acctggctcc cataatgtct tttagaataa   26880
aacgatcgag ttgaggatca cacgtgacac ttaattgtcc tgtctcttta gtctccttca   26940
atctggagca gttctttgat ttttcctgga ctctcatgac cttgacaatt ctgatgatta   27000
taggccagtt attttgtaaa atttgaattt gtctgatgtt gcttatgttt agatttaggg    27060
tcttggtctt tggccggaat atctcagaca agatgctctg ttcttattgc atcagagcag   27120
aagactctct gtttcagttg atcacattta tgttgatgct cactttgatc acttgattaa   27180
ggtggtgtca gttatgcctt tctacttgta gggttactcc ttcctccttc gtgattttat    27240
ttattttatt tttcttagag acagggtctt gcttggttgc ccaagctgga gtgcagtggt   27300
gggatcttgg ctcactgcag ccttgaactc ctgggctcaa gtaatccacc tgccacagcc   27360
tcctgagtaa ctgggactgt aagcgaacac caccacaccc agctactttt tgtattgtag    27420 agatgggtc tcactgtgtt gtccaggctg gtctgtaact cctggcctca agcagtcttc    27480
cggccttggc ctcccgaagt gctgggatta caggcatgag ccactgcacc cagcctcctt   27540
tgtaattaaa aaagtatttt atgggagtt acttcaagt gatggaaata tttatatct     27600 atgtggactt ggattttcct atttcagtca gtgagttata atccatttct gtcactagtt   27660
ttatacttaa attgttccca acttggccac tgagaacctt tttaggttag cttttgtgtc    27720
cttttcacat gtctccaaga ttcattgaat actttcctgc tttctggtat agcaagatgt   27780
tcaggttctt ttggtacttt tacttctct gccctggctc tggcatcagt catttctcag    27840
aggagccctg tgcctttcag tggacaatgg tgtttagagg ccaagatctg acattgggt    27900 gttttcattg ctaccggtgt gtcactactc ccagacccct ttcagtggac agcactaagg   27960
aatacacata cgtatataca atatatccac ctacacatgt gcgtgcactc acacacacac   28020
```

```
atatacatta catctatatt tgtgtatcca tgtctatata ttgaaaattg tggctgggca   28080
cagtggctta tgcctttaat ctcagcattt tgggaggctg aggcaagagg atcacctgaa   28140
gccaggagtt caacaccagc ttgggaaaca gagagagact ctgtctctac aaaaataaaa   28200
agggaaaacc atgagttcac acccgtgccc ccagttccaa tccaacttca cagggttcat   28260
tttagttttc acccttttcca tgtttgtaat tctcttctct gacattatac ccttaatatg   28320
tttacttatt ttatgcatct gtatgcatcc aatctactgt ctttgttggt atcccacctc   28380
cccttggtgg gtccagataa tctgctctgg gttgcccttt cacgtggatg tcttccttac   28440
cctgtgtggg cctgtgatac tgggctgccc ccacacatga gtgctgccct cctcacgttg   28500
cttgggacgg cactgtgtcc tgggccacca tgacttttct cataactagc gtggatgctt   28560
accttgttcc acaccagtga atggcttcag gaagagaaga ggaagagaaa aatatttaca   28620
tttaaagaaa ggtagtttaa agaaatatgt taggtaaaga attgagcagg taatatacgg   28680
agctggcaaa aattgtgacc aaagtaggtg aatgattgag atttatgcaa ttctgggcta   28740
agtgacagcc cctcccttt ccttcccttt ccccttccct tccttttct tccctttccc   28800
ttccctttcc ttccctttcc cttcccttc cttcccttt cttcccttt cctcttctt    28860
ccttccttcc ttctgttttc tttcccttc tttcctttgc cttttttttt tttttaaagc   28920
tagaaacatc agtttaggca taaagacaga ggaaaaggct tcttttttcct ctcacagttc   28980
tttataattg tctaagcagt ttctttttc cctaggtttc attttttgag gaagagcgga   29040
acatattatc tcgaagcaca agcccgtgga tcccccaatt acagtatgcc tttcaggaca   29100
aaaatcacct ttatctggtg agtctttaca tctgtctctc tggaattagc ctagcactct   29160
gacactcaga tgcctgtggt agaactgaat gttgttcttg cccatgtggt ctcattcatg   29220
caaagacttt cttaccttac aggtgtctcc ctggtttcct cgttataaag atcaagagct   29280
aacccattta gaaacagcct cattgggctg aacgtggtgg ctcacgcctg taatcccagc   29340
attttgggag gccgaggcgg gtggatcacg aggtcaggag atcaagacca tcctggctaa   29400
cacagtgaaa ccccgtctct actaaaaata cagaaaaatt agccgggcat ggtgtcgggt   29460
gcctgtagtc ccagctactc aggtggctaa ggcaggacaa tcgcttgaac ctgggaagcg   29520
gagcttgcag tgagccgaga ttgcgccact gcactccagc ctgggtgaca gagcaagact   29580
ctatctcaaa aaaaaaaaaa agaaaaaaaa agaaacagcc tcattgacag ttggatattg   29640
tagctgtggc tttcaggcaa taatagggaa tcatttattg gggaatagtc tgtcattatg   29700
tataagataa tcttgctttta atttttaaaa acttcctgtg ttagcttgct taggattaaa   29760
aaaatgataa tagtgcatgg ttgttataag aaaatgcaaa cactgcagac atgcatgaag   29820
ttgaagggaa agccccccat tttcttttcc ttttcttttt ttttgagaca gagtctcgct   29880
ttgtcaccca ggctggagtg cggtggcact atctcggctc actgcaatct ccacctccca   29940
ggttcaagag attcttctgc ctcagcttcc ctagtagctg ggattacagg cacgtgtcac   30000
cacgcccaac taattttgt atttttagta gagatgtgggt tttaccacgt tggccgggct   30060
ggccgcaaac tcctgacctc aaatgatcca cctgcctcgg cctcccaaag tgttgtgatt   30120
acaggagtga gccactgtgc ccggcctctc cgttttattt tctaatcctc ctccctaggg   30180
gaagaaatgt taaatggtta cataagcttt ccctttctga cccttaactg tgctctgtag   30240
gagcatggtg ggggatgttt cttttctttt cttcttttt tgagaccagg tctcactttg   30300
ccacccaggc tggagttcag tggcatgaac atggctcact gcagcctcga cttcctgggc   30360
tccagcaaac ctcccacctc agcctcccgg gcatacacca ctgtgcctgg ctaattttg    30420
```

-continued

```
tattttagt agagacgggg ttttgccatg ttgcccaggc tggtttcgaa gtcctgagct   30480
caagagatct tcctgccttg gccttccaaa gtgctgggat tacaggtgtg agccaccatg   30540
cccagctccg gtgggggata tttctatatc cacatgtgta tagtttactt tataaaaatg   30600
gtatgttact ctgtgcttgg ctctccagct tgctgttgcc tttcaccagt gtatcccaga   30660
catcctttct tccttgtcag taacgcaggt ctactttatt ctttgagcag tggcataatt   30720
ttccctgatg tgtatatatc ataagttaga gaatgctaaa attcattttg gggccttgtt   30780
taggttcttg agggattaaa ttcctaaatt taacaagtgt atcctggaaa caattttgt   30840 tcctgattca gcccttaaaa gaggactatc atgttacctt gaatggagat aaacaggctc   30900
acgtaagaga aaagggtaag agggatgaac tcccacttat cttaaacttc tactggcccg   30960
tttttgggga atttgctgct tttattcctg acctaaaata aataagttta tgtgtcttgg   31020
tttcatatta gttgagaacc cagtgcctgg agagaagttt tccttgtcct ctgagtgagg   31080
acattcacat atgaatctat tggcagactg gctttgactg accacacgtg ccttcagaac   31140
caatgccaca gctcttaggt ttatggcctg aaacaccctt tccttacata ttgccttaga   31200
aactttcctt ccttgagaca tggggcatgg aaccctcacc ttcacagatg accttggtgt   31260
gtttctaggg ttgctggtgt tccaggacat ctgttgcaga tgcagtattt accttgtgct   31320
ctctgcatca taagcagctt ctcatgtttg aatgtattaa cagactttta atttttttta   31380
tttttgagac aaagtctcac tctgtcaccc aggctagtgt tacccaggct ggagtgcaat   31440
ggctcaatct cagctcactg caacctccac ctcctgggtt caagcgattc tcttgcctca   31500
gcctcccgag tagctgggat tacaggtgca tgacaccacg ccctgctaat ttttgtattt   31560
ttagtagaga cggggtttcg ccatgttggt ggggctggtc tcaaactcct gacctcagat   31620
gatctgcccg ccttggcctc ccaaagtgct gggattacag gcgtgagcca ctgcgccttt   31680
tcttttcatt ttttttctga gatggagtct ttctctgtca ccaggctgga gtacagtcat   31740
gcaatctcag ctcactgcaa cttccacctc ctgggttaaa gtgattctcc tgtcttagcc   31800

tcctgtgtag ctgggactac aggcgtgtgc caccgtgccc agctaatttt tatattttta   31860
gtagagacgg ggttttgcca tgtgggttag gctggtcttg aactcctgac ctcaggtgat   31920
ccacccgtct tggcctccca agtgctgggt gttataggcg tgagccactg tgcccagcct   31980
caggcttctt tattaagaag aagttcgggc caggtgtggt ggcttacacc tgtaatccca   32040
gcaatttggg aggccgaggt gggcagatca ggaggtcagg agatcgagac catcctggct   32100
aacatggtga acctcgtct ctactaaaaa tataaaaaat taggcaggta tggtggcggg   32160

tgcctgtagt cccagctact cgggaggctg agggaggaga cggtgtgaa cctgggaggc   32220 ggagcttgca gtgagcccag attgtgccag tgcactccag cctgggtgac agagcgaggc   32280

tccgtctcaa gaaaaaaaaa aaagacgttc cttgaaaca acagggcttt tgtttgtttt   32340 ggtttgtgtt тgтттgтттат tgttgttta gatacgtatt tttttctttc tttttttttt   32400

ttaagtgatg atgtctctgt tgcagtggca tgatcatagc tcactgtaac ctcaaattgc   32460
agggctcaag tgattctcct gcttcacctt cctgattagc tgggacaaca ggtacaaacc   32520
accatgccta gcgaattttt aaatttttca tagagactag ggtctcacta tgttgcctag   32580
gctggtttcg aactcctggc cccaagtcat cctcctgcct tggcttccca aattgttggg   32640
atcacaggca tgaatcacca cacccagcct atttttagat атттттааттc gagctctaca   32700 ggaggtttag aacactagct tgtgaagata aacttcattt tcaaggccac acagaatcta   32760
```

-continued

| | | | | |
|---|---|---|---|---|
| agtggtcctg | gaattaggaa | gggctttgat | tttttggacc | aaagttgaga gtccacagtt | 32820 |
| ttctggtcta | ccttgcactg | ctccataaac | tcatatttct | tttctctgag ctgaagagct | 32880 |
| cccccttcttg | gtgtctagtc | tcaggcaact | tattcttaaa | agtaagcatt attgaaatgc | 32940 |
| tttgggattt | tcacatcatc | aaggtccatt | ttggtagagg | cactgacaga ttttgagtgt | 33000 |
| tctgtgtgaa | ggaactcagt | tgaggattta | gtggtccatg | tggcaggcta ctgctcagta | 33060 |
| gcttcaggga | aaccactgct | tgcctcccct | gtggccagtg | aggatgatca gaggagtccc | 33120 |
| agcaggaatg | cccaaatgta | gttttcttac | atgttgatgg | gagtgcattg tttcatgtct | 33180 |
| aaacagttct | caaatcacat | cttcaggagg | gtactatctg | ggcactttga taatttctca | 33240 |
| ctttgatgtc | accgttctta | ttaccatcac | ctagttttgt | catagtagaa ataacttttcc | 33300 |
| tttttctgtg | tgtgtgtgtg | tgtgtgtgtg | tgtgtgtgtg | tgtgtgtttt gagatggagt | 33360 |
| cttgccgtgt | tgcccaggct | gtagtgcagt | ggcgtgttct | cggctcactg caacctctgc | 33420 |
| ctcccgggtt | ctcctgcctc | agcctcccga | gtagttggga | ttacaggcgt gtgacaccac | 33480 |
| gcccggctca | ttttttgtatt | ttcagtagag | atgggggtttc | accactttgg ccaggctggt | 33540 |
| cttgaactcc | tgaccttgtg | atccgcccac | cttgacctcc | caaagtgctg ggattgcagg | 33600 |
| tgtgagccac | cacgcctggc | tttttttttt | tttttttga | gacagagtct tgctctgttg | 33660 |
| cccaggctgg | agtgcagtgg | cgggatcttg | gctcactgca | gcctccacct cctaggttca | 33720 |
| agcaattctt | ctgcctcagc | ctcctgagta | gctgggatta | caggtgccca ccaccatgtc | 33780 |
| cggcaaattt | ttgtattttt | agtagagaca | gggtttcacc | atgttggcca ggctggtttc | 33840 |
| taactcctga | ccccaggtga | tccgcctgcc | tcagcctccc | agagtgatgg aattacaggc | 33900 |
| atgagccact | gcgcctggcc | acctttgtct | tcttagttgt | ggatttaact gctgtggaca | 33960 |
| tctgcttggg | catagccttc | ccggagtacc | tcttggattg | ggactgtctg tgggtttctg | 34020 |
| tgctaggaca | ggctcccaga | tgtaggaggc | ttccccaatg | atctcaccac tggcatcggc | 34080 |
| atccttagct | tctactcagc | ttttccatct | gccatcttgc | aagatggaag gttgttttgt | 34140 |
| ttttgttttt | gttttttggt | ttattttttt | tgagatagag | tctcgctctg ttgccaaggc | 34200 |
| tggagttcag | tggcgcaatc | tcggctcagt | gcaacctcca | cctcctgggt tcaagtgatt | 34260 |
| cacctgcctc | agcctctgga | gtagctggga | ttacaggcgc | gtgccaccat gttcgtttaa | 34320 |
| ttttttgtat | ttttagtaga | gacggggttt | caccgtgtta | gccaggatgg tctcgatctt | 34380 |
| ctgacctcat | gatccgcctg | cttcagcctc | ccagagtgct | gggattacag gcgtgagcca | 34440 |
| ccgtgcccag | cctaggaggg | ttcttaatgc | agctgttttt | tggagttctg gttgcctcag | 34500 |
| cacactgcta | cttgggtcaa | tgacattttt | actcccttgt | tttgtagctc aattgggtat | 34560 |
| tactgatggg | atttttgtaat | tattaatatt | ttcttgtctc | cattttcttc tcaagtactt | 34620 |
| tgttgctttt | gagtaaaatg | cttgctaagg | gtatagtttt | cacataaaag ctcaaattta | 34680 |
| gcatggaaat | taagatatgc | tcatacgtct | gccatccctt | atctgtaatt ctgaaatacc | 34740 |
| tagagttctg | aataacctca | aattctttg | ttacttgttt | atcagcaaaa cctgatttga | 34800 |
| actcagtttt | tggcaaaact | tgatccaagc | tctcttaagg | ctctttttag tctttattca | 34860 |
| ttcccttag | tgtgacttcc | cattttgcta | taaaattatg | agtgtgtttg attacaaggt | 34920 |
| gatgtcccag | accctactga | gggtgttaca | taatataaac | tgtatgtatg gctgggcgcg | 34980 |
| gtggcttata | cctgtaatcc | cagcactttg | ggaggccgag | gcgagcggat aaccttagtt | 35040 |
| caggagttca | agcccagcct | ggccaacatg | gtgaaacccc | gtctctacta agaatacaaa | 35100 |
| aattagccag | gcatgatggt | gggcgcctgt | aatcccagct | actccttagg ctgaggcagg | 35160 |

```
agaatcactt gaacccagga ggtggaggtt gcagtgagcc aaggtcatgc cactgcactc    35220
cagcctgggc gacaaagcaa gaatctgtct caaaaaaaaa aaaaaaaaag tgtgtgtacc    35280
actttacctt tctaaaatct gaaaaattct gaatctggaa acccattctg cttcaagata    35340
aatggatcct agatttatat cggtaccgta cagtcctgaa attccatcct atctattggc    35400
cacttttaca tcaacaaacc tttgaagttt ggggaaactt acatatcacg ctcccttggc    35460
agttgaacat tatttattta ttttgagatg gagtctcgct ttgcccaggc tggagtgcag    35520
tggcgcgatc ttggctcact gcaacctctg cctcccgggt tcaagcaatt ctcctgcctc    35580
agcctcctga gtagctggga ttataggcat gcaacaccat gcccagctaa tttttgtctt    35640
tttagtagag acggggtttc actatgttaa ccaggctgtt ctcgaactcc tgaccttgta    35700
atcttccctc ctcggcctcc caaagtgctg gaattacagg cgtgaaccac cacgcctggc    35760
cctgaagata cattttaaat caatgaaaaa acaacagga ttctacctcc tatggtatat     35820
ccctcctggc tgtctcttct ctccagtctt gcctctgctg tgtgggtttc aggcatccat    35880
cttctctact ctgaattact gtgataacct ctgaagtatt ttccctgcca tctgtctggc    35940
ccttctccca ggtcttccac atactgcagc caagtcagcc cgctgttgaa acccttcaag    36000
actccctgct gtcctctgga tgaagtccag actcttccac gtgacttacc aggcttttct    36060
tgcacttgtc cccagccact tactgtttct ctctttctac cttaacatcc tgaacttcct    36120
ttggttcttt gaccttgcct ctgaccttt tccatgctgt tcactctttc cctgttcacc     36180
ttgctaactc ctcttttctct ttctgggttg gatcagattt cacttcttcc agaagccctt   36240
cctagaccct atacttctgg aatggcgcct tttgactgta cgctcattgc accctgtact    36300
tctcctttat gagtgggtgc tggtctgtcc cactaggcta cttcatccat aaagggagag    36360 tagagctttta ccaagtcaat gcttaagcaa tatttattgg atgaatgtgt gattaatttc    36420
atagaaattt gatgtgcatt caaatttact tattgtatta cggaacttgc attatattct    36480
cagtggagtt atttttcttttc acgtgtgtaa ttcaagatag actcagtgag attttcaaaa  36540
tttggaatgc agtgcaagga aattgaactt gagttctttt gcattttgat ggttaaaaat    36600
ttcccatttg tggtgacata ccacaataag ccagtgaatg tggcttattg ttttctggtc    36660
tatagaaaat tgtcgcaaac tctgtcataa tgtctggttc tatataacaa agctagtcct    36720
gtattctgca tgtggctgat ggaaacagtg ctctgttgat ctggttcatg aagaaatctg    36780
ttcaattctg cataacagat gccttcatca gtgtccttcc atgaaggagc tgatcttcac    36840
aaagaacaca tagttttgca tcccaccact tgcagtattt tttttttttt tttttttttt    36900
ttgagatgca gtctcgctct gtcaccctgg ctggagtgca gtggcatgat ctcagctcag    36960
tgcaacctct acctcctggg ttcaattgat tctcctgcct cagcctcctg agtagctggg    37020
attacaggcg cacaccacca tgcctggcta attttttgttg ttttagtaga cggagttt     37080 caccatattg gtcaggctgg tctcaaactc ttgacctcat gatctgcctg ccttggcgtc    37140
ccaaagtgtt gggattacag gcgtgagtca ctgtgccctg ccagtattgt tttgtctaaa    37200
ttatttgtgc tgatgttttt cctactgtgg ttttcttcag attacccttg ctctgagcct    37260
gcaattgact catgaacttc ttttccatgt tctaacctta caatgacttc cttgtgttca    37320
ctccaaatgt ttttccctgg ttgcatgtag agatgtatta gctaaggtac atgcttagct    37380
gctgtatcaa agagacccta atgtacaacc caggctggta gagcagctct gctgtatgtg    37440
ttaattcagg gacccaggtt ccttccatgt tgtgactccc cccttcctta ggatgttgtc    37500
```

```
ttcttttaca tggctgaagt tgggccattt catgtctctg ttccagctgc ctggtaggaa    37560
aaaagaacag aaattcagag taagcaaatt cttttttctat agatggatgc ggaagttgga   37620
cacatcattt cctctcacat tttctcggcc agaacgtagt catgtgactg cacgtctagc    37680
tgctaaggag actgggaatt tactgtcggc tgtgtggcct ctgtcaagct aaaattctta    37740
ttactgtgga ataagggaag gatggatttg ggggcacaat taatagtctg tcacagaggc    37800
taaaacagct gcttttggct gggcacggtg gctcacacat gtaatttcag cactttggga    37860
ggccgaggca gtggatcac ttgagatcag gaatttgaga ccagcctggc caacatggtg     37920
aaaccctgtc tctcctaaaa atatagaaat tagccgggca tggtggcggg tacctgtaat    37980
ccgagctact ccagaggttg aggcaggaga attgcttgaa cctggaaggc agaggttgca    38040
gtgagccaag atggtgccac tgcactccag cctgggcgac agagcaagac tccatctcaa    38100
aaaaaaaaaa aaaggttaaa taaacagctg cttttgtagg tgatacaagg tacagctaag    38160
ctttgaagcc aggcctgtag tttcaccttc catattctta ctcaaggcat tatacttctg    38220
gatctgaaac cactggatct gatgccctgc ttgggatgag ttctttatat tatcttgctt    38280
tcaacccaca cctgtgtaat tttatgggca gcgtttgttt cctatatagg aacaatttga    38340
aagtgggctg tttctaggct ttcatgaata gcaggctatg ctgtcattgg gaatctggag    38400
ggagttaatg aacacaactt cattgtttac tttagtgaaa tgtggcagct tatgatagtt    38460
ttgacagtga gacatgtgct gttttgatct ctcagctaag attatctgat ttttcaggca    38520
tgtctcaaaa ctcaccaggc ctgctcacat gctgctgctt ctgaagccag ggtttggaaa    38580
ccagctgccc atcagaatga ggctgtgact tagaatattg gttcttgttt tattaccatt    38640
ccttgtttgg tctctccaga gtcactggcc ttttccgctt caattttctt atcggtgaaa    38700
tgagatatta attcctctta ttgacttcaa ttcaattgct gagtgtattg ttgcctttgg    38760
gaggttcttt gagttttctg tgcctttgaa atagttgttt ttttttattc tggtgttttg    38820
aggcatgttt caagtgagtg catttacact tctaccattt taggagccac aattcagtta    38880
tgttgtccca gcttgcttgg ccccatcccc agagtttctg attcagtagg ctgggggtgg   38940
ggcccaataa tttgcatttc ttcttctttt ttcgagacag agtctgactg tgtcatccaa    39000
gctggagtgc agtggcacga tcgtagctca ttgtagcctc aaactcctgg gctcaagccg    39060
tcctcccacc tcaccctcct gagtagctgg gactataggc atatactacc atgccctgcc    39120
acctttttaa tttttttgtaa ggatgggggt ctcactgtgt tgctcaggct ggtcttgaat    39180
tcctgggctg aagtgatcct cctgcttcag cctccccaaa tgccggcatt cctggcatga    39240
gccactgcac ttggccaaga cttttgcattt ctaactagtt tccaggtaat gctgctgctg    39300
gtgtagggac ctcattttga gaaccattgt tctatagctg tagctatagt tagtttctgg    39360
ttatagcttc ttccttttgt cccttcagta atagtgtaca catccgaaat ccctgtcctt    39420
gctctttcag gcccaggcat ggtatctggt cctcttctgt tgctagccct ggggtgcttc    39480
atcatcccaa gttattttt cttctcctaa cctgaacctt tgtaaatagc ccttcccta     39540 atgaacgtcc tcaattccct gttttgcgtg tcctgtctgt ttcttggcaa gactctggat    39600
gattcagtac tcaatgagga ttttcgcat agatggatga acaggctgg gtttcatgtt     39660 ttctaagata aaggtgcttc tctcttttc tcttggtcac tttgaccaag aagaaaataa    39720
cagagttttt attctcaaga agaataatat cgggggccact ctgctcagag gccactctgc    39780
tttgaggacc ccttctctcc tccctcatgc caaagatcag gaacattggg cagagcggat    39840
aacgatgccg ccagcgtcat tacattttca cggcactttc agttgtgctg agcgtgcaaa    39900
```

```
catttcaagg agacatttct aagaggtggc tagcacagca tgcctctaat gccctatgtg   39960
aattggaata gagtactaaa gaactgttca atattcaccc catccccgca tatgcaagca   40020
tgcacgtggg ttcattgtat atgtgtgtgt gcacgtgtgc acagacacat ttgtccttcg   40080
tttcaaatgc aacacaatgg atggaaattg ccttcctggt actggggtat ggatgcaaac   40140
accaacagag aagcagccgc tacttccaaa ctgaacacat gtgagatttg ccctttaatt   40200
agcatctgca gctgctgcca tcagaagggt ctgtctctgt tggcctgaaa gtctttgctt   40260
taaaagcaga agtccattat agctccaagc caggctcgtc tgtcagctgc tgtgctttct   40320
ctgccatcag cggggttgcc acattgtttt gggctgtttc actctaggac tctttcctcc   40380
tcctgtgccc ccagccttg attaccatgc cttggtgatc ctcatttggg tgacctgcag   40440
ctgctcattg tgtgtgcagg agacatctcc agtccttgta aggagggaag atcactggct   40500
tcagtgctga tggactggtt attttccagc cctttgtcgt cagtgatctt gtcttgatat   40560
gcagaaaggc tccaggtagt cactgaaaaa aatataagca gcagaggtga tggctatatg   40620
aaagtcacgt ttcatcaagg gcattgctgc tatgaaaact ttcaattcac ttggagtagg   40680
gagccatatt ggttccacag cctcctcagc agtgggtccc aacacagtgc tgggctagct   40740
gcctctgaat caccgcagta gctccttttt actatagatt ctgggtccca cccatggaat   40800
gtgatccatg aagtctgggg ttattccctg gaatccttta agctccctaa gtggttggga   40860
tgggaaagag atatgcttta tgttactata cttcttctta ttattatttt aaaattcttg   40920
ccgggcgcag tggctcacac ctgtaatccc agcacattgg gagaccgagg cgggtggatc   40980
acttgaggtc aggagttcga gactggcctg ccaacatga tgaaatcccg tctctactaa   41040
aaatacaaaa attagctggg catggtggcg catgcctgta gtcccagcca ctccggaggc   41100
tgaggcagga gaatcgcttg aacccgggag gcagaggttg cagtgagccg agatcgtggc   41160
actgcactcc agcctgggta acagagtgag acttcatctc aaaaaaaacc caaaaaaaca   41220
aaactctttt tcattatacc ggaacgtcag ctttatggag tcggggattt tttctgtttt   41280
attcactgct gtttccctaa catctagaat agtggctggc acgataggca ctcaagtatt   41340
gatttagatg agtctatttt atttctttt aaatttttaa ttttttattag aggtggggtc   41400 tggctttgtt gcccaagctg gtctcaaaac tcctggcctc aagcgattgt actgcctcag   41460
cctcccaaag ggctaggata ggcatgagcc aacatgcctg gcttgtctta tttttaacaa   41520
gcacttctgg tgattctgat ggacaatcag gcttgggaag ttctaaccta gaggacctac   41580
agttgtcttg gggtagaagc caaggctatc ctggttttta gaatcagtgc cttactgggc   41640
atctctgaag agtaaaagtc agggacagag ttacattttt ggacaaaacc agatgctgtg   41700
aatggactct tggtcacaac ctgggtggcg acttggtcct taacttcttc atcattttct   41760
gctgaccctg ttctttggtt cacagcaagt cacctgataa gaagactcaa agactgctag   41820
tttgttactt tagatgatgc ttttggaacc tcttggtacc attttaacaa tccaaacgta   41880
ttttatgaaa gcactcaagt cctgggtctt tattgtatct ttaagctcta acagcatgat   41940
gattgaataa gctgtggttg gccacacaca agccatcttc cccatggcct ccattcatac   42000
tagaatgagc agctataccc cagtagtata gttttgggat atgggtaaca tcttgggata   42060
gccacattta cttagtaaat gtctggctta cattctccta atggtgcact gttggaattt   42120
ttggtgtggt aacctggaat agtgttggtg ggtcaagttt gattagcatc tttgataagg   42180
acccggtcta tttagaggtt tgtcattgag tgtgtctgtt ttggcctcat gttgtgaagc   42240
```

-continued

```
atgctgtgta gcagctgttg taattttttgt tgcttgtttt ctcaatcaac cctggttttg    42300
aagaaatggg aagttgttcc actcttagac tgatctgact tgggagggga ttttcagttc    42360
aggaagttgg atcttctgaa tggaagcaaa gaatacatgt cttttttgcca ctttacaagc    42420 tggctcttgt tttctgaact attttactgg tcattgcaaa tagaatgtca ggagtagctg    42480
ccaaatacta agttgtgttc agtttgtcag ttcttaagag ttgccggtgg ctgctctgct    42540
atgcgtatga ctttctcagc cttaaactta caagccatac tgttttttc acatctttaa     42600 tacagccata ggaaatttat aactgtggcg tgtcgtcata aatatgcatt gttcttattt    42660
taagacattt cagtactaaa agtataagta cttctgttat tatctgtgaa tttctttcct    42720
tcttcttttt ttggatattt aagacctttt cgatgtcaat atatatttaa aacagacata    42780
taaattagca ttcacccaca tacccagggc ctatggagaa ccaggttggg atgagtgggt    42840
gagctacagg cagccaggtg gctcctgtgg gctcctcgag gactggggtg agtaactaat    42900
gtctgctagg aacttggggg aaagaaggtg tgtatgttag gtgctgcccc cttctaagtg    42960
ttcctcttgt tcataatttt ttttttttt tttttttta gatggagtct cgctctgttg       43020
ccaggctgga gtgcagtggt gtgatctcag ctcactgcaa cctctgcctc ccgggttcaa    43080
gtgattctcc tgcctcagcc tcccgagtag ctgggactac aggcatgcac caccatgccc    43140
agctaatttt tgtattttta gtaaagacgg ggtttcacca tgttggccag ggtggtctcg    43200
atctcttgac cttgtgatcc gcctgcctcg gcctcccaaa gtgctgggat tacaggtgtg    43260
agccactgtg cccagcccat aaatcaaaat tttttcagca attgttatac aagtggaacc    43320
ttactcttca aatgcaattg tccagtgtct ggcttaatgt ctgctgttgt cagaaaccat    43380
gtgaatggag tagattccca ggttataagg agccccagg gaggatgcgc gagtcactgg     43440
cttctccagg ggtctctggt ttggggttgc cttggtgctg ggcacacttc ctggagattt    43500
tactggacca gcctgaggcc tttggggctc tgtgcagatg ctctacttct gacttgtcta    43560
gagctttctt ctaattctgg actaaaagca agcaggagtt tggaggatga tggtgagaat    43620
tcacatcccc gagttggctt ttggaatgca gtagtttgtg agatttagtg ttttttttaa    43680
gaagtatatt cagatcttgc cttttttccca gaaagcatat gagacaactt ccaagacatt    43740
tatagcatgg ctaataaaat gggaaatcag ggcgaaggac aggagaactc aataagggtt    43800
aacatggcta cagcgattgt ctaaatgggt tcttttttgct ggccagagca gaaaggatca    43860
tgcagtaaag tgggggggaa gaaagggaat tgaatggtag gtgaagactt catgttggtg    43920
ccaggcactg tgccaggccc tcctaggacc ttgtcttact caatcctcac acagtgctgc    43980
aagaggatta gtcttatccc tgttttagag aggatgaaac tgaaaggcag cgaggtgaag    44040
tcaccagcag gaggctgaag ccgcccaggc taactggcct tatagctacc tagggactca    44100
ggaatatcac acctgtttat catcaaaagg agaaaggatt tcagttcctt ggggtagaag    44160
agtttctttt tgctaatcaa acattttact tgaggcttca tattcttctt caagatttttt   44220 ttcctgtgta tgtaccaaca catgtaataa ttccttgttt atttcaaaaa aggggttgta    44280
ctttattctt tacaagattt cactttatat tgtcatggac aattttccat ggcagtatga    44340
ataaatggaa tctgtttgtt tttaatatct ttgtcttatc ccattgttta catatgtcat    44400
attttagcca gtctctaact gatggatagc tgaatgattt ccatgttttt ttcccctgtt    44460
acaaacaata ctgcaaggaa tctatttatc tttctattta tctgcaaact attgtaagta    44520
cctgtaaatt gttagaagtg gaattactag gtcaagggg atattttcac atttaaattt     44580
tgaatagagg ctgtcagttg ccttccacac tgactataaa aggaaaagat tgtatcacat    44640
```

```
ttattgcaag ccttctgtat tctgctgggt gctgagggga atacagaaag gatataagag   44700
tggttgccct ctaggaatat ccgtctacac tgtacctaat cctagggaat gtctggggtg   44760
tcaacttgtg ggtgggaaag tgggtggatt taattcaact gttcaagctt gccttgcaaa   44820
cactgtgcat ggtgtctggg actagtcttt cattatattg attccctgg gtaacagatg    44880 taatttcctt agggcaggga cttcatccta catgacttac agcgtgcctt acacatcttc   44940
tttgctttgt ggagaccttg ttattataac acgtcaggtg atattcgagg atctaattga   45000
ggcattccct atttttgggt gtgtgaagaa ttaataactt tggcattcta tacaggtcat   45060
ggaatatcag cctggagggg acttgctgtc acttttgaat agatatgagg accagttaga   45120
tgaaaacctg atacagtttt acctagctga gctgattttg gctgttcaca gcgttcatct   45180
gatgggatac gtgcatcggt aagtgagact ctggtagcat ttttatgctg aggattttcc   45240
tgtgtcgcat aagagttcct gcatggaaat gagtggatga gtgatttcaa gatcaagata   45300
acgccccatc cagttttag ccagtctacc aataactggc tgaaagcaaa ctttccaaga    45360
tggaggacat ttcagcttgc ttatccagca gtgcaataga tctagaattg taatgtgctc   45420
aagtttgcta gtaatatcta ttaatgtagc taaataagac tgggaactct tgcatgggtt   45480
ctttgggtta tatgatagaa gaactgaatt tggtttgcag aaggaaatgt cataccacat   45540
agtagtgtaa gaccatggag ctgtacttct ctaactctgc ccgttagaat ttacaatttt   45600
tttttttttt ttttttttg agacagagtc tagctctgtt gccaggctgg agtgcagtgg   45660
taccatattg gctcatggca acctccgcct cctgggttca ggtgattctc ctgcctcagc   45720
ctcccaagta gctggaatta caggcacgca ccgccatgcc cagctaattt ttgtattttt   45780
agtagagatg gggtttcacc aggttggcca ggatggtctt gatctcctga cctcatgatc   45840
cacccacctt gtcctcccaa attgctggga ttacaggcat gagccaccat gcctggccta   45900
caaaatcctc agttggtaag tggttcttca tgtcttcatt catctgatgt tttgtgtaca   45960
tctgagaatg ttgtgggaat acaatgattg ttagtccagg aatcacaaaa tttgagatag   46020
agtctcagct ttttccattg cctagctacat gaccttggga aaatttcata gctccttttg   46080
gccttagttt tcctcatgtg aaatgtgtgt ctctaggaga aataatccat tgaataaat    46140 gtgtttcatt tctcttcctt ttctttctct cctatccttc cttgctccct ctcgcccttt   46200 ttctcttttcc ccctctctcc ctctctctct ccttccttcc ttcctttcgg ttaaattcat  46260
tttgcaaaat gtatgctaat aatttatatc caccaataga ggaggtctat ataacagaat   46320
acataaacaa agattttggg ctcaattgag attctaggtt agcacttgct tgctgattgg   46380
gatggaggag gcaattcatg gtcctgattt tcttacagag acatcaagcc tgagaacatt   46440
ctcgttgacc gcacaggaca catcaagctg gtggattttg gatctgccgc gaaaatgaat   46500
tcaaacaaga tggtaaaaaa tggaataaga tagcttaata gagtttatac taaaaagtat   46560
tcttggtcct cctaagtttg ggaagtgttg ggataaaatg gtgaacaatg ttttggagcc   46620
tttggcagtg tatgggggtg gggacaggga cacagaacca tttcccagac cgtggcacct   46680
ttttatttat agtgcctgtt aatacctcc aagacatttt taggagcatt gttatagttt    46740
ggttagaaat aaaggaaaat gcttattttg tttctctctt catttttcctt gcctgttata  46800 gactgtcttt tgttatatta tctttttttac tttaaaatat tttgatgaaa tggaaactcc  46860
tgcatgtcaa atcctctatt tcctatgcag caaaattgaa attaatcact ggagcatttg   46920
aaccaaatat ccttaagtgt taagaaccaa gtgctcaaaa tatcattttt aagtcttgga   46980
```

-continued

```
tctttggtag aaattaaact gtattccaca tgctaagtag gacggcagga gggtagctac   47040
tgagatcaag agtgagacta ctttaggaaa aagatgacaa agtaaaaaaa gattagagtt   47100
taaaaatctt ctaataaagt tggtatgtac taaaatatga atttggaagt caactccgca   47160
aaaaaggata ggtctaagag aaaatcgact taggttttaa gactgatttt acaactgagc   47220
catttggtga cctagacaaa tccttgggaa cttgatcttt tatactttct ctagaaaaaa   47280
ctgatgctag tgaaaatgca taatttaaga ggttagagaa gctgctcttc aaaatgcccc   47340
ccaagtctga gagttaaatc ctttacataa aggacaatat gtaaaatttt cttttctttt   47400 tttcttttt tttgagacgg agtctcgctc tgtcccccag gctggagtgc agtggcgcga   47460
tctcggctca ctgcaagctc cgccccctg ggttcacgcc attctcctgc ctcagcctcc   47520
cgagtagctg ggactgcaag cgcccgccac catgcccagc taatttttg tatttttagt   47580 agagacgggg tttcaccgtg ttagccagga tggtctcgat ctcctgacct cgtgatccac   47640
tcgcttcggc ctcccaaagt gctgggatta caggcataag ccactgcgcc cggctctttt   47700
ttttcttaaa ctgcttccag aaaagtggat attattaggt tgatgttaag aaaaggcttg   47760
gagttgcatt aactttttgc tttctagcat ctggcctgtc tgttctgcag acctgagacc   47820
tacttgagat aattttcttg gtgttcaggc ccttggaaaa ataagttccc tatgttgtcc   47880
agtgtcaaag tttctcaacc tcagcactat tcttttttc aggttatttt cttgtaatct   47940
gttcacttga tcattacatt aagaattaga ttatattgct ataactacaa agcattttat   48000
gttttaaaaa ttatgtacaa tttagaaaca ggcatgaaaa cttaggtatt aaatttagtg   48060
gaataaagca cagaaaaaaa gttaaaataa tgcagttta tcacttagga ttaaacattt   48120
atatgggccg ggtgtagtgc ctcacacctg taatcccagc acgtttggag gtcgaggcgg   48180
gaggattgct ggagtttgag accagcctgg gcaacaaaat gagacctagt ctctacaaaa   48240
aatcaaaaaa ttagccagac atggtagtac atgcttgtag ctccagccac atgggaggcc   48300
aagacagtag gatcgctgga gcgaaggagg ttgaggctgc aatgaccgtg tttgcaccat   48360
tgcattccag cctgggcgac agaacaagac cctgtcttaa aacaaattta tatgctgcat   48420
tcgtgaaatt aaaaaaaaat catggattta gaaataaatt gaagcaaggt acattgacag   48480
tgtaacctca gcactactga cattttgatc tgaataattc tttgttgtgg gggatgcgct   48540
gtataagatg tttagctgca tccctgactc ctacctccta gatgccatta gcaccctccc   48600
ctccagatgt gataaccaaa aatgtctcta gacattgcca gatgtgcctg gggtaggagg   48660
gttgggggaa gtgggttttg agaacccctta gttgatcatg cctgcagtag gttgagaagc   48720
atcagaaagc taattaatta gacaggaata tgtgtttgca gta                    48763
```

<210> SEQ ID NO 4
<211> LENGTH: 251
<212> TYPE: PRT
<213> ORGANISM: Rattus norvegicus

<400> SEQUENCE: 4

```
Met Leu Lys Phe Lys Tyr Gly Val Arg Asn Pro Ser Glu Ala Ser Ala
 1               5                  10                  15

Pro Glu Pro Ile Ala Ser Arg Ala Ser Arg Leu Asn Leu Phe Phe Gln
            20                  25                  30

Gly Lys Pro Leu Met Thr Gln Gln Met Ser Ala Leu Ser Arg
        35                  40                  45

Glu Gly Val Leu Asp Ala Leu Phe Val Leu Leu Glu Cys Ser Gln
    50                  55                  60
```

-continued

```
Pro Ala Leu Met Lys Ile Lys His Val Ser Ser Phe Val Arg Lys Tyr
 65                  70                  75                  80

Ser Asp Thr Ile Ala Glu Leu Arg Glu Leu Gln Pro Ser Val Arg Asp
                 85                  90                  95

Phe Glu Val Arg Ser Leu Val Gly Cys Gly His Phe Ala Glu Val Gln
            100                 105                 110

Val Val Arg Glu Lys Ala Thr Gly Asp Val Tyr Ala Met Lys Ile Met
        115                 120                 125

Lys Lys Ala Ala Leu Arg Ala Gln Glu Gln Val Ser Phe Phe Glu Glu
130                 135                 140

Glu Arg Asn Ile Leu Ser Gln Ser Thr Ser Pro Trp Ile Pro Gln Leu
145                 150                 155                 160

Gln Tyr Ala Phe Gln Asp Lys Asn Asn Leu Tyr Leu Val Met Glu Tyr
                165                 170                 175

Gln Pro Gly Gly Asp Leu Leu Ser Leu Leu Asn Arg Tyr Glu Asp Gln
            180                 185                 190

Leu Asp Glu Asn Met Ile Gln Phe Tyr Leu Ala Glu Leu Ile Leu Ala
        195                 200                 205

Val His Ser Val His Gln Met Gly Tyr Val His Arg Asp Ile Lys Pro
    210                 215                 220

Glu Asn Ile Leu Ile Asp Arg Thr Gly His Ile Lys Leu Val Asp Phe
225                 230                 235                 240

Gly Ser Ala Ala Lys Met Asn Ser Asn Lys Val
                245                 250

<210> SEQ ID NO 5
<211> LENGTH: 251
<212> TYPE: PRT
<213> ORGANISM: Mus musculus

<400> SEQUENCE: 5

Met Leu Lys Phe Lys Tyr Gly Val Arg Asn Pro Pro Glu Ala Ser Ala
  1               5                  10                  15

Ser Glu Pro Ile Ala Ser Arg Ala Ser Arg Leu Asn Leu Phe Phe Gln
                 20                  25                  30

Gly Lys Pro Pro Leu Met Thr Gln Gln Gln Met Ser Ala Leu Ser Arg
            35                  40                  45

Glu Gly Met Leu Asp Ala Leu Phe Ala Leu Phe Glu Glu Cys Ser Gln
        50                  55                  60

Pro Ala Leu Met Lys Met Lys His Val Ser Ser Phe Val Gln Lys Tyr
 65                  70                  75                  80

Ser Asp Thr Ile Ala Glu Leu Arg Glu Leu Gln Pro Ser Ala Arg Asp
                 85                  90                  95

Phe Glu Val Arg Ser Leu Val Gly Cys Gly His Phe Ala Glu Val Gln
            100                 105                 110

Val Val Arg Glu Lys Ala Thr Gly Asp Val Tyr Ala Met Lys Ile Met
        115                 120                 125

Lys Lys Lys Ala Leu Leu Ala Gln Glu Gln Val Ser Phe Phe Glu Glu
130                 135                 140

Glu Arg Asn Ile Leu Ser Arg Ser Thr Ser Pro Trp Ile Pro Gln Leu
145                 150                 155                 160

Gln Tyr Ala Phe Gln Asp Lys Asn Asn Leu Tyr Leu Val Met Glu Tyr
                165                 170                 175

Gln Pro Gly Gly Asp Phe Leu Ser Leu Leu Asn Arg Tyr Glu Asp Gln
```

-continued

```
                    180                 185                 190
Leu Asp Glu Ser Met Ile Gln Phe Tyr Leu Ala Glu Leu Ile Leu Ala
        195                 200                 205
Val His Ser Val His Gln Met Gly Tyr Val His Arg Asp Ile Lys Pro
        210                 215                 220
Glu Asn Ile Leu Ile Asp Arg Thr Gly Glu Ile Lys Leu Val Asp Phe
225                 230                 235                 240
Gly Ser Ala Ala Lys Met Asn Ser Asn Lys Val
                245                 250

<210> SEQ ID NO 6
<211> LENGTH: 251
<212> TYPE: PRT
<213> ORGANISM: Mus musculus

<400> SEQUENCE: 6

Met Leu Lys Phe Lys Tyr Gly Val Arg Asn Pro Pro Glu Ala Ser Ala
1               5                   10                  15
Ser Glu Pro Ile Ala Ser Arg Ala Ser Arg Leu Asn Leu Phe Phe Gln
            20                  25                  30
Gly Lys Pro Pro Leu Met Thr Gln Gln Gln Met Ser Ala Leu Ser Arg
        35                  40                  45
Glu Gly Met Leu Asp Ala Leu Phe Ala Leu Phe Glu Glu Cys Ser Gln
    50                  55                  60
Pro Ala Leu Met Lys Met Lys His Val Ser Ser Phe Val Gln Lys Tyr
65                  70                  75                  80
Ser Asp Thr Ile Ala Glu Leu Arg Glu Leu Gln Pro Ser Ala Arg Asp
            85                  90                  95
Phe Glu Val Arg Ser Leu Val Gly Cys Gly His Phe Ala Glu Val Gln
            100                 105                 110
Val Val Arg Glu Lys Ala Thr Gly Asp Val Tyr Ala Met Lys Ile Met
            115                 120                 125
Lys Lys Lys Ala Leu Leu Ala Gln Glu Gln Val Ser Phe Phe Glu Glu
        130                 135                 140
Glu Arg Asn Ile Leu Ser Arg Ser Thr Ser Pro Trp Ile Pro Gln Leu
145                 150                 155                 160
Gln Tyr Ala Phe Gln Asp Lys Asn Asn Leu Tyr Leu Val Met Glu Tyr
                165                 170                 175
Gln Pro Gly Gly Asp Phe Leu Ser Leu Leu Asn Arg Tyr Glu Asp Gln
            180                 185                 190
Leu Asp Glu Ser Met Ile Gln Phe Tyr Leu Ala Glu Leu Ile Leu Ala
        195                 200                 205
Val His Ser Val His Gln Met Gly Tyr Val His Arg Asp Ile Lys Pro
        210                 215                 220
Glu Asn Ile Leu Ile Asp Arg Thr Gly Glu Ile Lys Leu Val Asp Phe
225                 230                 235                 240
Gly Ser Ala Ala Lys Met Asn Ser Asn Lys Val
                245                 250
```

ISOLATED HUMAN KINASE PROTEINS, NUCLEIC ACID MOLECULES ENCODING HUMAN KINASE PROTEINS, AND USES THEREOF

RELATED APPLICATIONS

The present application is a continuation-in-part of U.S. Ser. No. 09/804,471, filed Mar. 13, 2001 pending.

FIELD OF THE INVENTION

The present invention is in the field of kinase proteins that are related to the citron kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books,* Vol 1:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of internal Medicine,* McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks NK (1992) *Annu. Rev. Cell. Biol.* 8:463–93). Regulation of PTK activity may therefore be an important strategy in controlling some types of cancer.

Citron Kinases

The novel human protein, and encoding gene, provided by the present invention is related to the serine/threonine kinase family in general and the subfamily of citron kinases (also referred to as Rho-associated-, Rho-binding-, or Rho-interacting-kinases) in particular. Furthermore, the protein of the present invention is a novel alternative splice form of a protein/gene provided by Applicants in U.S. application Ser. No. 09/804,471, filed Mar. 13, 2001.

Rho GTPases initiate specific kinase cascades upon activation. For example, the kinase activity of Rho-binding serine/threonine kinase (ROCK) is increased upon binding to Rho. The citron molecule (Madaule et al., 1995) interacts with Rho and Rac and shares significant structural homology with ROCK. Di Cunto et al. (1998) identified a novel serine/threonine kinase, CRIK (citron Rho-interacting kinase), in a mouse primary keratinocyte cDNA library. CRIK is a member of the myotonic dystrophy kinase family. 2 different CRIK isoforms have been found: a long, 240-kD form of CRIK in which the kinase domain is followed by the sequence of citron, and a short, 54-kD form known as CRIK-SK (short kinase), which consists primarily of the kinase domain. CRIK and CRIK-SK proteins are both capable of phosphorylating exogenous substrates as well as of autophosphorylation. CRIK kinase activity is stimulated by constitutively active Rho. In keratinocytes, full-length CRIK moves into corpuscular cytoplasmic structures where it initiates recruitment of actin into these structures. CRIK is expressed in keratinocytes, brain, spleen, lung, kidney, and highly expressed in testis; Rho-associated kinases ROCK1 and ROCK2 are ubiquitously expressed. CRIK contains a kinase domain, a coiled-coil domain, a leucine-rich domain, a Rho-Rac binding domain, a zinc finger region, a pleckstrin homology domain, and a putative SH3-binding domain. Di Cunto et al. (1998) cloned a human homolog of CRIK and mapped the gene to human chromosome 12q.

Di Cunto et al. (2000) used targeted disruption in mice to generate mice lacking citron kinase ("citron-K −/− mice"). It was observed that these citron-K −/− mice grow at slower rates, are severely ataxic, and die of seizures before adulthood. The brains of citron-K −/− mice show defective neurogenesis with dramatic depletion of microneurons in the olfactory bulb, hippocampus, and cerebellum. It was found that these abnormalities are caused by altered cytokinesis and extreme apoptosis during development of the central nervous system. Di Cunto et al. (2000) concluded that citron-K is critical for in vivo cytokinesis in neuronal precursor cells. For a further review of citron kinases, see Di Cunto et al., *J Biol Chem* Nov. 6, 1998; 273(45):29706–11; Di Cunto, et al., *Neuron* 28: 115–127, 2000; Madaule et al., *FEBS Lett.* 377: 243–248, 1995; and Nagase et al., *DNA Res.* 6: 63–70, 1999.

Kinase proteins, particularly members of the citron kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the citron kinase subfamily.

SUMMARY OF THE INVENTION

The present invention is based in part on the identification of amino acid sequences of human kinase peptides and proteins that are related to the citron kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in liver, proliferating human erythroid cells of the blood, and glioblastomas of the brain.

DESCRIPTION OF THE FIGURE SHEETS

FIGS. 1A–1B provide the nucleotide sequence of a cDNA molecule that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in liver, proliferating human erythroid cells of the blood, and glioblastomas of the brain.

FIGS. 2A–2F provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIGS. 3A–3Z provide genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 13 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the citron kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the citron kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the citron kinase subfamily and the expression pattern observed. Experimental data as provided in FIG. 1 indicates expression in liver, proliferating human erythroid cells of the blood, and glioblastomas of the brain. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known citron family or subfamily of kinase proteins.

Specific Embodiments

Peptide Molecules

The present invention provides nucleic acid sequences that encode protein molecules that have been identified as being members of the kinase family of proteins and are related to the citron kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in liver, proliferating human erythroid cells of the blood, and glioblastomas of the brain. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques.

For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated in FIG. 3, the map position of the kinase gene of the present invention was determined to be on human chromosome 12.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated in FIG. 3, the map position of the kinase gene of the present invention was determined to be on human chromosome 12. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been identified at 13 different nucleotide positions in the gene encoding the kinase proteins of the present invention.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in proliferating human erythroid cells of the blood and in glioblastomas of the brain, as indicated by virtual northern blot analysis. Additionally, the tissue source of the cDNA clone of the present invention indicates expression in the liver. A large percentage of pharmaceutical agents are being developed that modulate the activity of kinase proteins, particularly members of the citron subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in liver, proliferating human erythroid cells of the blood, and glioblastomas of the brain. Such uses can readily be determined using the information provided herein, that which is known in the art, and routine experimentation.

The proteins of the present invention (including variants and fragments that may have been disclosed prior to the present invention) are useful for biological assays related to kinases that are related to members of the citron subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in proliferating human erythroid cells of the blood and in glioblastomas of the brain, as indicated by virtual northern blot analysis. Additionally, the tissue source of the cDNA clone of the present invention indicates expression in the liver.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in liver, proliferating human erythroid cells of the blood, and glioblastomas of the brain. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in proliferating human erythroid cells of the blood and in glioblastomas of the brain, as indicated by virtual northern blot analysis. Additionally, the tissue source of the cDNA clone of the present invention indicates expression in the liver.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in liver, proliferating human erythroid cells of the blood, and glioblastomas of the brain. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in liver, proliferating human erythroid cells of the blood, and glioblastomas of the brain. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10–11):983–985 (1996)), and Linder, M. W. (Clin. Chem. 43(2):254–266 (1997) outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in liver, proliferating human erythroid cells of the blood, and glioblastomas of the brain.

Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidinibiotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of Antibody Uses The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in proliferating human erythroid cells of the blood and in glioblastomas of the brain, as indicated by virtual northern blot analysis. Additionally, the tissue source of the cDNA clone of the present invention indicates expression in the liver. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in liver, proliferating human erythroid cells of the blood, and glioblastomas of the brain. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in liver, proliferating human erythroid cells of the blood, and glioblastomas of the brain. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in liver, proliferating human erythroid cells of the blood, and glioblastomas of the brain. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention turter provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated in FIG. 3, the map position of the kinase gene of the present invention was determined to be on human chromosome 12.

FIG. 3 provides information on SNPs that have been identified at 13 different nucleotide positions in the gene encoding the kinase proteins of the present invention.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 13 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated in FIG. 3, the map position of the kinase gene of the present invention was determined to be on human chromosome 12.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in proliferating human erythroid cells of the blood and in glioblastomas of the brain, as indicated by virtual northern blot analysis. Additionally, the tissue source of the cDNA clone of the present invention indicates expression in the liver. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in proliferating human erythroid cells of the blood and in glioblastomas of the brain, as indicated by virtual northern blot analysis. Additionally, the tissue source of the cDNA clone of the present invention indicates expression in the liver.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in liver, proliferating human erythroid cells of the blood, and glioblastomas of the brain. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in proliferating human erythroid cells of the blood and in glioblastomas of the brain, as indicated by virtual northern blot analysis. Additionally, the tissue source of the cDNA clone of the present invention indicates expression in the liver. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in liver, proliferating human erythroid cells of the blood, and glioblastomas of the brain.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been identified at 13 different nucleotide positions in the gene encoding the kinase proteins of the present invention. As indicated in FIG. 3, the map position of the kinase gene of the present invention was determined to be on human chromosome 12. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been identified at 13 different nucleotide positions in the gene encoding the kinase proteins of the present invention.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in proliferating human erythroid cells of the blood and in glioblastomas of the brain, as indicated by virtual northern blot analysis. Additionally, the tissue source of the cDNA clone of the present invention indicates expression in the liver. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been identified at 13 different nucleotide positions in the gene encoding the kinase proteins of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli,* Streptomyces, and Salmonella typhimurium. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11 d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein.

These are found for example in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, a lipofection, and other techniques such as those found in Sambrook, et al. (*Molecular Cloning: A Laboratory Manual. 2nd, ed, Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes a polypeptide comprising the amino acid sequence of SEQ ID NO:2;
   (b) a nucleotide sequence consisting of SEQ ID NO:1;
   (c) a nucleotide sequence consisting of SEQ ID NO:3; and
   (d) a nucleotide sequence that is completely complementary to a nucleotide sequence of (a)–(c).

2. A nucleic acid vector comprising the nucleic acid molecule of claim 1.

3. A host cell containing the vector of claim 2.

4. A process for producing a polypeptide comprising culturing the host cell of claim 3 under conditions sufficient for the production of said polypeptide, and recovering said polypeptide.

5. An isolated polynucleotide consisting of the nucleotide sequence set forth in SEQ ID NO:1.

6. An isolated polynucleotide consisting of the nucleotide sequence set forth in SEQ ID NO:3.

7. A vector according to claim 2, wherein said vector is selected from the group consisting of a plasmid, a virus, and a bacteriophage.

8. A vector according to claim 2, wherein said isolated nucleic acid molecule is inserted into said vector in proper orientation and correct reading frame such that a polypeptide comprising SEQ ID NO:2 may be expressed by a cell transformed with said vector.

9. A vector according to claim 8, wherein said isolated nucleic acid molecule is operatively linked to a promoter sequence.

* * * * *